(12) United States Patent
Campbell et al.

(10) Patent No.: US 9,243,001 B2
(45) Date of Patent: Jan. 26, 2016

(54) SUBSTITUTED BENZENE COMPOUNDS

(71) Applicant: Epizyme, Inc., Cambridge, MA (US)

(72) Inventors: John Emmerson Campbell, Cambridge, MA (US); Kevin Wayne Kuntz, Woburn, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 14/210,638

(22) Filed: Mar. 14, 2014

(65) Prior Publication Data

US 2014/0315945 A1    Oct. 23, 2014

Related U.S. Application Data

(60) Provisional application No. 61/791,858, filed on Mar. 15, 2013.

(51) Int. Cl.
| | | |
|---|---|---|
| C07D 491/02 | (2006.01) | |
| A61K 31/44 | (2006.01) | |
| C07D 513/04 | (2006.01) | |
| C07D 471/04 | (2006.01) | |
| C07D 231/56 | (2006.01) | |
| C07D 235/14 | (2006.01) | |
| C07D 277/30 | (2006.01) | |
| C07D 277/64 | (2006.01) | |
| C07D 263/56 | (2006.01) | |
| C07D 405/12 | (2006.01) | |
| C07D 409/12 | (2006.01) | |

(52) U.S. Cl.
CPC ............ *C07D 513/04* (2013.01); *C07D 231/56* (2013.01); *C07D 235/14* (2013.01); *C07D 263/56* (2013.01); *C07D 277/30* (2013.01); *C07D 277/64* (2013.01); *C07D 405/12* (2013.01); *C07D 409/12* (2013.01); *C07D 471/04* (2013.01)

(58) Field of Classification Search
None
See application file for complete search history.

(56) References Cited

U.S. PATENT DOCUMENTS

| | | | | |
|---|---|---|---|---|
| 4,146,631 A | * | 3/1979 | Ford et al. ................ | 514/381 |
| 4,474,792 A | * | 10/1984 | Erickson ................... | 514/381 |
| 2010/0324056 A1 | | 12/2010 | Broka et al. | |

FOREIGN PATENT DOCUMENTS

| | | |
|---|---|---|
| WO | WO 9634866 A1 * | 11/1996 |
| WO | WO 00/26202 A1 | 5/2000 |
| WO | WO 03/015774 A1 | 2/2003 |
| WO | WO 2004/089949 A1 | 10/2004 |
| WO | WO 2007/036733 A1 | 4/2007 |
| WO | WO 2012/142504 A1 | 10/2012 |

OTHER PUBLICATIONS

CAS Registry No. 1171403-50-1, STN Entry Date Aug. 2, 2009.
CAS Registry No. 926787-61-3, STN Entry Date Mar. 18, 2007.
CAS Registry No. 1327994-90-0, STN Entry Date Sep. 4, 2011.
CAS Registry No. 1328924-54-4, STN Entry Date Sep. 6, 2011.
CAS Registry No. 1208792-98-6, STN Entry Date Mar. 11, 2010.

* cited by examiner

*Primary Examiner* — Heidi Reese
(74) *Attorney, Agent, or Firm* — Cooley LLP; Ivor R. Elrifi; Heidi A. Erlacher

(57) ABSTRACT

The present invention relates to azole compounds. The present invention also relates to pharmaceutical compositions containing these compounds and methods of treating cancer by administering these compounds and pharmaceutical compositions to subjects in need thereof. The present invention also relates to the use of such compounds for research or other non-therapeutic purposes.

4 Claims, No Drawings

SEQUENCE LISTING

<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 1

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE

```
<222> LOCATION: (7)..(7)
<223> OTHER INFORMATION: wherein the lysine is dimethylated
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 2

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```

SUBSTITUTED BENZENE COMPOUNDS

RELATED APPLICATIONS

This application claims priority to, and the benefit of, U.S. provisional application No. 61/791,858, filed Mar. 15, 2013, the entire content of which is incorporated herein by reference in its entirety.

INCORPORATION-BY-REFERENCE OF SEQUENCE LISTING

The contents of the text file named "EPIZ-018001US-ST25.txt", which was created on Jul. 3, 2014 and is 1.2 KB in size, are hereby incorporated by reference in their entireties.

BACKGROUND OF THE INVENTION

There is an ongoing need for new agents as inhibitors of EZH2 mutants, which can be used for treating an EZH2-mediated disorder (e.g., cancer).

SUMMARY OF THE INVENTION

In one aspect, the present invention features an azole compound of Formula (I) below or a pharmaceutically acceptable salt thereof:

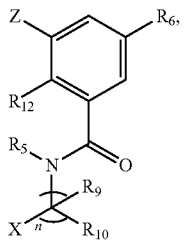

(I)

wherein

Z is $NR_7R_8$, $OR_7$, $S(O)_aR_7$, or $CR_7R_8R_{14}$, in which a is 0, 1, or 2;

each of $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is H, halo, cyano, azido, $OR_a$, —$NR_aR_b$, —$C(O)R_a$, —$C(O)OR_a$, —$C(O)NR_aR_b$, —$NR_bC(O)R_a$, —$S(O)_bR_a$, —$S(O)_bNR_aR_b$, or $R_{S2}$, in which $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S3}$, and $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of H, halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $COOR_e$, —$S(O)_2R_e$, —$NR_eR_f$, and —$C(O)NR_eR_f$, each of $R_e$ and $R_f$ independently being H or $C_1$-$C_6$ alkyl optionally substituted with OH, O—$C_1$-$C_6$ alkyl, or NH—$C_1$-$C_6$ alkyl, or -$Q_3$-$T_3$ is oxo; or -$Q_2$-$T_2$ is oxo; or any two neighboring -$Q_2$-$T_2$, when $R_6$ is $C_6$-$C_{10}$ aryl or 5- or 6-membered heteroaryl, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —$C(O)R_g$, —$C(O)OR_g$, —$C(O)NR_gR_h$, —$C(O)NR_gOR_h$, —$NR_gC(O)R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 14-membered heterocycloalkyl, or 5- or 6-membered heteroaryl, and each of $R_{S6}$ and $R_{S7}$ is optionally substituted with one or more -$Q_5$-$T_5$, wherein $Q_5$ is a bond, C(O), C(O)$NR_k$, $NR_kC(O)$, $NR_k$, $S(O)_2$, $NR_kS(O)_2$, or $C_1$-$C_3$ alkyl linker, $R_k$ being H or $C_1$-$C_6$ alkyl, and $T_5$ is H, halo, $C_1$-$C_6$ alkyl, $C_2$-$C_6$ alkenyl, $C_2$-$C_6$ alkynyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, and $R_{12}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)N$R_m$, N$R_m$C(O), S(O)$_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_p$$R_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo;

$R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

X is a monocyclic or multicyclic (e.g., bicyclic) 5 to 10-membered saturated, unsaturated, or aromatic ring containing 2-4 heteroatom ring members and optionally substituted with one or more -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —O$R_n$, —N$R_n$$R_r$, —C(O)$R_n$, —C(O)O$R_n$, —C(O)N$R_n$$R_r$, —S(O)$_2$$R_n$, —S(O)$_2$N$R_n$$R_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, O$R_s$, COO$R_s$, —S(O)$_2$$R_s$, —N$R_s$$R_t$, and —C(O)N$R_s$$R_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl; and n is 0, 1, 2, 3, 4, or 5.

One subset of the compounds of Formula (I) features X being azole or a bicyclic ring containing an azole moiety. In one embodiment, X is not 5-methoxy-1H-pyrrolo[3,2-b]pyridin-7(4H)-one, 5-methoxy-1H-pyrazolo[4,3-b]pyridin-7(4H)-one, 5-methoxy-1H-imidazo[4,5-b]pyridin-7(4H)-one, 5-methoxy-2-methyl-1H-imidazo[4,5-b]pyridin-7(4H)-one, or 5-methoxy-3-methyl-1H-pyrazolo[4,3-b]pyridin-7 (4H)-one.

Another subset of the compounds of Formula (I) features X being

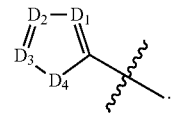

In this formula, each of $D_1$, $D_2$, and $D_3$, independently, is $CR^{901}$ or N, provided that at least one of $D_1$, $D_2$, and $D_3$ is N. $D_4$ is O, S, or $NR^{902}$. Each $R^{901}$ and $R^{902}$, independently, is -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —O$R_n$, —N$R_n$$R_r$, —C(O)$R_n$, —C(O)O$R_n$, —C(O)N$R_n$$R_r$, —S(O)$_2$$R_n$, —S(O)$_2$N$R_n$$R_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, O$R_s$, COO$R_s$, —S(O)$_2$$R_s$, —N$R_s$$R_t$, and —C(O)N$R_s$$R_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. In some embodiments, $D_1$ is N; each of $D_2$ and $D_3$, independently, is $CR^{901}$; and $D_4$ is $NR^{902}$. In other embodiments, each of $D_1$ and $D_2$, independently, is $CR^{901}$; $D_3$ is N; and $D_4$ is $NR^{902}$. In still some embodiments, each of $D_1$ and $D_2$ is N; $D_3$ is $CR^{901}$; and $D_4$ is $NR^{902}$. In yet some embodiments, each of $D_1$ and $D_3$ is, independently, $CR^{901}$; $D_2$ is N, and $D_4$ is $NR^{902}$. In further some embodiments, $D_1$ is N; each of $D_2$ and $D_3$, independently, is $CR^{901}$; and $D_4$ is O or S.

Another subset of the compounds of Formula (I) features X being

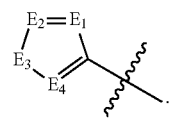

In this formula, each of $E_1$, $E_2$, and $E_4$, independently, is $CR^{903}$ or N, provided that at least one of $E_1$, $E_2$, and $E_4$ is N. $E_3$ is O, S, or $NR^{904}$. Each of $R^{903}$ and $R^{904}$, independently, is -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_r$, —$S(O)_2R_n$, —$S(O)_2NR_nR_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_s$, $COOR_s$, —$S(O)_2R_s$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. In some embodiments, $E_1$ is N; each of $E_2$ and $E_4$, independently, is $CR^{903}$; and $E_3$ is $NR^{904}$. In other embodiments, each of $E_1$ and $E_4$, independently, is $CR^{903}$; $E_2$ is N; and $E_3$ is $NR^{904}$. In still other embodiments, each of $E_1$ and $E_2$, independently, is $CR^{903}$; $E_3$ is $NR^{904}$; and $E_4$ is N. In yet other embodiments, each of $E_1$ and $E_2$, independently, is $CR^{903}$; $E_3$ is O; and $E_4$ is N.

Another subset of the compounds of Formula (I) features X being

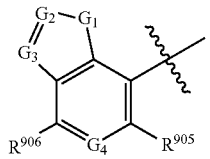

In this formula, $G_1$ is O, S, or $NR^{907}$; each of $G_2$, $G_3$, and $G_4$, independently, is N or $CR^{908}$, provided that at least one of $G_2$, $G_3$, and $G_4$ is N. Each of $R^{905}$, $R^{906}$, $R^{907}$, and $R^{908}$, independently, is -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_r$, —$S(O)_2R_n$, —$S(O)_2NR_nR_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_s$, $COOR_s$, —$S(O)_2R_s$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. In some embodiments, $G_1$ is $NR^{907}$; $G_2$ is $CR^{908}$; and each of $G_3$ and $G_4$ is N. In other embodiments, $G_1$ is $NR^{907}$; each of $G_2$ and $G_4$, independently, is $CR^{908}$; and $G_3$ is N. In still other embodiments, $G_1$ is $NR^{907}$; each of $G_2$ and $G_4$ is N, and $G_3$ is $CR^{908}$. In yet other embodiments, $G_1$ is $NR^{907}$; $G_2$ is N; and each of $G_3$ and $G_4$, independently, is $CR^{908}$.

Another subset of the compounds of Formula (I) features X being

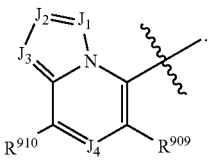

In this formula, each of $J_1$, $J_2$, $J_3$, and $J_4$, independently, is N or $CR^{911}$, provided that at least one of $J_1$, $J_2$, $J_3$, and $J_4$ is N. Each of $R^{909}$, $R^{910}$, and $R^{911}$, independently, is -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_r$, —$S(O)_2R_n$, —$S(O)_2NR_nR_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_E$, $COOR_s$, —$S(O)_2R_s$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. In some embodiments, each of $J_1$ is N, and each of $J_2$, $J_3$, and $J_4$, independently, is $CR^{19}$.

Another subset of the compounds of Formula (I) features X being

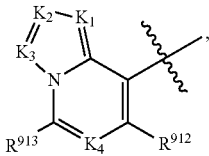

In this formula, each of $K_1$, $K_2$, $K_3$, and $K_4$, independently, is N or $CR^{914}$, provided that at least one of $K_1$, $K_2$, $K_3$, and $K_4$ is N. Each of $R^{912}$, $R^{913}$, and $R^{914}$, independently, is -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_r$, —$S(O)_2R_n$, —$S(O)_2NR_nR_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_E$, $COOR_s$, —$S(O)_2R_s$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. In some embodiments, $K_1$ is N; and each of $K_2$, $K_3$, and $K_4$, independently, is $CR^{914}$. In some embodiments, each of $K_1$ and $K_4$ is N; and each of $K_2$ and $K_3$ independently, is $CR^{914}$.

Another subset of the compounds of Formula (I) features X being

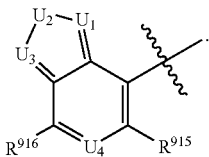

In this formula, each of $U_1$, $U_3$, and $U_4$, independently, is N or $CR^{917}$, provided that at least one of $U_1$, $U_3$, and $U_4$ is N. $U_2$ is O, S, or $NR^{918}$. Each of $R^{915}$, $R^{916}$, $R^{917}$ and $R^{918}$, independently, is -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_r$, —$S(O)_2R_n$, —$S(O)_2NR_nR_r$, or $R_{S9}$, in which each of $R_n$ and $R_r$, independently is H or $R_{S10}$, each of $R_{S6}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_E$, $COOR_s$, —$S(O)_2R_s$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. In some embodiments, $U_1$ is N; $U_2$ is $NR^{918}$; and each of $U_3$ and $U_4$, independently, is $CR^{917}$.

Another subset of the compounds of Formula (I) features X being

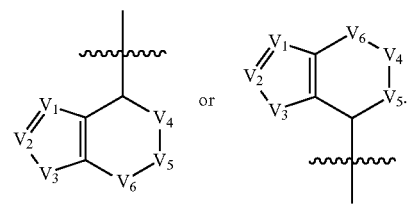

In this formula, each of $V_1$ and $V_2$, independently, is N or $CR^{919}$, provided that at least one of $V_1$ and $V_2$ is N; $V_3$ is O, S, or $NR^{920}$. Each of $V_4$, $V_5$, and $V_6$ is O, S, or $NR^{921}$, or $CR^{922}R^{923}$; and each of $R^{919}$, $R^{920}$, $R^{921}$, $R^{922}$, and $R^{923}$, independently, is -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_r$, —$S(O)_2R_n$, —$S(O)_2NR_nR_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_E$, $COOR_s$, —$S(O)_2R_s$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-C$_1$-C$_6$ alkylamino, C$_3$-C$_8$ cycloalkyl, C$_6$-C$_{10}$ aryl, 4 to 12-membered heterocycloalkyl, and 5- or 6-membered heteroaryl.

Another subset of the compounds of Formula (I) features X being imidazole-2-yl, imidazol-4-yl, triazol-3-yl, 3H-imidazo[4,5-c]pyridin-7-yl, 1H-benzo[d]imidazol-4-yl, 1H-indazol-7-yl, isoxazol-3-yl, thiazol-2-yl, 1H-pyrazolo[4,3-c]pyridine-7-yl, imidazo[1,2-a]pyridine-8-yl, imidazo[1,2-c]pyrimidin-8-yl, 1,4,6,7-tetrahydropyrano[4,3-c]pyrazol-7-yl, 1,4,6,7-tetrahydropyrano[3,4-]imidazole-7-yl, or 4,5,6,7-tetrahydro-1H-benzo[d]imidazole-4-yl.

The compounds of Formula (I) and any subset described above can include one or more of the following features:

Z is NR$_7$R$_8$.

Z is CR$_7$R$_8$R$_{14}$.

Z is OR$_7$.

Z is S(O)$_a$R$_7$, in which a is 0, 1, or 2.

Z is SR$_7$.

R$_6$ is C$_6$-C$_{10}$ aryl or 5- or 6-membered heteroaryl, each of which is optionally, independently substituted with one or more -Q$_2$-T$_2$, wherein Q$_2$ is a bond or C$_1$-C$_3$ alkyl linker, and T$_2$ is H, halo, cyano, —OR$_e$, —NR$_c$R$_d$, —C(O)NR$_c$R$_d$, —NR$_d$C(O)R$_c$, —S(O)$_2$R$_c$, —S(O)$_2$NR$_c$R$_d$, or R$_{S4}$, in which each of R$_c$ and R$_d$, independently is H or R$_{S5}$, each of R$_{S4}$ and R$_{S5}$, independently, is C$_1$-C$_6$ alkyl, or R$_c$ and R$_d$, together with the N atom to which they are attached, form a 4 to 7-membered heterocycloalkyl ring having 0 or 1 additional heteroatom, and each of R$_{S4}$, R$_{S5}$, and the 4 to 7-membered heterocycloalkyl ring formed by R$_c$ and R$_d$, is optionally, independently substituted with one or more -Q$_3$-T$_3$, wherein Q$_3$ is a bond or C$_1$-C$_3$ alkyl linker and T$_3$ is selected from the group consisting of H, halo, C$_1$-C$_6$ alkyl, 4 to 7-membered heterocycloalkyl, OR$_e$, —S(O)$_2$R$_e$, and —NR$_e$R$_f$, each of R$_e$ and R$_f$ independently being H or C$_1$-C$_6$ alkyl optionally substituted with OH, O—C$_1$-C$_6$ alkyl, or NH—C$_1$-C$_6$ alkyl, or -Q$_3$-T$_3$ is oxo; or any two neighboring -Q$_2$-T$_2$, together with the atoms to which they are attached form a 5- or 6-membered ring optionally containing 1-4 heteroatoms selected from N, O and S.

R$_c$ and R$_d$, together with the N atom to which they are attached, form a 4 to 7-membered heterocycloalkyl ring having 0 or 1 additional heteroatoms to the N atom and the ring is optionally substituted with one or more -Q$_3$-T$_3$, wherein the heterocycloalkyl is azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, or morpholinyl.

R$_6$ is phenyl or 5- or 6-membered heteroaryl substituted with O—C$_{1-6}$ alkyl or NH—C$_{1-6}$ alkyl, each of which is optionally substituted with hydroxyl, O—C$_{1-3}$ alkyl or NH—C$_{1-3}$ alkyl, each of the O—C$_{1-3}$ alkyl and NH—C$_{1-3}$ alkyl being optionally further substituted with O—C$_{1-3}$ alkyl or NH—C$_{1-3}$ alkyl.

R$_6$ is

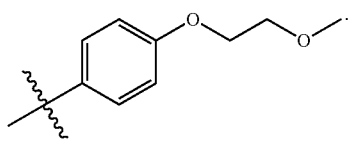 [SMILES: *c1ccc(OCCOC)cc1]

R$_6$ is halo, C$_1$-C$_3$ alkyl, C$_2$-C$_6$ alkenyl, C$_3$-C$_6$ cycloalkyl, C(O)H, or —C(O)R$_a$, in which R$_a$ is C$_1$-C$_6$ alkyl or 4 to 12-membered (e.g., 4 to 7-membered) heterocycloalkyl.

R$_6$ is F, Br, or Cl.

R$_6$ is Cl.

R$_6$ is ethynyl substituted with one or more -Q$_2$-T$_2$, in which Q$_2$ is a bond or C$_1$-C$_3$ alkyl linker and T$_2$ is C$_1$-C$_6$ alkyl, C$_3$-C$_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -Q$_3$-T$_3$.

R$_6$ is

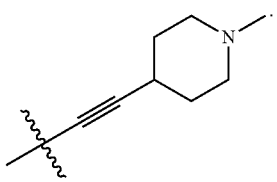 [SMILES: *C#CC1CCN(C)CC1]

R$_7$ is C$_3$-C$_8$ cycloalkyl or 4 to 7-membered heterocycloalkyl, each optionally substituted with one or more -Q$_5$-T$_5$.

R$_7$ is piperidinyl, tetrahydropyran, tetrahydro-2H-thiopyranyl, piperazinyl, cyclopentyl, cyclohexyl, pyrrolidinyl, or cycloheptyl, each optionally substituted with one or more -Q$_5$-T$_5$.

R$_8$ is H or C$_1$-C$_6$ alkyl which is optionally substituted with one or more substituents selected from the group consisting of halo, hydroxyl, COOH, C(O)O—C$_1$-C$_6$ alkyl, cyano, C$_1$-C$_6$ alkoxyl, amino, mono-C$_1$-C$_6$ alkylamino, and di-C$_1$-C$_6$ alkylamino.

R$_7$ is piperidinyl, tetrahydropyran, cyclopentyl, or cyclohexyl, each optionally substituted with one -Q$_5$-T$_5$ and R$_8$ is ethyl.

R$_7$ is

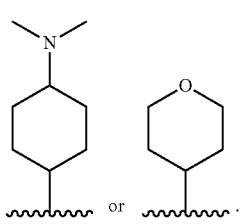

R$_7$ is

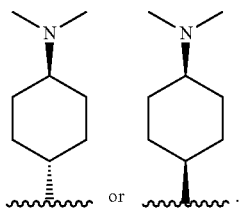

R₇ is

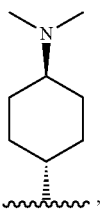

R₇ is

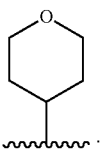

R₇ is

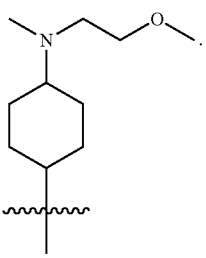 [SMILES: *C1CCC(N(C)CCOC)CC1]

R₇ is

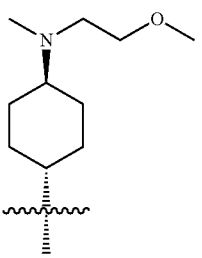

R₇ is

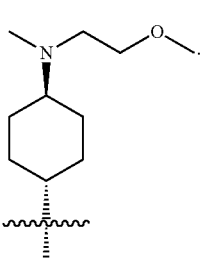

Each of R₉ and R₁₀ is H.
n is 0, 1, or 2.

Still another subset of the compounds of Formula (I) includes those of Formula (VIa)

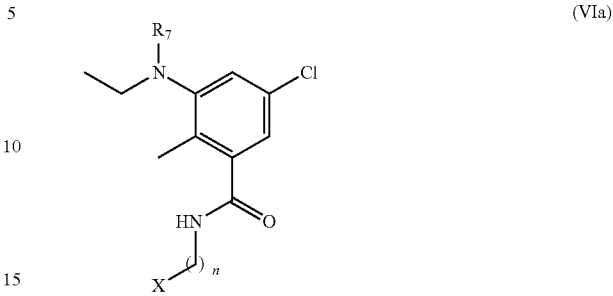

(VIa)

wherein R₇ is piperidinyl, tetrahydropyran, cyclopentyl, or cyclohexyl, each optionally substituted with one -Q₅-T₅; n is 1 or 2; and X is

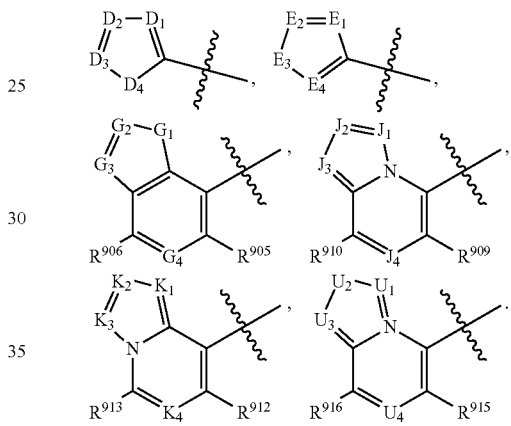

Each of $D_1$, $D_2$, and $D_3$, independently, is $CR^{901}$ or N, provided that at least one of $D_1$, $D_2$, and $D_3$ is N; $D_4$ is O, S, or $NR^{902}$. Each of $E_1$, $E_2$, and $E_4$, independently, is $CR^{903}$ or N, provided that at least one of $E_1$, $E_2$, and $E_4$ is N. $E_3$ is O, S, or $NR^{904}$. $G_1$ is O, S, or $NR^{907}$; each of $G_2$, $G_3$, and $G_4$, independently, is N or $CR^{908}$, provided that at least one of $G_2$, $G_3$, and $G_4$ is N. Each of $J_1$, $J_2$, $J_3$, and $J_4$, independently, is N or $CR^{911}$, provided that at least one of $J_1$, $J_2$, $J_3$, and $J_4$ is N. Each of $K_1$, $K_2$, $K_3$, and $K_4$, independently, is N or $CR^{914}$, provided that at least one of $K_1$, $K_2$, $K_3$, and $K_4$ is N. Each of $U_1$, $U_3$, and $U_4$, independently, is N or $CR^{917}$, provided that at least one of $U_1$, $U_3$, and $U_4$ is N. $U_2$ is O, S, or $NR^{918}$. Each of $R_{901}$, $R^{902}$, $R^{903}$, $R^{904}$, $R^{905}$, $R^{906}$, $R^{907}$, $R^{908}$, $R^{909}$, $R^{910}$, $R^{911}$, $R^{912}$, $R^{913}$, $R^{914}$, $R^{915}$, $R^{916}$, $R^{917}$ and $R^{918}$, independently, is $-Q_7-T_7$, wherein $Q_7$ is a bond or $C_1-C_3$ alkyl linker each optionally substituted with halo, cyano, hydroxyl or $C_1-C_6$ alkoxy, and $T_7$ is H, $-OR_n$, $-NR_nR_r$, $-C(O)R_n$, $-C(O)OR_n$, $-C(O)NR_nR_r$, $-S(O)_2R_n$, $-S(O)_2NR_nR_r$, or $R_{S9}$, in which each of $R_n$ and $R_r$, independently is H or $R_{S10}$, each of $R_{S9}$ and $R_{S10}$, independently, is $C_1-C_6$ alkyl, $C_3-C_8$ cycloalkyl, $C_6-C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more $-Q_8-T_8$, wherein $Q_8$ is a bond or $C_1-C_3$ alkyl linker each optionally substituted with halo, cyano, hydroxyl or $C_1-C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_s$, $COOR_s$, $-S(O)_2R_5$, $-NR_sR_t$, and $-C(O)NR_sR_t$, each of $R_s$ and $R_t$ independently being H or $C_1$-$C_6$ alkyl, or $-Q_8$-$T_8$ is oxo; or $-Q_7$-$T_7$ is oxo; or any two neighboring $-Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

The present invention also provides pharmaceutical compositions comprising one or more pharmaceutically acceptable carriers and one or more compounds selected from those of any of the Formulae described herein.

Another aspect of this invention is a method of treating or preventing cancer. The method includes administering to a subject in need thereof a therapeutically effective amount of one or more compounds selected from those of any of the Formulae described herein.

Unless otherwise stated, any description of a method of treatment includes uses of the compounds to provide such treatment or prophylaxis as is described in the specification, as well as uses of the compounds to prepare a medicament to treat or prevent such condition. The treatment includes treatment of human or non-human animals including rodents and other disease models.

For example, the method comprises the step of administering to a subject having a cancer with aberrant H3-K27 methylation an effective amount of one or more compounds of Formulae described herein, wherein the compound(s) inhibits histone methyltransferase activity of EZH2, thereby treating the cancer. Examples of aberrant H3-K27 methylation may include a global increase in and/or altered distribution of H3-K27 di or tri-methylation within the cancer cell chromatin.

For example, the cancer is selected from the group consisting of cancers that overexpress EZH2 or other PRC2 subunits, contain loss-of-function mutations in H3-K27 demethylases such as UTX, or overexpress accessory proteins such as PHF19/PCL3 capable of increasing and or mislocalizing EZH2 activity (see references in Sneeringer et al. *Proc Natl Acad Sci USA* 107(49):20980-5, 2010).

For example, the method comprises the step of administering to a subject having a cancer overexpressing EZH2 a therapeutically effective amount of one or more compounds of Formulae described herein, wherein the compound(s) inhibits histone methyltransferase activity of EZH2, thereby treating the cancer.

For example, the method comprises the step of administering to a subject having a cancer with a loss-of-function mutation in the H3-K27 demethylase UTX a therapeutically effective amount of one or more compounds of Formulae described herein, wherein the compound(s) inhibits histone methyltransferase activity of EZH2, thereby treating the cancer.

For example, the method comprises the step of administering to a subject having a cancer overexpressing an accessory component(s) of the PRC2, such as PHF19/PCL3, a therapeutically effective amount of one or more compounds of Formulae described herein, wherein the compound(s) inhibits histone methyltransferase activity of EZH2, thereby treating the cancer.

In still another aspect, this invention relates to a method of modulating the activity of the wild-type EZH2, the catalytic subunit of the PRC2 complex which catalyzes the monothrough tri-methylation of lysine 27 on histone H3 (H3-K27). For example, the present invention relates to a method of inhibiting the activity of EZH2 in a cell. This method can be conducted either in vitro or in vivo.

In yet another aspect, this invention features to a method of inhibiting in a subject conversion of H3-K27 to trimethylated H3-K27. The method comprises administering to a subject a therapeutically effective amount of one or more of the compounds of Formulae described herein to inhibit histone methyltransferase activity of EZH2, thereby inhibiting conversion of H3-K27 to trimethylated H3-K27 in the subject.

For example, the method comprises the step of administering to a subject having a cancer expressing a mutant EZH2 (e.g., a Y641, A677, and/or A687 mutant of EZH2) a therapeutically effective amount of one or more compounds of Formulae described herein, wherein the compound(s) inhibits histone methyltransferase activity of EZH2, thereby treating the cancer.

For example, the cancer is selected from the group consisting of follicular lymphoma and diffuse large B-cell lymphoma (DLBCL) of germinal center B cell-like (GCB) subtype. For example, the cancer is lymphoma, leukemia or melanoma. Preferably, the lymphoma is non-Hodgkin's lymphoma (NHL), follicular lymphoma or diffuse large B-cell lymphoma. Alternatively, the leukemia is chronic myelogenous leukemia (CML), acute myeloid leukemia, acute lymphocytic leukemia or mixed lineage leukemia.

For example, the precancerous condition is myelodysplastic syndromes (MDS, formerly known as preleukemia).

For example, the cancer is a hematological cancer.

For example, the cancer is selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, and prostate cancer. Preferably, a subject in need thereof is one who had, is having or is predisposed to developing brain and CNS cancer, kidney cancer, ovarian cancer, pancreatic cancer, leukemia, lymphoma, myeloma, and/or sarcoma. Exemplary brain and central CNS cancer includes medulloblastoma, oligodendroglioma, atypical teratoid/rhabdoid tumor, choroid plexus carcinoma, choroid plexus papilloma, ependymoma, glioblastoma, meningioma, neuroglial tumor, oligoastrocytoma, oligodendroglioma, and pineoblastoma. Exemplary ovarian cancer includes ovarian clear cell adenocarcinoma, ovarian endomethrioid adenocarcinoma, and ovarian serous adenocarcinoma. Exemplary pancreatic cancer includes pancreatic ductal adenocarcinoma and pancreatic endocrine tumor. Exemplary sarcoma includes chondrosarcoma, clear cell sarcoma of soft tissue, ewing sarcoma, gastrointestinal stromal tumor, osteosarcoma, rhabdomyosarcoma, and not otherwise specified (NOS) sarcoma. Alternatively, cancers to be treated by the compounds of the present invention are non NHL cancers.

For example, the cancer is selected from the group consisting of medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid/rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, and not otherwise specified (NOS) sarcoma. Preferably, the cancer is medulloblastoma, ovarian clear cell adenocarcinoma, ovarian endomethrioid adenocarcinoma, pancreatic ductal adenocarcinoma, malignant rhabdoid tumor, atypical teratoid/rhabdoid tumor, choroid plexus carcinoma, choroid plexus papilloma, glioblastoma, meningioma, pineoblastoma, carcino sarcoma, extrarenal rhabdoid tumor, schwannoma, skin squamous cell carcinoma, chondrosarcoma, ewing sarcoma, epithelioid sarcoma, renal medullary carcinoma, diffuse large B-cell lymphoma, follicular lymphoma and/or NOS sarcoma. More preferably, the cancer is malignant rhabdoid tumor, medulloblastoma and/or atypical teratoid/rhabdoid tumor.

For example, the method comprises the step of administering to a subject having a cancer expressing a mutant EZH2 (e.g., a Y641, A677, and/or A687 mutant of EZH2) a therapeutically effective amount of one or more compounds of Formulae described herein, wherein the compound(s) inhibits activity (e.g., histone methyltransferase activity) of the mutant EZH2, the wild-type EZH2, or both, thereby treating the cancer.

For example, the method further comprises the steps of performing an assay to detect a mutant EZH2 in a sample comprising cancer cells from a subject in need thereof.

In another aspect, the invention features a method of selecting a therapy for a patient having a disease associated with EZH2-mediated protein methylation. The method includes the steps of determining the presence of gene mutation in the EZH2 gene of the subject; and selecting, based on the presence of a gene mutation in the EZH2 gene a therapy for treating the disease. In one embodiment, the therapy includes the administration of one or more of the compounds of the invention. In one embodiment, the method further includes administrating one or more of the compounds of the invention to the subject. In one embodiment, the disease is cancer and the mutation is a Y641, A677, and/or A687 mutation.

In yet another aspect, a method of treatment is provided for a patient in need thereof, the method comprising the steps of determining the presence of gene mutation in the EZH2 gene and treating the patient in need thereof, based on the presence of a gene mutation in the EZH2 gene, with a therapy that includes the administration of the compounds of the invention. In one embodiment, the patient is a cancer patient and the mutation is a Y641, A677, and/or A687 mutation.

In still another aspect, this invention relates to a method of modulating the activity of the wild-type and mutant histone methyltransferase EZH2, the catalytic subunit of the PRC2 complex which catalyzes the mono-through tri-methylation of lysine 27 on histone H3 (H3-K27). For example, the present invention relates to a method of inhibiting the activity of certain mutant forms of EZH2 in a cell. The mutant forms of EZH2 include a substitution of another amino acid residue for tyrosine 641 (Y641, also Tyr641) of wild-type EZH2. The method includes contacting the cell with an effective amount of one or more of the compounds of any Formula described herein. This method can be conducted either in vitro or in vivo.

In yet another aspect, this invention features to a method of inhibiting in a subject conversion of H3-K27 to trimethylated H3-K27. The method comprises administering to a subject expressing a mutant EZH2 (e.g., a Y641, A677, and/or A687 mutant of EZH2) a therapeutically effective amount of one or more of the compounds of any Formula described herein to inhibit histone methyltransferase activity of EZH2, thereby inhibiting conversion of H3-K27 to trimethylated H3-K27 in the subject. For example, the histone methyltransferase activity inhibited is that of the Y641 mutant of EZH2. For example, the compound of this invention selectively inhibits histone methyltransferase activity of the Y641 mutant of EZH2. For example, the Y641 mutant of EZH2 is selected from the group consisting of Y641C, Y641F, Y641H, Y641N, and Y641S.

The method of inhibiting in a subject conversion of H3-K27 to trimethylated H3-K27 may also comprise performing an assay to detect a mutant EZH2 (e.g., a Y641, A677, and/or A687 mutant of EZH2) in a sample from a subject before administering to the subject expressing a mutant EZH2 a therapeutically effective amount of one or more of the compounds of any Formula described herein. For example, performing the assay to detect the mutant EZH2 includes whole-genome resequencing or target region resequencing that detects a nucleic acid encoding the mutant EZH2. For example, performing the assay to detect the mutant EZH2 includes contacting the sample with an antibody that binds specifically to a polypeptide or fragment thereof characteristic of the mutant EZH2. For example, performing the assay to detect the mutant EZH2 includes contacting the sample under highly stringent conditions with a nucleic acid probe that hybridizes to a nucleic acid encoding a polypeptide or fragment thereof characteristic of the mutant EZH2.

Further, the invention also relates to a method of identifying an inhibitor of a mutant EZH2, the wild-type EZH2, or both. The method comprises the steps of combining an isolated EZH2 with a histone substrate, a methyl group donor, and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 (e.g., formation of trimethylated H3-K27) in the histone substrate, thereby identifying the test compound as an inhibitor of the EZH2 when methylation of H3-K27 (e.g., formation of trimethylated H3-K27) in the presence of the test compound is less than methylation of H3-K27 (e.g., formation of trimethylated H3-K27) in the absence of the test compound.

In one embodiment, performing the assay to detect methylation of H3-K27 in the histone substrate comprises measuring incorporation of labeled methyl groups.

In one embodiment, the labeled methyl groups are isotopically labeled methyl groups.

In one embodiment, performing the assay to detect methylation of H3-K27 in the histone substrate comprises contacting the histone substrate with an antibody that binds specifically to trimethylated H3-K27.

Also within the scope of the invention is a method of identifying a selective inhibitor of a mutant EZH2. The method comprises the steps of combining an isolated mutant EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the mutant EZH2 and the test compound (M+) to (b) trimethylation with the mutant EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the mutant EZH2 when the ratio (a)/(b) is less than the ratio (c)/(d).

The present invention further provides a method of identifying a subject as a candidate for treatment with one or more compounds of the invention. The method comprises the steps of performing an assay to detect a mutant EZH2 in a sample from a subject; and identifying a subject expressing a mutant EZH2 as a candidate for treatment with one or more compounds of the invention, wherein the compound(s) inhibits histone methyltransferase activity of EZH2.

Still another aspect of the invention is a method of inhibiting conversion of H3-K27 to trimethylated H3-K27. The method comprises the step of contacting a mutant EZH2, the wild-type EZH2, or both with a histone substrate comprising H3-K27 and an effective amount of a compound of the present invention, wherein the compound inhibits histone methyltransferase activity of EZH2, thereby inhibiting conversion of H3-K27 to trimethylated H3-K27.

Further, the compounds or methods described herein can be used for research (e.g., studying epigenetic enzymes) and other non-therapeutic purposes.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the invention will be apparent from the following detailed description and claims.

DETAILED DESCRIPTION OF THE INVENTION

The present invention provides novel azole compounds, synthetic methods for making the compounds, pharmaceutical compositions containing them and various uses of the compounds.

The present invention provides the compounds of Formula (I):

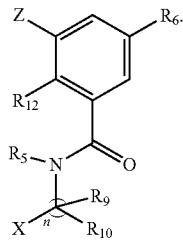

(I)

In this formula:

Z is $NR_7R_8$, $OR_s$, $S(O)_aR_7$, or $CR_7R_8R_{14}$, in which a is 0, 1, or 2;

each of $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is H, halo, cyano, azido, $OR_a$, —$NR_aR_b$, —$C(O)R_a$, —$C(O)OR_a$, —$C(O)NR_aR_b$, —$NR_bC(O)R_a$, —$S(O)_bR_a$, —$S(O)_bNR_aR_b$, or $R_{S2}$, in which $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S3}$, and $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of H, halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $COOR_e$, —$S(O)_2R_e$, —$NR_eR_f$, and —$C(O)NR_eR_f$, each of $R_e$ and $R_f$ independently being H or $C_1$-$C_6$ alkyl optionally substituted with OH, O—$C_1$-$C_6$ alkyl, or NH—$C_1$-$C_6$ alkyl, or -$Q_3$-$T_3$ is oxo; or -$Q_2$-$T_2$ is oxo; or any two neighboring -$Q_2$-$T_2$, when $R_6$ is $C_6$-$C_{10}$ aryl or 5- or 6-membered heteroaryl, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —$C(O)R_g$, —$C(O)OR_g$, —$C(O)NR_gR_h$, —$C(O)NR_gOR_h$, —$NR_gC(O)R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 14-membered heterocycloalkyl, or 5- or 6-membered heteroaryl, and each of $R_{S6}$ and $R_{S7}$ is optionally substituted with one or more -$Q_5$-$T_5$, wherein $Q_5$ is a bond, C(O), C(O)

$NR_k$, $NR_kC(O)$, $NR_k$, $S(O)_2$, $NR_kS(O)_2$, or $C_1$-$C_3$ alkyl linker, $R_k$ being H or $C_1$-$C_6$ alkyl, and $T_5$ is H, halo, $C_1$-$C_6$ alkyl, $C_2$-$C_6$ alkenyl, $C_2$-$C_6$ alkynyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, and $R_{12}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), $C(O)NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

X is a monocyclic or bicyclic 5 to 10-membered saturated, unsaturated, or aromatic ring containing 2-4 heteroatom ring members and optionally substituted with one or more -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_n$, —$S(O)_2R_n$, —$S(O)_2NR_nR_r$, or $R_{S9}$, in which each of $R_n$ and $R_r$, independently is H or $R_{S10}$, each of $R_{S8}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_s$, $COOR_s$, —$S(O)_2R_5$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di $C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl; and n is 0, 1, 2, 3, 4, or 5.

The compounds of Formula (I) can have one or more of the following features:

For example, X is azole or a bicyclic ring containing an azole moiety.

For example, X is not imidazo[1,2-a]pyridin-7-ol, 1H-pyrrolo[3,2-b]pyridin-7(4H)-one, 1H-pyrazolo[4,3-b]pyridin-7(4H)-one, or 1H-imidazo[4,5-b]pyridin-7(4H)-one.

For example, X is imidazol-2-yl, imidazol 4 yl, triazol-3-yl, 3H-imidazo[4,5-c]pyridin-7-yl, 1H-benzo[d]imidazol-4-yl, 1H-pyrazolo[4,3-c]pyridin-7-yl, imidazo[1,2-a]pyridin-8-yl, imidazo[1,2-c]pyrimidin-8-yl, 1,4,6,7-tetrahydropyrano[4,3-c]pyrazol-7-yl, 1,4,6,7-tetrahydropyrano[3,4-]imidazol-7-yl, or 4,5,6,7-tetrahydro-1H-benzo[d]imidazol-4-yl.

For example, Z is $NR_7R_8$.

For example, Z is $CR_7R_8R_{14}$.

For example, Z is $OR_s$.

For example, Z is $S(O)_aR_7$, in which a is 0, 1, or 2.

For example, Z is $SR_7$.

For example, $R_6$ is unsubstituted $C_6$-$C_{10}$ aryl or unsubstituted 5- or 6-membered heteroaryl.

For example, $R_6$ is substituted $C_6$-$C_{10}$ aryl or substituted 5- or 6-membered heteroaryl.

For example, $R_6$ is $C_6$-$C_{10}$ aryl substituted with one or more -$Q_2$-$T_2$ or 5- or 6-membered heteroaryl substituted with one or more -$Q_2$-$T_2$.

For example, $R_6$ is unsubstituted or substituted phenyl.

For example, $R_6$ is phenyl substituted with one or more -$Q_2$-$T_2$.

For example, $R_6$ is 5 to 6-membered heteroaryl containing 1-3 additional heteroatoms selected from N, O, and S and optionally substituted with one or more -$Q_2$-$T_2$.

For example, $R_6$ is pyridinyl, pyrazolyl, pyrimidinyl, quinolinyl, tetrazolyl, oxazolyl, isoxazolyl, thiazolyl, isothiazolyl, furyl, or thienyl, each of which is optionally substituted with one or more -$Q_2$-$T_2$.

For example, $R_6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —$OR_c$, —$NR_cR_d$, —$C(O)NR_cR_d$, —$NR_dC(O)R_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, or $R_c$ and $R_d$, together with the N atom to which they are attached, form a 4 to 7-membered heterocycloalkyl ring having 0 or 1 additional heteroatom, and each of $R_{S4}$, $R_{S5}$, and the 4 to 7-membered heterocycloalkyl ring formed by $R_c$ and $R_d$, is optionally, independently substituted with one or more -Q$_3$-T$_3$, wherein Q$_3$ is a bond or C$_1$-C$_3$ alkyl linker and T$_3$ is selected from the group consisting of H, halo, C$_1$-C$_6$ alkyl, 4 to 7-membered heterocycloalkyl, OR$_e$, —S(O)$_2$R$_e$, and —NR$_e$R$_f$, each of R$_e$ and R$_f$ independently being H or C$_1$-C$_6$ alkyl, or -Q$_3$-T$_3$ is oxo; or any two neighboring -Q$_2$-T$_2$, together with the atoms to which they are attached form a 5- or 6-membered ring optionally containing 1-4 heteroatoms selected from N, O and S.

For example, R$_6$ is phenyl or 5- or 6-membered heteroaryl substituted with 0-C$_{1-6}$ alkyl or NH—C$_{1-6}$ alkyl, each of which is optionally substituted with hydroxyl, 0-C$_{1-3}$ alkyl or NH—C$_{1-3}$ alkyl, each of the O—C$_{1-3}$ alkyl and NH—C$_{1-3}$ alkyl being optionally further substituted with O—C$_{1-3}$ alkyl or NH—C$_{1-3}$ alkyl.

For example, R$_6$ is

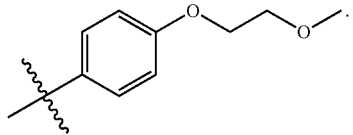 [SMILES: *c1ccc(OCCOC)cc1]

For example, R$_6$ is H.

For example, R$_6$ is halo (e.g., fluorine, chlorine, bromine, and iodine).

For example, R$_6$ is Cl.

For example, R$_6$ is C$_1$-C$_3$ alkyl optionally substituted with one or more -Q$_2$-T$_2$.

For example, R$_6$ is CF$_3$.

For example, R$_6$ is C$_2$-C$_6$ alkenyl, C$_2$-C$_6$ alkynyl, or C$_3$-C$_6$ cycloalkyl each optionally substituted with one or more -Q$_2$-T$_2$.

For example, R$_6$ is ethenyl.

For example, R$_6$ is ethynyl.

For example, R$_6$ is ethynyl substituted with one or more -Q$_2$-T$_2$, in which Q$_2$ is a bond or C$_1$-C$_3$ alkyl linker and T$_2$ is C$_1$-C$_6$ alkyl, C$_3$-C$_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -Q$_3$-T$_3$.

For example, R$_6$ is

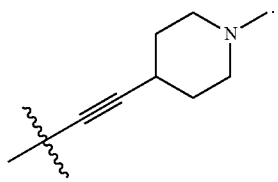 [SMILES: *C#CC1CCN(C)CC1]

For example, R$_6$ is azido.

For example, R$_6$ is cyano.

For example, R$_6$ is C(O)H.

For example, R$_6$ is OR$_a$ or —C(O)R$_a$.

For example, R$_a$ is C$_1$-C$_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more -Q$_2$-T$_2$.

For example, R$_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -Q$_2$-T$_2$.

For example, R$_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -Q$_2$-T$_2$.

For example, R$_6$ is 4 to 7-membered heterocycloalkyl optionally substituted with one or more -Q$_2$-T$_2$, and -Q$_2$-T$_2$ is oxo or Q$_2$ is a bond and T$_2$ is —OR$_c$, —NR$_c$R$_d$, —C(O)R$_c$, —C(O)OR$_c$, —S(O)$_2$R$_c$, C$_1$-C$_6$ alkyl, or 4 to 7-membered heterocycloalkyl, each of which is optionally substituted with one or more -Q$_3$-T$_3$ when R$_c$ or R$_d$ is not H.

For example, R$_6$ is —NR$_a$R$_b$, —C(O)R$_a$, —C(O)OR$_a$, —C(O)NR$_a$R$_b$, —NR$_b$C(O)R$_a$, —SR$_a$, —S(O)$_2$R$_a$, or —S(O)$_2$NR$_a$R$_b$.

For example, each of R$_a$ and R$_b$, independently is H, C$_1$-C$_6$ alkyl or C$_3$-C$_8$ cycloalkyl optionally substituted with one or more -Q$_2$-T$_2$.

For example, one of R$_a$ and R$_b$ is H.

For example, R$_a$ and R$_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more -Q$_2$-T$_2$.

For example, -Q$_2$-T$_2$ is not H.

For example, -Q$_2$-T$_2$ is oxo.

For example, Q$_2$ is a bond.

For example, Q$_2$ is an unsubstituted C$_1$-C$_3$ alkyl linker.

For example, T$_2$ is C$_1$-C$_6$ alkyl or C$_6$-C$_{10}$ aryl, each optionally substituted with one or more -Q$_3$-T$_3$.

For example, T$_2$ is an unsubstituted substituted straight chain C$_1$-C$_6$ or branched C$_3$-C$_6$ alkyl, including but not limited to, methyl, ethyl, n-propyl, i-propyl, n-butyl, s-butyl, t-butyl, n-pentyl, s-pentyl and n-hexyl.

For example, T$_2$ is phenyl.

For example, T$_2$ is halo (e.g., fluorine, chlorine, bromine, and iodine).

For example, T$_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]

heptanyl, and morpholinyl, and the like) optionally substituted with one or more -$Q_3$-$T_3$.

For example, $T_2$ is —$OR_c$, —$NR_cR_d$, —$C(O)R_c$, —$C(O)OR_c$, or —$S(O)_2R_c$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more -$Q_3$-$T_3$.

For example, each of $R_c$ and $R_d$, independently is H or $C_1$-$C_6$ alkyl optionally substituted with one or more -$Q_3$-$T_3$.

For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more -$Q_3$-$T_3$.

For example, $Q_2$ is a bond and $T_2$ is —$OR_c$, —$NR_cR_d$, —$C(O)R_c$, —$C(O)OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_e$, $COOR_e$, —$S(O)_2R_e$, —$NR_eR_f$, or —$C(O)NR_eR_f$.

For example, one of $R_d$ and $R_e$ is H.

For example, $Q_3$ is a bond or $C_1$-$C_3$ alkyl linker and $T_3$ is selected from the group consisting of $C_1$-$C_3$ alkyl, halo, $OR_e$, —$S(O)_2R_e$, —$NR_eR_f$, and —$C(O)NR_eR_f$.

For example, $Q_3$ is a bond or $C_1$-$C_3$ alkyl linker and $T_3$ is selected from the group consisting of $C_1$-$C_3$ alkyl, $OR_e$, —$S(O)_2R_e$, or —$NR_eR_f$.

For example, $R_e$ is H.

For example, $R_f$ is H.

For example, $R_7$ is not H.

For example, $R_7$ is —$C(O)R_g$.

For example, $R_7$ is —$C(O)R_g$, in which $R_g$ is $C_3$-$C_8$ cycloalkyl, or 4 to 7-membered heterocycloalkyl, $C_3$-$C_8$ cycloalkyl.

For example, $R_7$ is $C_6$-$C_{10}$ aryl substituted with one or more -$Q_5$-$T_5$.

For example, $R_7$ is phenyl optionally substituted with one or more -$Q_5$-$T_5$.

For example, $R_7$ is $C_1$-$C_6$ alkyl optionally substituted with one or more -$Q_5$-$T_5$.

For example, $R_7$ is $C_3$-$C_8$ cycloalkyl optionally substituted with one or more -$Q_5$-$T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_5$-$T_5$.

For example, $R_7$ is 8 to 14-membered heterocycloalkyl such as 1,4-dioxaspiro[4.5]decanyl (e.g., 1,4-dioxaspiro[4.5]decan-8-yl), 1,4-dioxa-8-azaspiro[4.5]decanyl (e.g., 1,4-dioxa-8-azaspiro[4.5]decan-8-yl), 1-oxaspiro[4.5]decanyl (e.g., 1-oxaspiro[4.5]decan-8-yl or 1-oxaspiro[4.5]decan-2-one-8-yl), 1-azaspiro[4.5]decanyl (e.g., 1-azaspiro[4.5]decan-8-yl or 1-azaspiro[4.5]decan-2-one-8-yl), 3'H-spiro[cyclohexane-1,1'-isobenzofuran]-yl (e.g., 3'H-spiro[cyclohexane-1,1'-isobenzofuran]-4-yl or 3'H-spiro[cyclohexane-1,1'-isobenzofuran]-3'-one-4-yl), 7'H-spiro[cyclohexane-1,5'-furo[3,4-b]pyridin]-yl (e.g., 7'H-spiro[cyclohexane-1,5'-furo[3,4-b]pyridin]-4-yl or 7'H-spiro[cyclohexane-1,5'-furo[3,4-b]pyridin]-7'-one-4-yl), or 3'H-spiro[cyclohexane-1,1'-furo[3,4-c]pyridin]-yl (e.g., 3'H-spiro[cyclohexane-1,1'-furo[3,4-c]pyridin]-4-yl or 3'H-spiro[cyclohexane-1,1'-furo[3,4-c]pyridin]-3'-one-4-yl), each optionally substituted with one or more -$Q_5$-$T_5$.

For example, $R_7$ is 5 to 6-membered heterocycloalkyl optionally substituted with one or more -$Q_5$-$T_5$ For example, $R_7$ is isopropyl.

For example, $R_7$ is piperidinyl, tetrahydropyran, tetrahydro-2H-thiopyranyl, piperazinyl, cyclopentyl, cyclohexyl, pyrrolidinyl, or cycloheptyl, each optionally substituted with one or more -$Q_5$-$T_5$.

For example, $R_7$ is piperidinyl, tetrahydropyran, cyclopentyl, or cyclohexyl, each optionally substituted with one -$Q_5$-$T_5$ and $R_8$ is ethyl.

For example, $R_7$ is tetrahydropyran or

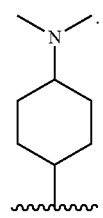

For example, $R_7$ is

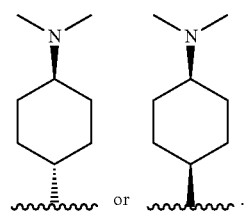

For example, $R_7$ is cyclopentyl or cyclohexyl, each optionally substituted with one -$Q_5$-$T_5$.

For example, $Q_5$ is NHC(O) and $T_5$ is $C_1$-$C_6$ alkyl or $C_1$-$C_6$ alkoxy.

For example, -$Q_5$-$T_5$ is oxo.

For example, $T_4$ is 4 to 7-membered heterocycloalkyl or $C_3$-$C_8$ cycloalkyl or $C_6$-$C_{10}$ aryl, and one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $R_7$ is cyclohexanonyl, e.g., cyclohexanon-4-yl.

For example, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_5$ is a bond and $T_5$ is $C_1$-$C_6$ alkyl, $C_3$-$C_8$ cycloalkyl, or 4 to 7-membered heterocycloalkyl.

For example, $Q_5$ is a bond and $T_5$ is 5- or 6-membered heteroaryl, amino, mono-$C_1$-$C_6$ alkylamino, di-$C_1$-$C_6$ alkylamino, $T_5$ being optionally substituted with one or more substituents selected from the group consisting of halo, hydroxyl, $C_1$-$C_6$ alkoxyl, or $C_3$-$C_8$ cycloalkyl.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5$ is $C_1$-$C_3$ alkyl linker and $T_5$ is H or $C_6$-$C_{10}$ aryl.

For example, $Q_5$ is $C_1$-$C_3$ alkyl linker and $T_5$ is $C_3$-$C_8$ cycloalkyl, 4 to 7-membered heterocycloalkyl, or $S(O)_qR_q$.

For example, $R_6$ is halo (e.g., fluorine, chlorine, bromine, and iodine) and Z is $S(O)_aR_7$, in which a is 0, 1, or 2 and $R_7$ is $C_1$-$C_6$ alkyl (e.g., methyl, ethyl, n-propyl, i-propyl, butyl, or t-butyl), $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_6$ is halo (e.g., fluorine, chlorine, bromine, and iodine) and Z is $OR_7$ in which $R_7$ is 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_{12}$ is H, methyl, ethyl, ethenyl, or halo.

For example, $R_{12}$ is methyl.

For example, $R_{12}$ is ethyl or propenyl.

For example, $R_{12}$ is methoxyl.

For example, $R_{12}$ is ethenyl.

For example, $R_8$ is H, methyl, ethyl, or ethenyl.

For example, $R_8$ is methyl.

For example, $R_8$ is ethyl.

For example, $R_8$ is propyl.

For example, $R_8$ is ethenyl or propenyl.

For example, $R_8$ is $C_1$-$C_6$ alkyl substituted with one or more substituents selected from the group consisting of halo (e.g., F, Cl, or Br), hydroxyl, or $C_1$-$C_6$ alkoxyl.

For example, $R_8$ is 4 to 7-membered optionally substituted heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like).

For example, $R_8$ is piperidinyl.

For example, $R_8$ is 4 to 7-membered optionally substituted heterocycloalkyl and $R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl or 4 to 7-membered heterocycloalkyl.

For example, Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, morpholinyl, 1,4-dioxa-8-azaspiro[4.5]decanyl, and the like) or $C_3$-$C_8$ cycloalkyl, each optionally substituted with one or more -$Q_6$-$T_6$.

For example, the ring formed by $R_7$ and $R_8$ is selected from the group consisting of azetidinyl, pyrrolidinyl, piperidinyl, morpholinyl, piperazinyl, 1,4-dioxa-8-azaspiro[4.5]decanyl, and cyclohexenyl, each optionally substituted with one -$Q_6$-$T_6$.

For example, Z is 1,4-dioxa-8-azaspiro[4.5]decan-8-yl, pyrrolidine-2,5-dione-1-yl, or piperidine-2,6-dione-1-yl.

For example, one or more -$Q_6$-$T_6$ is oxo.

For example, $T_6$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_6$ is a bond and $T_6$ is $C_1$-$C_6$ alkyl, $C_3$-$C_8$ cycloalkyl, or 4 to 7-membered heterocycloalkyl.

For example, $Q_6$ is CO, $S(O)_2$, or NHC(O); and $T_6$ is $C_1$-$C_6$ alkyl, $C_1$-$C_6$ alkoxyl, $C_3$-$C_8$ cycloalkyl, or 4 to 7-membered heterocycloalkyl.

For example, $T_6$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_5$ cycloalkyl.

For example, $Q_6$ is $C_1$-$C_3$ alkyl linker and $T_6$ is H or $C_6$-$C_{10}$ aryl.

For example, $Q_6$ is $C_1$-$C_3$ alkyl linker and $T_6$ is $C_3$-$C_8$ cycloalkyl, 4 to 7-membered heterocycloalkyl, or $S(O)_pR_p$.

For example, each of $R_p$ and $R_q$, independently, is $C_1$-$C_6$ alkyl.

For example, $R_6$ is —$S(O)_bR_a$ or azido, in which b is 0, 1, or 2 and $R_a$ is $C_1$-$C_6$ alkyl or $C_3$-$C_8$ cycloalkyl; and Z is $NR_7R_8$, in which $R_7$ is $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like), each optionally substituted with one or more -$Q_5$-$T_5$; and $R_8$ is H or $C_1$-$C_6$ alkyl (e.g., methyl, ethyl, n-propyl, i-propyl, butyl, or t-butyl).

For example, $R_6$ is halo (e.g., fluorine, chlorine, bromine, and iodine) and Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 2-oxa-6-azaspiro[3.3]heptanyl, 2,6-diazaspiro[3.3]heptanyl, 1,4-dioxa-8-azaspiro[4.5]decanyl, 1,4-dioxa-8-azaspiro[4.5]decan-8-yl, pyrrolidine-2,5-dione-1-yl, piperidine-2,6-dione-1-yl, and the like) or $C_3$-$C_8$ cycloalkyl, each optionally substituted with one or more -$Q_6$-$T_6$.

For example, each of $R_5$, $R_9$, and $R_{10}$ is H.

For example, n is 1.

For example, n is 2.

The present invention provides compounds of Formulae (IIa), (IIb) (IIc), (IId), (IIe), (IIf), (IIg), and (IIh):

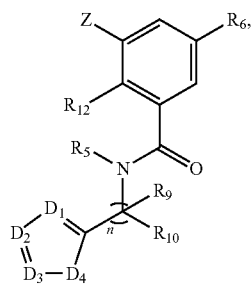

IIa

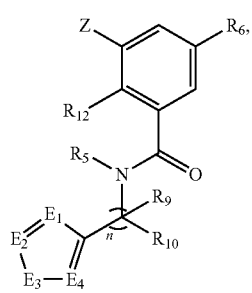

IIb

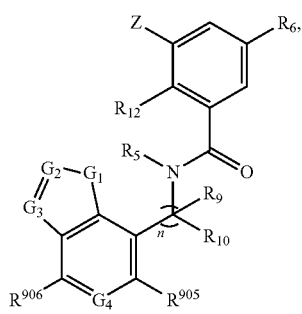

IIc

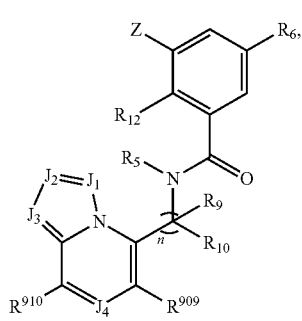

IId

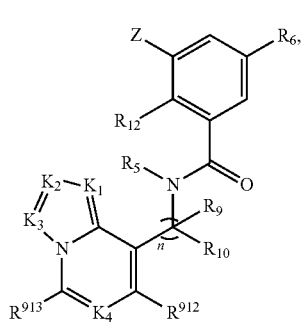

IIe

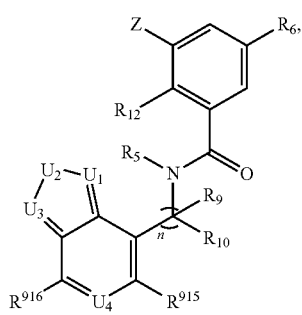

IIf

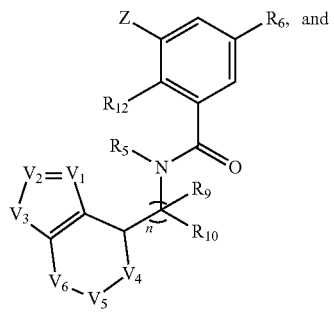

IIg

IIh

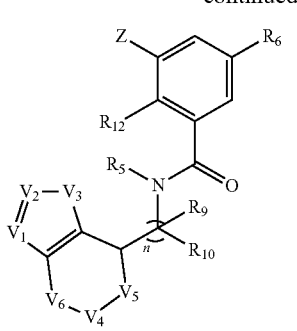

or a pharmaceutically acceptable salt thereof. Z, $R_5$, $R_6$, $R_9$, $R_{10}$, $R_{12}$ are defined herein for Formula (I). Each of $D_1$, $D_2$, and $D_3$, independently, is $CR^{901}$ or N, provided that at least one of $D_1$, $D_2$, and $D_3$ is N. $D_4$ is O, S, or $NR^{902}$. Each of $E_1$, $E_2$, and $E_4$, independently, is $CR^{903}$ or N, provided that at least one of $E_1$, $E_2$, and $E_4$ is N. $E_3$ is O, S, or $NR^{904}$. $G_1$ is O, S, or $NR^{907}$. Each of $G_2$, $G_3$, and $G_4$, independently, is N or $CR^{908}$, provided that at least one of $G_2$, $G_3$, and $G_4$ is N. Each of $J_1$, $J_2$, $J_3$, and $J_4$, independently, is N or $CR^{911}$, provided that at least one of $J_1$, $J_2$, $J_3$, and $J_4$ is N. Each of $K_1$, $K_2$, $K_3$, and $K_4$, independently, is N or $CR^{914}$, provided that at least one of $K_1$, $K_2$, $K_3$, and $K_4$ is N. Each of $U_1$, $U_3$, and $U_4$, independently, is N or $CR^{917}$, provided that at least one of $U_1$, $U_3$, and $U_4$ is N. $U_2$ is O, S, or $NR^{918}$. Each of $V_1$ and $V_2$, independently, is N or $CR^{919}$, provided that at least one of $V_1$ and $V_2$ is N. $V_3$ is O, S, or $NR^{920}$. Each of $V_4$, $V_5$, and $V_6$ is O, S, or $NR^{921}$, or $CR^{922}R^{923}$. Each of $R^{901}$, $R^{902}$, $R^{903}$, $R^{904}$, $R^{905}$, $R^{906}$, $R^{907}$, $R^{908}$, $R^{909}$, $R^{910}$, $R^{911}$, $R^{912}$, $R^{913}$, $R^{914}$, $R^{915}$, $R^{916}$, $R^{917}$, $R^{918}$, $R^{919}$, $R^{920}$, $R^{921}$, $R^{922}$, and $R^{923}$, independently, is -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_r$, —$S(O)_2R_n$, —$S(O)_2NR_nR_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_s$, $COOR_s$, —$S(O)_2R_s$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

The compounds of Formulae (IIa), (IIb), (IIc), (IId), (IIe), (IIf), (IIg), and can have one or more of the following features:

For example, Z is $NR_7R_8$.
For example, Z is $CR_7R_8R_{14}$.
For example, Z is $OR_s$.
For example, Z is $S(O)_aR_7$, in which a is 0, 1, or 2
For example, Z is $SR_7$.
For example, $R_6$ is unsubstituted $C_6$-$C_{10}$ aryl or unsubstituted 5- or 6-membered heteroaryl.
For example, $R_6$ is substituted $C_6$-$C_{10}$ aryl or substituted 5- or 6-membered heteroaryl.
For example, $R_6$ is $C_6$-$C_{10}$ aryl substituted with one or more -$Q_2$-$T_2$ or 5- or 6-membered heteroaryl substituted with one or more -$Q_2$-$T_2$.
For example, $R_6$ is unsubstituted or substituted phenyl.
For example, $R_6$ is phenyl substituted with one or more -$Q_2$-$T_2$.
For example, $R_6$ is 5 to 6-membered heteroaryl containing 1-3 additional heteroatoms selected from N, O, and S and optionally substituted with one or more -$Q_2$-$T_2$.
For example, $R_6$ is pyridinyl, pyrazolyl, pyrimidinyl, quinolinyl, tetrazolyl, oxazolyl, isoxazolyl, thiazolyl, isothiazolyl, furyl, or thienyl, each of which is optionally substituted with one or more -$Q_2$-$T_2$.
For example, $R_6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —$OR_c$, —$NR_cR_d$, —$C(O)NR_cR_d$, —$NR_dC(O)R_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, or $R_c$ and $R_d$, together with the N atom to which they are attached, form a 4 to 7-membered heterocycloalkyl ring having 0 or 1 additional heteroatom, and each of $R_{S4}$, $R_{S5}$, and the 4 to 7-membered heterocycloalkyl ring formed by $R_c$ and $R_d$, is optionally, independently substituted with one or more -$Q_3$-$T_3$, wherein $Q_3$ is a bond or $C_1$-$C_3$ alkyl linker and $T_3$ is selected from the group consisting of H, halo, $C_1$-$C_6$ alkyl, 4 to 7-membered heterocycloalkyl, $OR_e$, —$S(O)_2R_e$, and —$NR_eR_f$, each of $R_e$ and $R_f$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S.

For example, $R_6$ is H.
For example, $R_6$ is halo (e.g., fluorine, chlorine, bromine, and iodine).
For example, $R_6$ is Cl.
For example, $R_6$ is $C_1$-$C_3$ alkyl optionally substituted with one or more -$Q_2$-$T_2$.
For example, $R_6$ is $CF_3$.
For example, $R_6$ is $C_2$-$C_6$ alkenyl, $C_2$-$C_6$ alkynyl, or $C_3$-$C_6$ cycloalkyl each optionally substituted with one or more -$Q_2$-$T_2$.
For example, $R_6$ is ethenyl.
For example, $R_6$ is ethynyl.
For example, $R_6$ is ethynyl substituted with one or more -$Q_2$-$T_2$, in which $Q_2$ is a bond or $C_1$-$C_3$ alkyl linker and $T_2$ is $C_1$-$C_6$ alkyl, $C_3$-$C_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_3$-$T_3$.
For example, $R_6$ is azido.
For example, $R_6$ is cyano.

For example, $R_6$ is C(O)H.

For example, $R_6$ is $OR_a$ or —C(O)$R_a$.

For example, $R_a$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more -$Q_2$-$T_2$.

For example, $R_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_2$-$T_2$.

For example, $R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.

For example, $R_6$ is 4 to 7-membered heterocycloalkyl optionally substituted with one or more -$Q_2$-$T_2$, and -$Q_2$-$T_2$ is oxo or $Q_2$ is a bond and $T_2$ is —$OR_c$, —$NR_cR_d$, —C(O)$R_c$, —C(O)O$R_c$, —S(O)$_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, $R_6$ is —$NR_aR_b$, —C(O)$R_a$, —C(O)O$R_a$, —C(O)$NR_aR_b$, —$NR_bC(O)R_a$, —$SR_a$, —S(O)$_2R_a$, or —S(O)$_2NR_aR_b$.

For example, each of $R_a$ and $R_b$, independently is H, $C_1$-$C_6$ alkyl or $C_3$-$C_8$ cycloalkyl optionally substituted with one or more -$Q_2$-$T_2$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more -$Q_2$-$T_2$ For example, -$Q_2$-$T_2$ is not H.

For example, -$Q_2$-$T_2$ is oxo.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_3$-$T_3$.

For example, $T_2$ is —$OR_c$, —$NR_cR_d$, —C(O)$R_c$, —C(O)O$R_c$, or —S(O)$_2R_c$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more -$Q_3$-$T_3$.

For example, each of $R_c$ and $R_d$, independently is H or $C_1$-$C_6$ alkyl optionally substituted with one or more -$Q_3$-$T_3$.

For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more -$Q_3$-$T_3$.

For example, $Q_2$ is a bond and $T_2$ is —OR, —$NR_cR_d$, —C(O)$R_c$, —C(O)O$R_c$, —S(O)$_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_e$, $COOR_e$, —S(O)$_2R_e$, —$NR_eR_f$ or —C(O)$NR_eR_f$.

For example, one of $R_d$ and $R_e$ is H.

For example, $Q_3$ is a bond or $C_1$-$C_3$ alkyl linker and $T_3$ is selected from the group consisting of $C_1$-$C_3$ alkyl, halo, $OR_e$, —S(O)$_2R_e$, —$NR_eR_f$, and —C(O)$NR_eR_f$.

For example, $Q_3$ is a bond or $C_1$-$C_3$ alkyl linker and $T_3$ is selected from the group consisting of $C_1$-$C_3$ alkyl, $OR_e$, —S(O)$_2R_e$, or —$NR_eR_f$.

For example, $R_e$ is H.

For example, $R_f$ is H.

For example, $R_7$ is not H.

For example, $R_7$ is —C(O)$R_g$.

For example, $R_7$ is —C(O)$R_g$, in which $R_g$ is $C_3$-$C_8$ cycloalkyl, or 4 to 7-membered heterocycloalkyl, $C_3$-$C_8$ cycloalkyl.

For example, $R_7$ is $C_6$-$C_{10}$ aryl substituted with one or more -$Q_5$-$T_5$.

For example, $R_7$ is phenyl optionally substituted with one or more -$Q_5$-$T_5$.

For example, $R_7$ is $C_1$-$C_6$ alkyl optionally substituted with one or more -$Q_5$-$T_5$.

For example, $R_7$ is $C_3$-$C_8$ cycloalkyl optionally substituted with one or more -$Q_5$-$T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_5$-$T_5$.

For example, $R_7$ is 8 to 14-membered heterocycloalkyl such as 1,4-dioxaspiro[4.5]decanyl (e.g., 1,4-dioxaspiro[4.5]decan-8-yl), 1,4-dioxa-8-azaspiro[4.5]decanyl (e.g., 1,4-dioxa-8-azaspiro[4.5]decan-8-yl), 1-oxaspiro[4.5]decanyl (e.g., 1-oxaspiro[4.5]decan-8-yl or 1-oxaspiro[4.5]decan-2-one-8-yl), 1-azaspiro[4.5]decanyl (e.g., 1-azaspiro[4.5]decan-8-yl or 1-azaspiro[4.5]decan-2-one-8-yl), 3'H-spiro[cyclohexane-1,1'-isobenzofuran]-yl (e.g., 3'H-spiro[cyclohexane-1,1'-isobenzofuran]-4-yl or 3'H-spiro[cyclohexane-1,1'-isobenzofuran]-3'-one-4-yl), 7'H-spiro[cyclohexane-1,5'-furo[3,4-b]pyridin]-yl (e.g., 7'H-spiro[cyclohexane-1,5'-furo[3,4-b]pyridin]-4-yl or 7'H-spiro[cyclohexane-1,5'-furo[3,4-b]pyridin]-7'-one-4-yl), or 3'H-spiro[cyclohexane-1,1'-furo[3,4-c]pyridin]-yl (e.g., 3'H-spiro[cyclohexane-1,1'-furo[3,4-c]pyridin]-4-yl or 3'H-spiro[cyclohexane-1,1'-furo[3,4-c]pyridin]-3'-one-4-yl), each optionally substituted with one or more -$Q_5$-$T_5$.

For example, $R_7$ is 5 to 6-membered heterocycloalkyl optionally substituted with one or more -$Q_5$-$T_5$.

For example, $R_7$ is isopropyl.

For example, $R_7$ is piperidinyl, tetrahydropyran, tetrahydro-2H-thiopyranyl, piperazinyl, cyclopentyl, cyclohexyl, pyrrolidinyl, or cycloheptyl, each optionally substituted with one or more -$Q_5$-$T_5$.

For example, $R_7$ is piperidinyl, tetrahydropyran, cyclopentyl, or cyclohexyl, each optionally substituted with one -$Q_5$-$T_5$ and $R_8$ is ethyl.

For example, $R_7$ is tetrahydropyran or

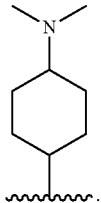 [SMILES: *C1CCC(N(C)C)CC1]

For example, $R_7$ is

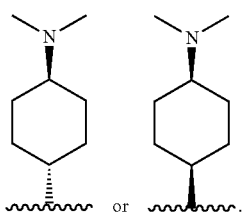

For example, $R_7$ is cyclopentyl or cyclohexyl, each optionally substituted with one -$Q_5$-$T_5$.

For example, $Q_5$ is NHC(O) and $T_5$ is $C_1$-$C_6$ alkyl or $C_1$-$C_6$ alkoxy.

For example, -$Q_5$-$T_5$ is oxo.

For example, $T_4$ is 4 to 7-membered heterocycloalkyl or $C_3$-$C_8$ cycloalkyl or $C_6$-$C_{10}$ aryl, and one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $R_7$ is cyclohexanonyl, e.g., cyclohexanon-4-yl.

For example, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_5$ is a bond and $T_5$ is $C_1$-$C_6$ alkyl, $C_3$-$C_8$ cycloalkyl, or 4 to 7-membered heterocycloalkyl.

For example, $Q_5$ is a bond and $T_5$ is 5- or 6-membered heteroaryl, amino, mono-$C_1$-$C_6$ alkylamino, di-$C_1$-$C_6$ alkylamino, $T_5$ being optionally substituted with one or more substituents selected from the group consisting of halo, hydroxyl, $C_1$-$C_6$ alkoxyl, or $C_3$-$C_8$ cycloalkyl.

For example, $Q_5$ is CO, S(O)$_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5$ is $C_1$-$C_3$ alkyl linker and $T_5$ is H or $C_6$-$C_{10}$ aryl.

For example, $Q_5$ is $C_1$-$C_3$ alkyl linker and $T_5$ is $C_3$-$C_8$ cycloalkyl, 4 to 7-membered heterocycloalkyl, or S(O)$_q R_q$.

For example, $R_6$ is halo (e.g., fluorine, chlorine, bromine, and iodine) and Z is S(O)$_a R_7$, in which a is 0, 1, or 2 and $R_7$ is $C_1$-$C_6$ alkyl (e.g., methyl, ethyl, n-propyl, i-propyl, butyl, or t-butyl), $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_6$ is halo (e.g., fluorine, chlorine, bromine, and iodine) and Z is OR$_7$ in which $R_7$ is 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_{12}$ is H, methyl, ethyl, ethenyl, or halo.

For example, $R_{12}$ is methyl.

For example, $R_{12}$ is ethyl or propenyl.

For example, $R_{12}$ is methoxyl.

For example, $R_{12}$ is ethenyl.

For example, $R_8$ is H, methyl, ethyl, or ethenyl.

For example, $R_8$ is methyl.

For example, $R_8$ is ethyl.

For example, $R_8$ is propyl.

For example, $R_8$ is ethenyl or propenyl.

For example, $R_8$ is $C_1$-$C_6$ alkyl substituted with one or more substituents selected from the group consisting of halo (e.g., F, Cl, or Br), hydroxyl, or $C_1$-$C_6$ alkoxyl.

For example, $R_8$ is 4 to 7-membered optionally substituted heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like).

For example, $R_8$ is piperidinyl.

For example, $R_8$ is 4 to 7-membered optionally substituted heterocycloalkyl and $R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl or 4 to 7-membered heterocycloalkyl.

For example, Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, morpholinyl, 1,4-dioxa-8-azaspiro[4.5]decanyl, and the like) or $C_3$-$C_8$ cycloalkyl, each optionally substituted with one or more -$Q_6$-$T_6$.

For example, the ring formed by $R_7$ and $R_8$ is selected from the group consisting of azetidinyl, pyrrolidinyl, piperidinyl, morpholinyl, piperazinyl, 1,4-dioxa-8-azaspiro[4.5]decanyl, and cyclohexenyl, each optionally substituted with one -$Q_6$-$T_6$.

For example, Z is 1,4-dioxa-8-azaspiro[4.5]decan-8-yl, pyrrolidine-2,5-dione-1-yl, or piperidine-2,6-dione-1-yl.

For example, one or more -$Q_6$-$T_6$ is oxo.

For example, $T_6$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_6$ is a bond and $T_6$ is $C_1$-$C_6$ alkyl, $C_3$-$C_8$ cycloalkyl, or 4 to 7-membered heterocycloalkyl.

For example, $Q_6$ is CO, $S(O)_2$, or NHC(O); and $T_6$ is $C_1$-$C_6$ alkyl, $C_1$-$C_6$ alkoxyl, $C_3$-$C_8$ cycloalkyl, or 4 to 7-membered heterocycloalkyl.

For example, $T_6$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_5$ cycloalkyl.

For example, $Q_6$ is $C_1$-$C_3$ alkyl linker and $T_6$ is H or $C_6$-$C_{10}$ aryl.

For example, $Q_6$ is $C_1$-$C_3$ alkyl linker and $T_6$ is $C_3$-$C_8$ cycloalkyl, 4 to 7-membered heterocycloalkyl, or $S(O)_pR_p$.

For example, each of $R_p$ and $R_q$, independently, is $C_1$-$C_6$ alkyl.

For example, $R_6$ is —$S(O)_bR_a$ or azido, in which b is 0, 1, or 2 and $R_a$ is $C_1$-$C_6$ alkyl or $C_3$-$C_8$ cycloalkyl; and Z is $NR_7R_8$, in which $R_7$ is $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like), each optionally substituted with one or more -$Q_5$-$T_5$; and $R_8$ is H or $C_1$-$C_6$ alkyl (e.g., methyl, ethyl, n-propyl, i-propyl, butyl, or t-butyl).

For example, $R_6$ is halo (e.g., fluorine, chlorine, bromine, and iodine) and Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 2-oxa-6-azaspiro[3.3]heptanyl, 2,6-diazaspiro[3.3]heptanyl, 1,4-dioxa-8-azaspiro[4.5]decanyl, 1,4-dioxa-8-azaspiro[4.5]decan-8-yl, pyrrolidine-2,5-dione-1-yl, piperidine-2,6-dione-1-yl, and the like) or $C_3$-$C_8$ cycloalkyl, each optionally substituted with one or more -$Q_6$-$T_6$.

For example, each of $R_5$, $R_9$, and $R_{10}$ is H.

For example, n is 0.

For example, n is 1.

For example, n is 2.

Another subset of the compounds of Formula (I) includes those of Formula (IIIa), (IIIb), or (IIIc):

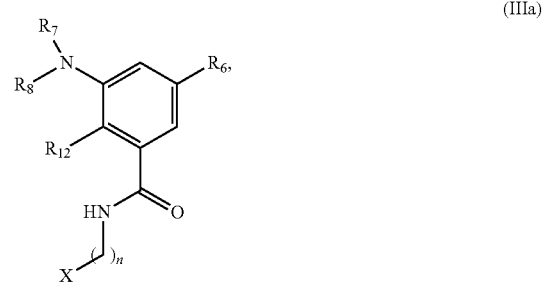

(IIIa)

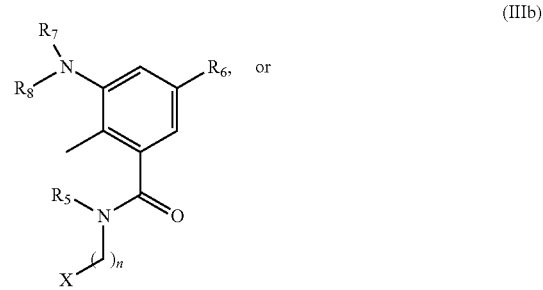

(IIIb)

or

-continued

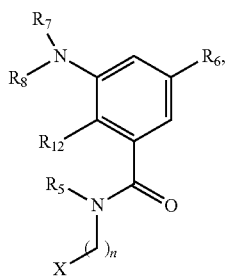

(IIIc)

or pharmaceutically acceptable salts thereof, wherein n is 0, 1, or 2; and X, $R_5$, $R_6$, $R_7$, $R_8$, and $R_{12}$ are as defined herein for Formula (I).

Another subset of the compounds of Formula (I) includes those of Formula (IV):

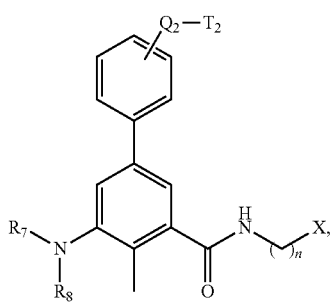

(IV)

or pharmaceutically acceptable salts thereof, wherein n is 0, 1, or 2; $Q_2$ is a bond or methyl linker, $T_2$ is H, halo, —$OR_c$, —$NR_cR_d$, or —$S(O)_2NR_cR_d$; and X, $R_c$, $R_d$, $R_7$, and $R_8$ are defined herein for Formula (I).

Another subset of the compounds of Formula (I) includes those of Formula (IVa):

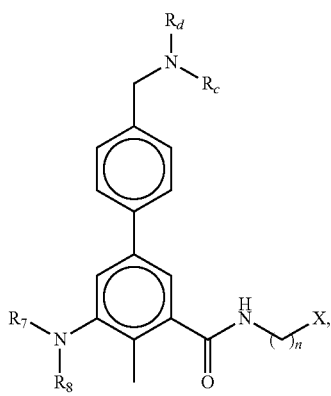

(IVa)

or pharmaceutically acceptable salts thereof, wherein n is 0, 1, or 2; and X, $R_c$, $R_d$, $R_7$, and $R_8$ are defined herein for Formula (I).

Yet another subset of the compounds of Formula (I) includes those of Formula (V):

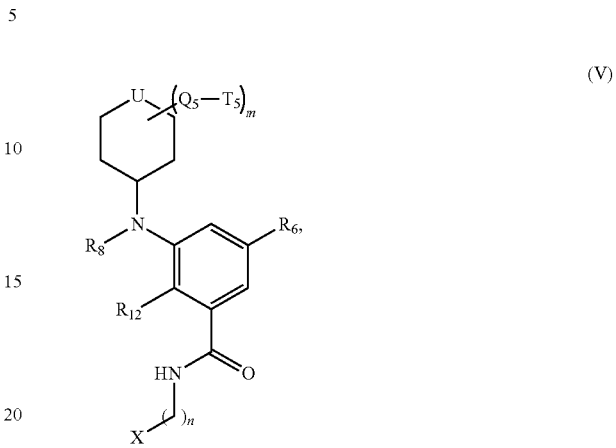

(V)

or pharmaceutically acceptable salts thereof, wherein m is 0, 1, or 2; n is 0, 1, or 2; U is O, S, N-$Q_5$-$T_5$, or CH-$Q_5$-$T_5$; $R^{12}$ is Cl, Br, or methyl; and X, $R_6$, $R_8$, $Q_5$, and $T_5$ are defined herein for Formula (I).

In addition to the above-described features of the compounds of this invention, where applicable, the compounds of each of Formulae (IIIa), (IIIb), (IIIc), (IV), (IVa), and (V) can include one or more of the following features:

For example, $Q_5$ is a bond and $T_5$ is H, $C_1$-$C_6$ alkyl, $C_3$-$C_8$ cycloalkyl, 4 to 12-membered heterocycloalkyl, 5- or 6-membered heteroaryl, amino, mono-$C_1$-$C_6$ alkylamino, or di-$C_1$-$C_6$ alkylamino, $T_5$ being optionally substituted with one or more substituents selected from the group consisting of halo, hydroxyl, $C_1$-$C_6$ alkoxyl, or $C_3$-$C_8$ cycloalkyl.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 12-membered heterocycloalkyl.

For example, $Q_5$ is $C_1$-$C_3$ alkyl linker and $T_5$ is H or $C_6$-$C_{10}$ aryl.

For example, $Q_5$ is $C_1$-$C_3$ alkyl linker and $T_5$ is $C_3$-$C_8$ cycloalkyl, 4 to 12-membered heterocycloalkyl, or $S(O)_qR_q$.

For example, $Q_5$ is NHC(O) and $T_5$ is $C_1$-$C_6$ alkyl or $C_1$-$C_6$ alkoxy.

For example, one or more -$Q_5$-$T_5$ are oxo.

For example, U is CH-$Q_5$-$T_5$ and m is 0.

For example, one or more -$Q_6$-$T_6$ are oxo.

For example, $Q_6$ is a bond or C(O) and $T_6$ is $C_1$-$C_6$ alkyl or $C_1$-$C_6$ alkoxy.

Still another subset of the compounds of Formula (I) includes those of Formula (VI):

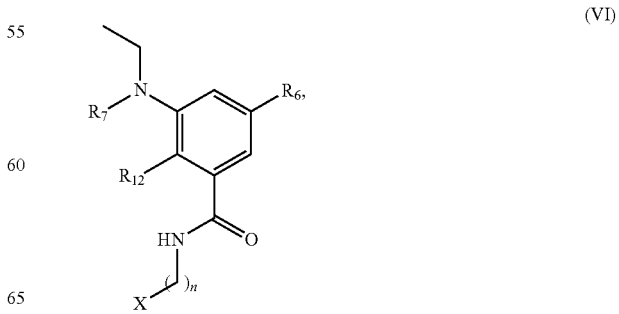

(VI)

or pharmaceutically acceptable salts thereof, wherein n is 0, 1, or 2; $R_7$ is $-Q_4-T_4$, wherein $Q_4$ is a bond or methyl linker, $T_4$ is optionally substituted $C_3$-$C_8$ cycloalkyl or optionally substituted 4- to 14-membered heterocycloalkyl; and X, $R_6$, and $R_{12}$ are defined herein for Formula (I).

For example, $T_4$ is

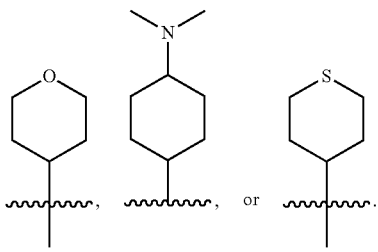

For example, $T_4$ is

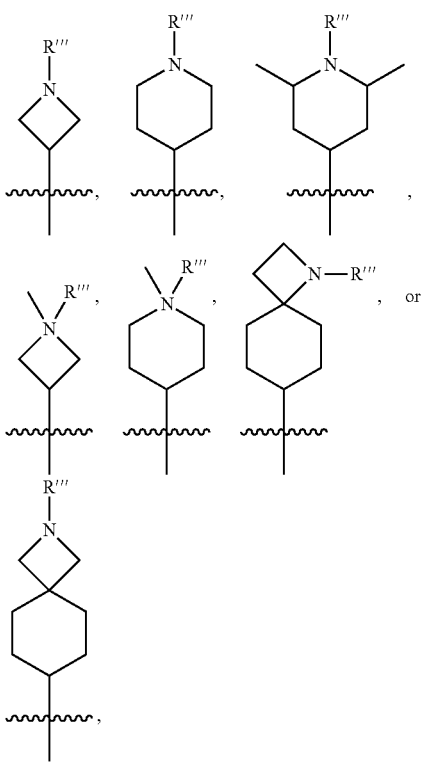

in which R''' is $T_5$, —C(O)$T_5$, or S(O)$_2T_5$, $T_5$ being as defined herein for Formula (I).

For example, the compound of Formula (VI) include those of Formula (VIa):

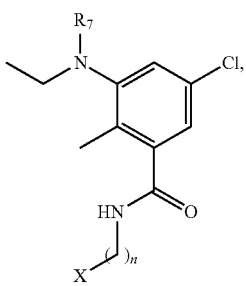

(VIa)

wherein $R_7$ is piperidinyl, tetrahydropyran, cyclopentyl, or cyclohexyl, each optionally substituted with one -$Q_5$-$T_5$; n is 1 or 2; and X is

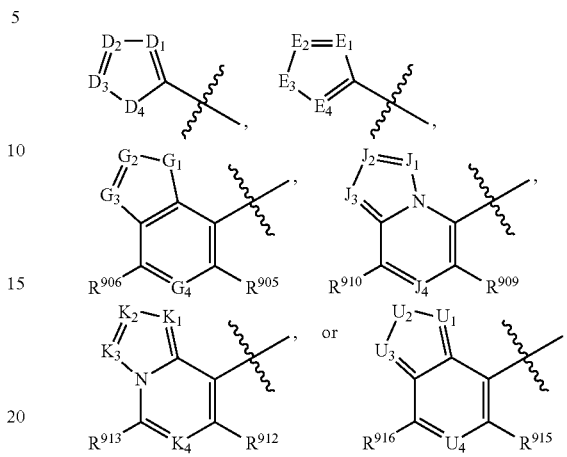

in which each of $D_1$, $D_2$, and $D_3$, independently, is $CR^{901}$ or N, provided that at least one of $D_1$, $D_2$, and $D_3$ is N; $D_4$ is O, S, or $NR^{902}$; each of $E_1$, $E_2$, and $E_4$, independently, is $CR^{903}$ or N, provided that at least one of $E_1$, $E_2$, and $E_4$ is N; $E_3$ is O, S, or $NR^{904}$; $G_1$ is O, S, or $NR^{907}$; each of $G_2$, $G_3$, and $G_4$, independently, is N or $CR^{908}$, provided that at least one of $G_2$, $G_3$, and $G_4$ is N; each of $J_1$, $J_2$, $J_3$, and $J_4$, independently, is N or $CR^{911}$, provided that at least one of $J_1$, $J_2$, $J_3$, and $J_4$ is N; each of $K_1$, $K_2$, $K_3$, and $K_4$, independently, is N or $CR^{914}$, provided that at least one of $K_1$, $K_2$, $K_3$, and $K_4$ is N; each of $U_1$, $U_3$, and $U_4$, independently, is N or $CR^{917}$, provided that at least one of $U_1$, $U_3$, and $U_4$ is N; $U_2$ is O, S, or $NR^{918}$; and each of $R^{901}$, $R^{902}$, $R^{903}$, $R^{904}$, $R^{905}$, $R^{906}$, $R^{907}$, $R^{908}$, $R^{909}$, $R^{910}$, $R^{911}$, $R^{912}$, $R^{913}$, $R^{914}$, $R^{915}$, $R^{916}$, $R^{917}$ and $R^{918}$, independently, is $Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_{r'}$, —$C(O)R_n$, —$C(O)OR_n$, —$C(O)NR_nR_{r'}$, —$S(O)_2R_n$, —$S(O)_2NR_nR_{r'}$, or $R_{S9}$, in which each of $R_n$ and $R_{r'}$ independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_{r'}$ together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_{r'}$ is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_s$, $COOR_s$, —$S(O)_2R_s$, —$NR_sR_{t'}$ and —$C(O)NR_sR_{t'}$, each of $R_s$ and $R_{t'}$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, the compounds of Formula (VI) include those of Formula (VIb):

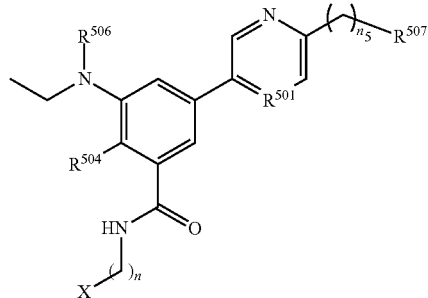

(VIb)

or a pharmaceutically acceptable salt thereof; wherein n is 0, 1, or 2;

$n_5$ is 0, 1, or 2;

$R^{501}$ is C(H) or N;

$R_{504}$ is $C_{1-4}$ alkyl;

$R_{506}$ is cyclohexyl substituted by $N(C_{1-4}$ alkyl$)_2$ or piperidine substituted by 1, 2, or 3 $C_{1-4}$ alkyl groups;

$R^{507}$ is morpholine, piperazine, piperidine, diazepane, pyrrolidine, azetidine, O—$C_{1-6}$ alkyl, or O-heterocycle, wherein the heterocycle is a 4-7 membered heterocycle containing an oxygen or nitrogen, or both, and wherein the nitrogen can optionally be substituted with $C_{1-3}$ alkyl; wherein the piperazine, piperidine, diazepane, pyrrolidine or azetidine groups can be optionally further substituted with OH, $C_{1-6}$ alkyl, or O—$C_{1-3}$ alkyl; and X is as defined herein for Formula (I).

In certain compounds of Formula (VIb), $R^{501}$ is C(H), and $R^{507}$ is piperidine; diazepane; pyrrolidine; azetidine; O—$C_{1-6}$ alkyl; or O-heterocycle, wherein the heterocycle is a 4-7 membered heterocycle containing an oxygen or nitrogen, or both, and wherein the nitrogen can optionally be substituted with $C_{1-3}$ alkyl; wherein the piperidine, diazepane, pyrrolidine or azetidine groups can be optionally further substituted with OH, $C_{1-6}$ alkyl, or O—$C_{1-3}$ alkyl.

In certain compounds of Formula (VIb), $R^{501}$ is C(H) and $R^{507}$ is piperidine, diazepane, pyrrolidine, azetidine or O—$C_{1-6}$ alkyl, wherein the piperidine, diazepane, pyrrolidine or azetidine groups can be optionally further substituted with OH or $C_{1-6}$ alkyl.

In certain compounds of Formula (VIb), $R^{501}$ is C(H), $R^{507}$ is piperazine optionally further substituted with $C_{1-6}$ alkyl, and $R^{506}$ is piperidine substituted by 1, 2, or 3 $C_{1-4}$ alkyl groups.

In certain compounds of Formula (VIb), $R^{501}$ is N, and $R^{507}$ is morpholine, piperidine, piperazine, diazepane, pyrrolidine, azetidine or O—$C_{1-6}$ alkyl, wherein the piperidine, piperazine, diazepane, pyrrolidine or azetidine groups can be optionally further substituted with OH or $C_{1-6}$ alkyl.

In certain compounds of Formula (VIb), $R^{504}$ is methyl.

In certain compounds of Formula (VIb), $R^{506}$ is

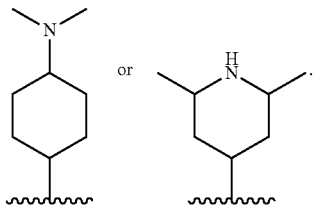

In certain compounds of Formula (VIb), $R^{506}$ is

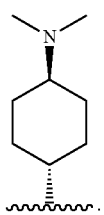 [SMILES: *[C@H]1CC[C@H](N(C)C)CC1]

In certain compounds of Formula (VIb), when $R^{501}$ is C(H), $R^{507}$ is piperidine or diazepane, which are substituted with OH or $C_{1-6}$ alkyl, or when $R^{501}$ is N, $R^{507}$ is piperidine, piperazine, or diazepane, which are optionally further substituted with OH or $C_{1-6}$ alkyl.

In certain compounds of Formula (VIb), when $R^{501}$ is C(H), $R^{507}$ is piperidine substituted with $C_{1-6}$ alkyl, or when $R^{501}$ is N, $R^{507}$ is piperidine substituted with OH or piperazine substituted with $C_{1-6}$ alkyl.

In certain compounds of Formula (VIb), when $R^{501}$ is N, $R^{507}$ is unsubstituted piperazine.

In certain compounds of Formula (VIb), $n_5$ is 0 or 1.

In certain compounds of Formula (VIb), when $R^{501}$ is C(H) or N, $R^{507}$ is O—$C_{1-6}$ alkyl or O-heterocycle, and $n_5$ is 1.

In certain compounds of Formula (VIb), when $R^{501}$ is C(H), $R^{507}$ is unsubstituted piperazine and $R^{506}$ is piperidine substituted by 1, 2, or 3 $C_{1-4}$ alkyl groups.

In certain compounds of Formula (VIb), X is imidazol-2-yl, imidazol-4-yl, triazol-3-yl, 3H-imidazo[4,5-c]pyridin-7-yl, 1H-benzo[d]imidazol-4-yl, 1H-indazol-7-yl, isoxazol-3-yl, thiazol-2-yl, 1H-pyrazolo[4,3-c]pyridin-7-yl, imidazo[1,2-a]pyridin-8-yl, imidazo[1,2-c]pyrimidin-8-yl, 1,4,6,7-tetrahydropyrano[4,3-c]pyrazol-7-yl, 1,4,6,7-tetrahydropyrano[3,4-]imidazol-7-yl, or 4,5,6,7-tetrahydro-1H-benzo[d]imidazol-4-yl.

For example, the compounds of Formula (VI) include those of Formula (VIc):

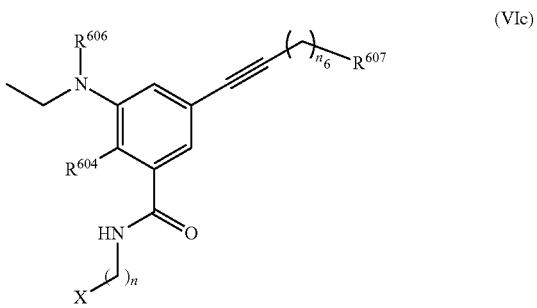

(VIc)

or a pharmaceutically acceptable salt thereof; wherein n is 0, 1, or 2;

$n_6$ is 0, 1 or 2;

$R^{604}$ is $C_{1-4}$ alkyl;

$R^{606}$ is cyclohexyl substituted by $N(C_{1-4}$ alkyl$)_2$, tetrahydropyranyl, or piperidine substituted by 1, 2, or 3 $C_{1-4}$ alkyl groups;

$R^{607}$ is morpholine, piperidine, piperazine, pyrrolidine, diazepane, oxetane, azetidine or O—$C_{1-6}$ alkyl, wherein the piperidine, diazepane, oxetane or azetidine groups can be optionally further substituted with one or more $C_{1-6}$ alkyl, $C_{1-6}$ haloalkyl, $C_{3-8}$ cycloalkyl, or 4 to 6-membered heterocycloalkyl; and X is as defined herein for Formula (I).

In certain compounds of Formula (VIc), $R^{604}$ is methyl.

In certain compounds of Formula (IVb), $R^{606}$ is

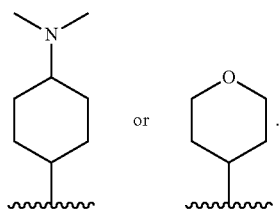

In certain compounds of Formula (VIc), $R^{606}$ is

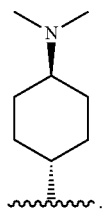

In certain compounds of Formula (VIc), $R^{607}$ is piperidine or oxetane, each of which is substituted with $C_{1-6}$ alkyl.

In certain compounds of Formula (VIc), $R^{607}$ is piperidine substituted with $CH_2CF_3$, cyclopropyl, cyclobutyl, cyclohexyl, or oxetane.

In certain compounds of Formula (VIc), $n_6$ is 0 or 1.

In certain compounds of Formula (VIc), n is 0 or 1.

In certain compounds of Formula (VIc), X is

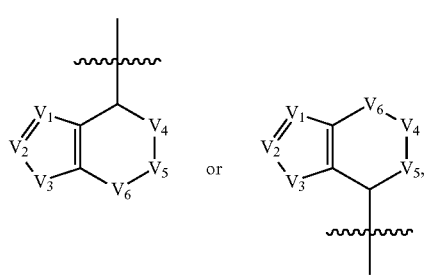

In the formulae, each of $V_1$ and $V_2$, independently, is N or $CR^{919}$, provided that at least one of $V_1$ and $V_2$ is N. $V_3$ is O, S, or $NR^{920}$. Each of $V_4$, $V_5$, and $V_6$ is O, S, or $NR^{921}$, or $cR^{922}R^{923}$. Each of $R^{919}$, $R^{920}$, $R^{921}$, $R^{922}$, and $R^{923}$, independently, is -$Q_7$-$T_7$, wherein $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_r$, —$S(O)_2R_n$, —$S(O)_2NR_nR_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_s$, $COOR_s$, —$S(O)_2R_s$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl. In certain compounds, X is

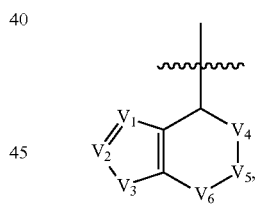

in which $V_1$ is N, $V_2$ is $CR^{919}$, $V_3$ is $NR^{920}$, and each of $V_4$, $V_5$, and $V_6$ is $CR^{922}R^{923}$. In other compounds, X is

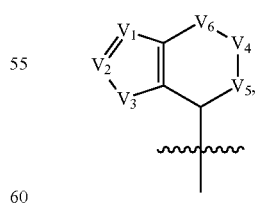

in which $V_1$ is $CR^{919}$, $V_2$ is N, $V_3$ is $NR^{920}$, each of $V_5$ and $V_6$ is $CR^{922}R^{923}$, and $V_4$ is O; or $V_1$ is N, $V_2$ is $CR^{919}$, $V_3$ is $NR^{920}$, each of $V_4$ and $V_6$ is $CR^{922}R^{923}$, and $V_5$ is O.

Representative compounds of the present invention include compounds listed in Tables 1-2.

TABLE 1
| Compound Number | Structure |
|---|---|
| 1 | 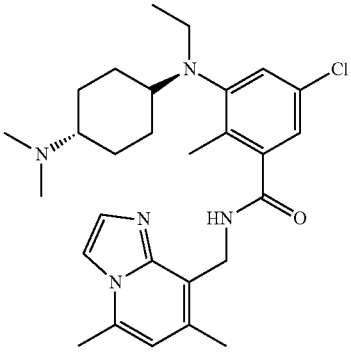 |
| 2 | 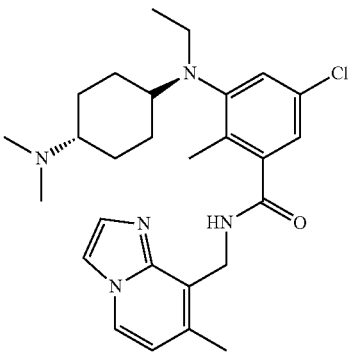 |
| 3 | 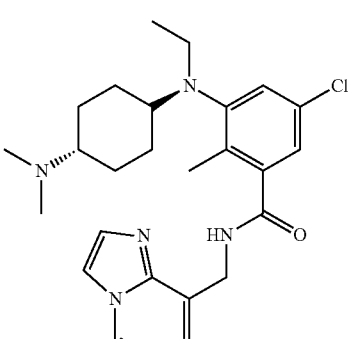 |
| 4 | 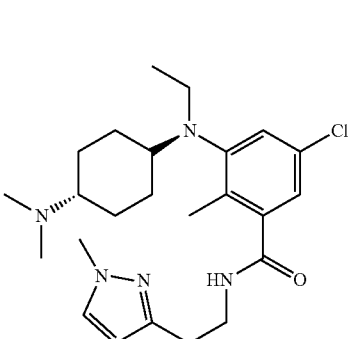 |
TABLE 1-continued
| Compound Number | Structure |
|---|---|
| 5 | 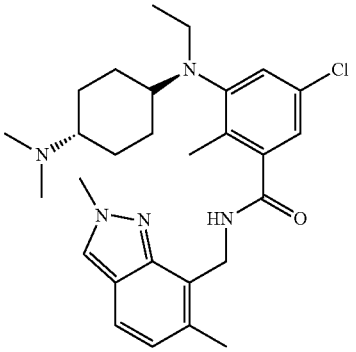 |
| 6 | 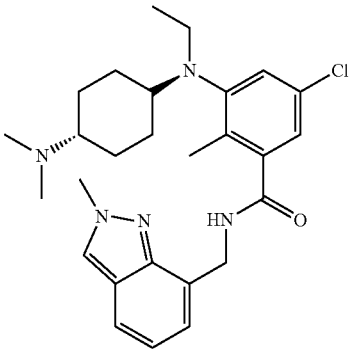 |
| 7 | 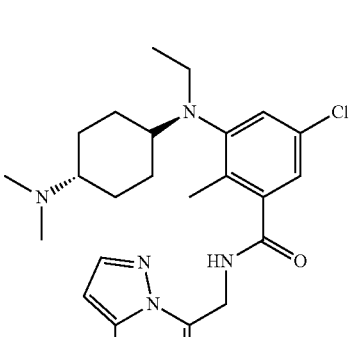 |
| 8 | 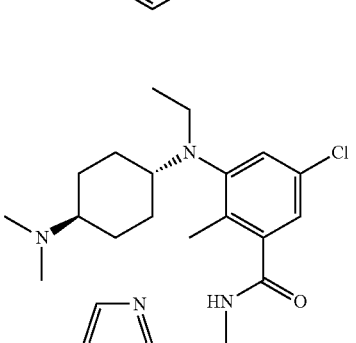 |

TABLE 1-continued
| Compound Number | Structure |
|---|---|
| 9 | 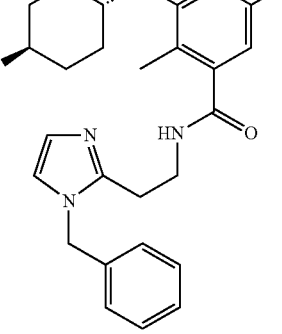 |
| 10 | 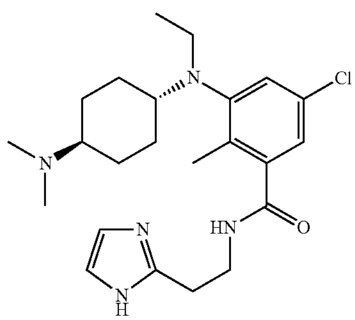 [SMILES: CCN(c1cc(Cl)cc(C(=O)NCCc2ncc[nH]2)c1C)[C@H]1CC[C@H](N(C)C)CC1] |
| 11 | 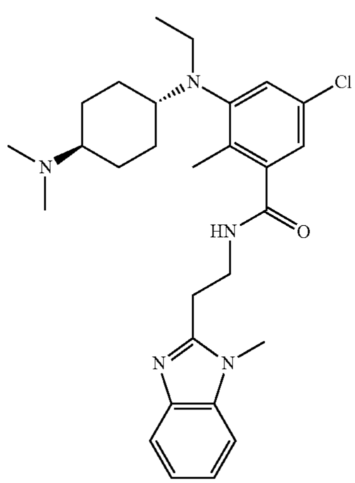 [SMILES: CCN(c1cc(Cl)cc(C(=O)NCCc2nc3ccccc3n2C)c1C)[C@H]1CC[C@H](N(C)C)CC1] |
| 12 | 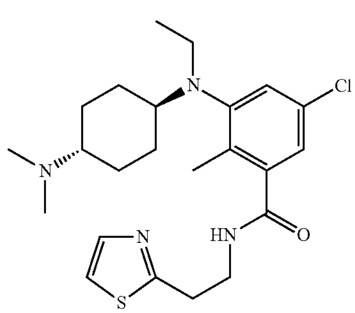 [SMILES: CCN(c1cc(Cl)cc(C(=O)NCCc2nccs2)c1C)[C@H]1CC[C@H](N(C)C)CC1] |
TABLE 1-continued
| Compound Number | Structure |
|---|---|
| 13 | 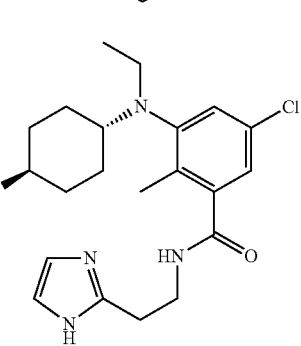 |
| 14 | 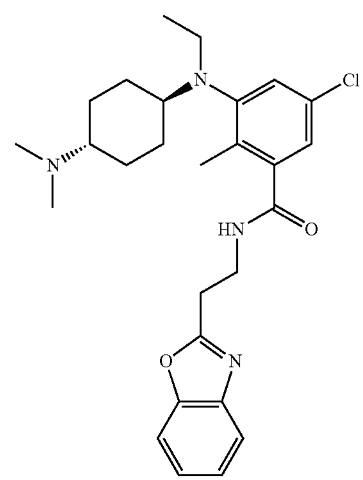 [SMILES: CCN(c1cc(Cl)cc(C(=O)NCCc2nc3ccccc3o2)c1C)[C@H]1CC[C@H](N(C)C)CC1] |
| 15 | 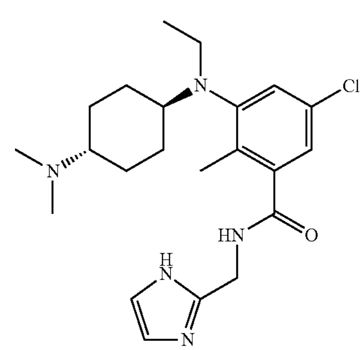 [SMILES: CCN(c1cc(Cl)cc(C(=O)NCc2ncc[nH]2)c1C)[C@H]1CC[C@H](N(C)C)CC1] |

TABLE 1-continued

| Compound Number | Structure |
|---|---|
| 16 | (structure) |
| 17 | (structure) |
| 18 | (structure) |
| 19 | (structure) |
| 20 | (structure) |
| 21 | (structure) |
| 22 | (structure) |
| 23 | (structure) |

TABLE 1-continued

| Compound Number | Structure |
|---|---|
| 24 | (structure) |
| 25 | (structure) |
| 26 | (structure) |
| 27 | (structure) |
| 28 | (structure) |
| 29 | (structure) |
| 30 | (structure) |
| 31 | (structure) |

TABLE 2

| Cpd No. | Structure |
|---|---|
| 32 | (structure) |

TABLE 2-continued

| Cpd No. | Structure |
|---|---|
| 33 | 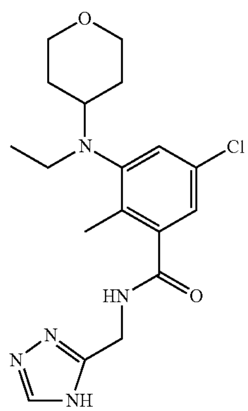 [SMILES: CCN(c1cc(Cl)cc(C(=O)NCc2nnc[nH]2)c1C)C1CCOCC1] |
| 34 | 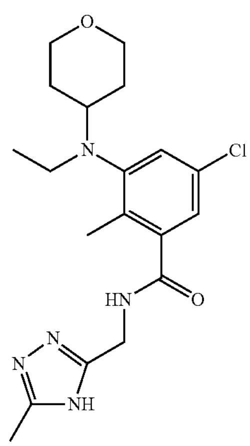 [SMILES: CCN(c1cc(Cl)cc(C(=O)NCc2nnc(C)[nH]2)c1C)C1CCOCC1] |
| 35 | 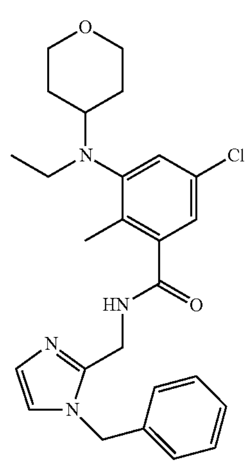 [SMILES: CCN(c1cc(Cl)cc(C(=O)NCc2nccn2Cc2ccccc2)c1C)C1CCOCC1] |
| 36 | 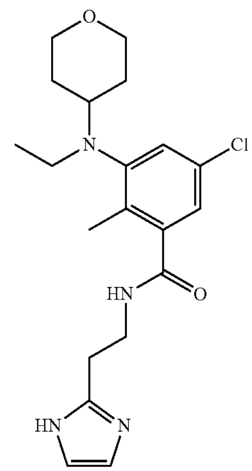 [SMILES: CCN(c1cc(Cl)cc(C(=O)NCCc2ncc[nH]2)c1C)C1CCOCC1] |
| 37 | 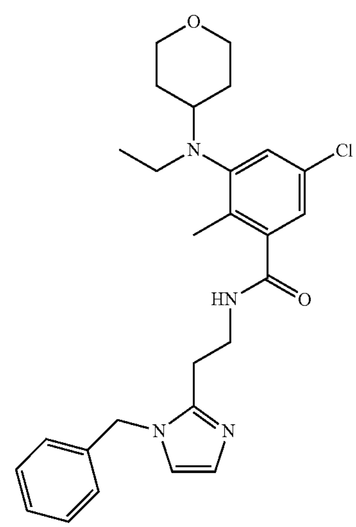 [SMILES: CCN(c1cc(Cl)cc(C(=O)NCCc2nccn2Cc2ccccc2)c1C)C1CCOCC1] |
| 38 | 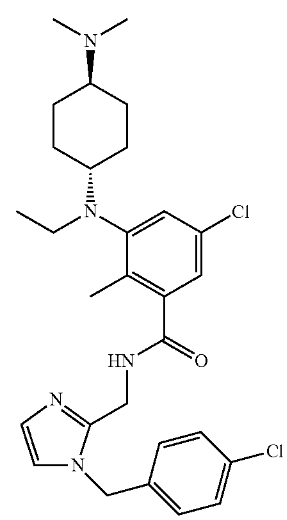 [SMILES: CCN(c1cc(Cl)cc(C(=O)NCc2nccn2Cc2ccc(Cl)cc2)c1C)[C@H]1CC[C@H](N(C)C)CC1] |

TABLE 2-continued
| Cpd No. | Structure |
|---|---|
| 39 | 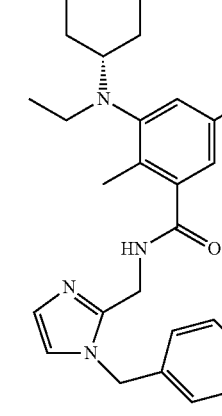 |
| 40 | 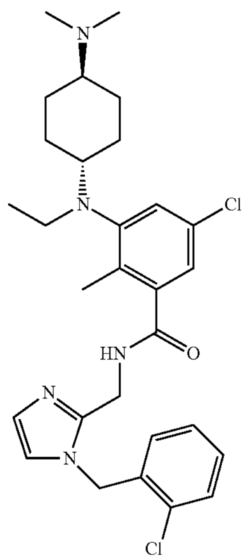 [SMILES: CCN(c1cc(Cl)cc(C(=O)NCc2nccn2Cc2ccccc2Cl)c1C)[C@H]1CC[C@H](N(C)C)CC1] |
| 41 | 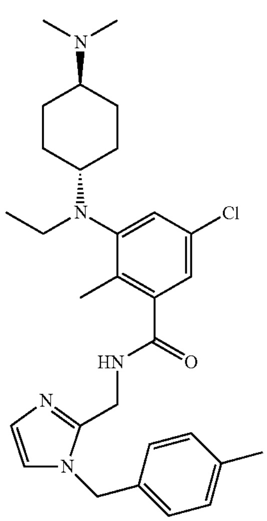 [SMILES: CCN(c1cc(Cl)cc(C(=O)NCc2nccn2Cc2ccc(C)cc2)c1C)[C@H]1CC[C@H](N(C)C)CC1] |
| 42 | 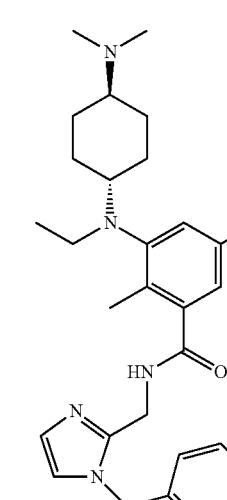 |
| 43 | 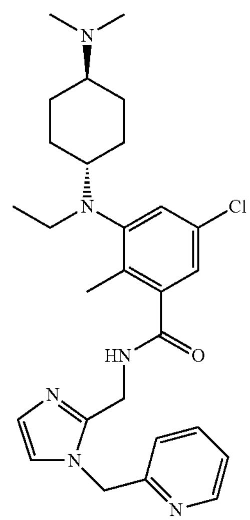 [SMILES: CCN(c1cc(Cl)cc(C(=O)NCc2nccn2Cc2ccccn2)c1C)[C@H]1CC[C@H](N(C)C)CC1] |
| 44 | 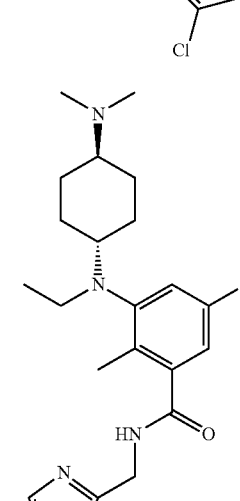 |

TABLE 2-continued

| Cpd No. | Structure |
|---|---|
| 45 | (structure) |
| 46 | (structure) |
| 47 | (structure) |
| 48 | (structure) |
| 49 | (structure) |
| 50 | (structure) |

TABLE 2-continued
| Cpd No. | Structure |
|---|---|
| 51 | 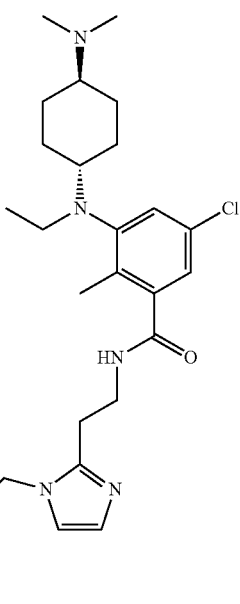 |
| 52 | 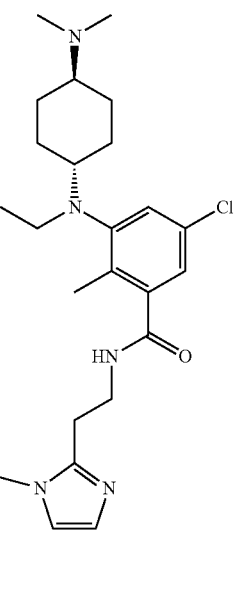 |
TABLE 2-continued
| Cpd No. | Structure |
|---|---|
| 53 | 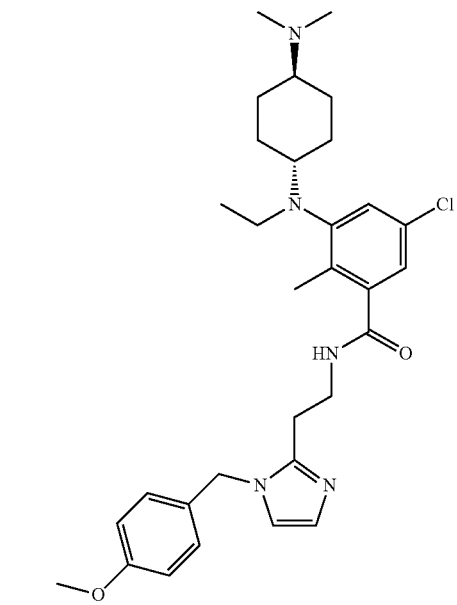 [SMILES: CCN(c1cc(Cl)cc(C(=O)NCCc2nccn2Cc2ccc(OC)cc2)c1C)[C@H]1CC[C@H](N(C)C)CC1] |
| 54 | 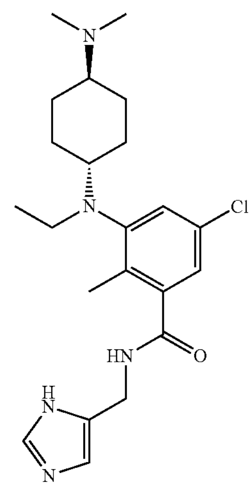 [SMILES: CCN(c1cc(Cl)cc(C(=O)NCc2cnc[nH]2)c1C)[C@H]1CC[C@H](N(C)C)CC1] |
| 55 | 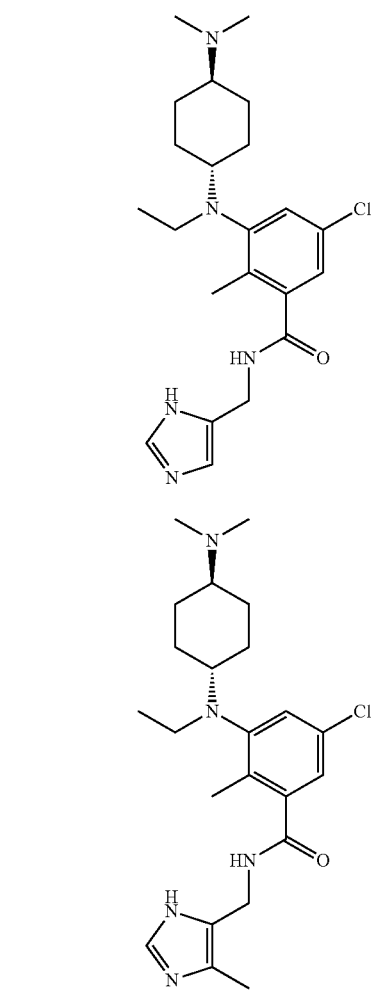 |

TABLE 2-continued

| Cpd No. | Structure |
|---|---|
| 56 | 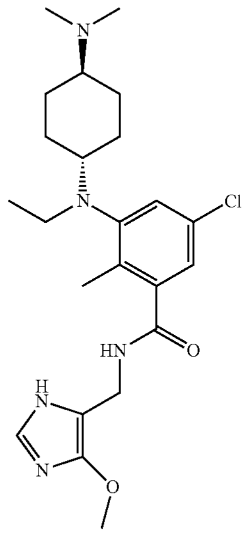 [SMILES: CCN(c1cc(Cl)cc(C(=O)NCc2[nH]cnc2OC)c1C)[C@H]1CC[C@H](N(C)C)CC1] |
| 57 | 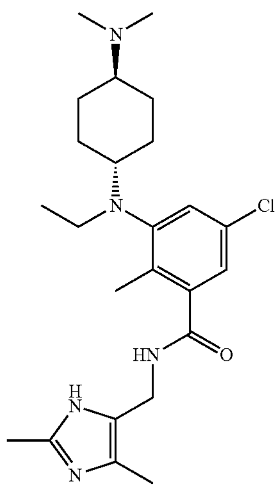 [SMILES: CCN(c1cc(Cl)cc(C(=O)NCc2[nH]c(C)nc2C)c1C)[C@H]1CC[C@H](N(C)C)CC1] |
| 58 | 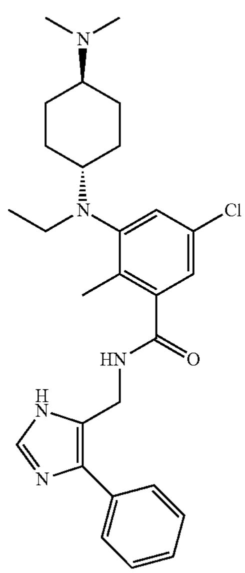 [SMILES: CCN(c1cc(Cl)cc(C(=O)NCc2[nH]cnc2-c2ccccc2)c1C)[C@H]1CC[C@H](N(C)C)CC1] |
| 59 | 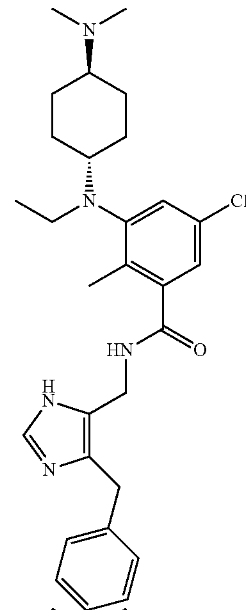 [SMILES: CCN(c1cc(Cl)cc(C(=O)NCc2[nH]cnc2Cc2ccccc2)c1C)[C@H]1CC[C@H](N(C)C)CC1] |

TABLE 2-continued
| Cpd No. | Structure |
|---|---|
| 62 | 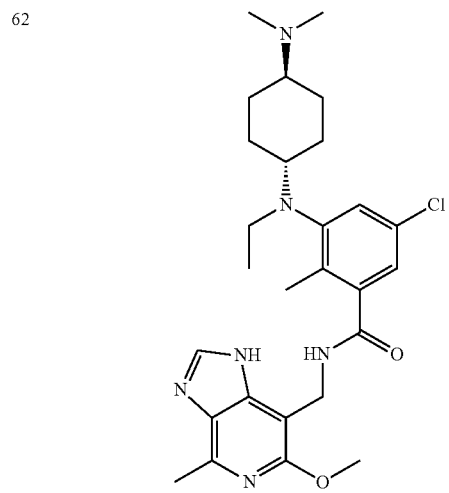 |
| 63 | 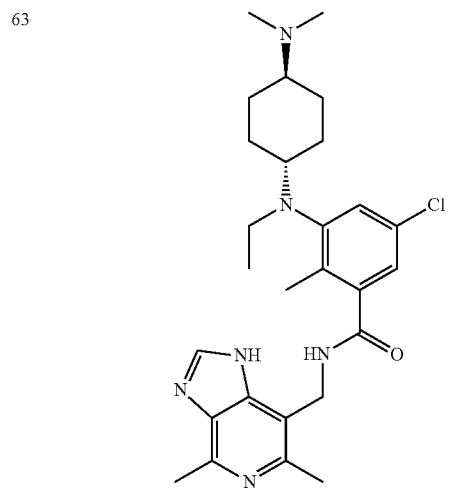 |
| 64 | 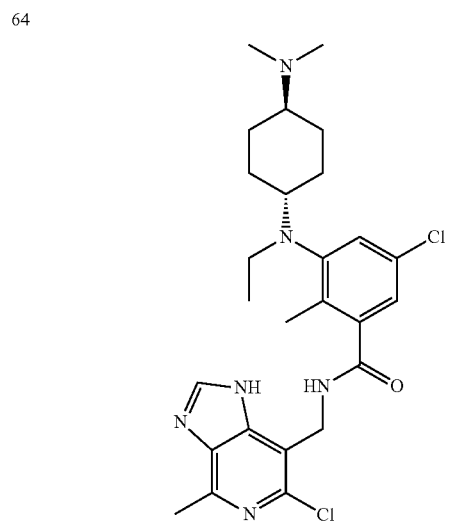 |
TABLE 2-continued
| Cpd No. | Structure |
|---|---|
| 65 | 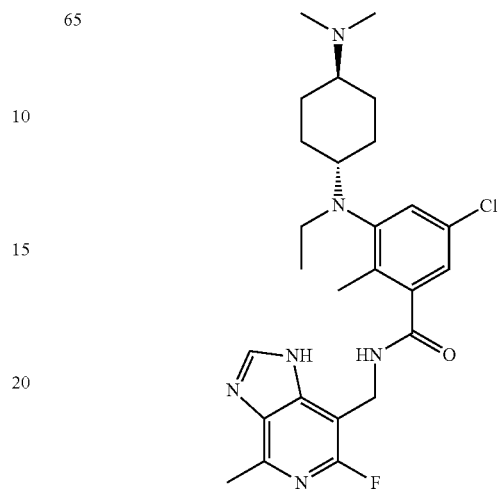 |
| 66 | 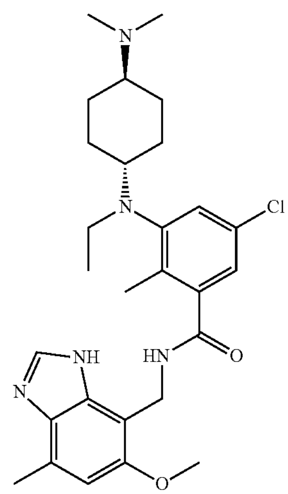 [SMILES: CCN(c1cc(Cl)cc(C(=O)NCc2c(OC)cc(C)c3nc[nH]c23)c1C)[C@H]1CC[C@H](N(C)C)CC1] |
| 67 | 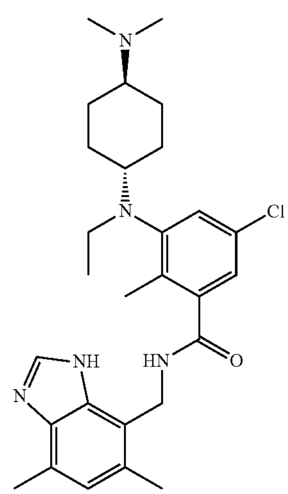 [SMILES: CCN(c1cc(Cl)cc(C(=O)NCc2c(C)cc(C)c3nc[nH]c23)c1C)[C@H]1CC[C@H](N(C)C)CC1] |

TABLE 2-continued
| Cpd No. | Structure |
|---|---|
| 68 | 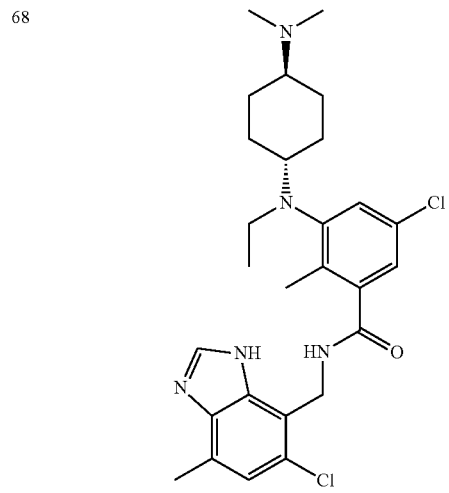 |
| 69 | 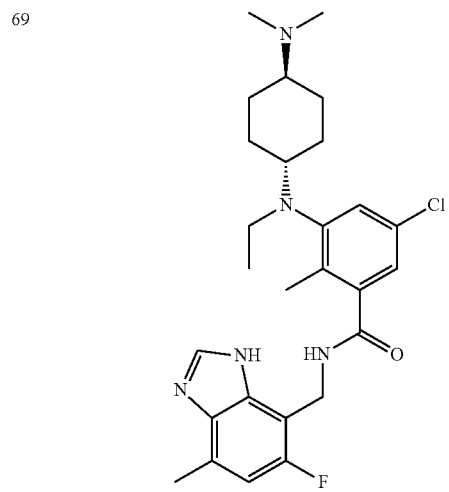 |
| 70 | 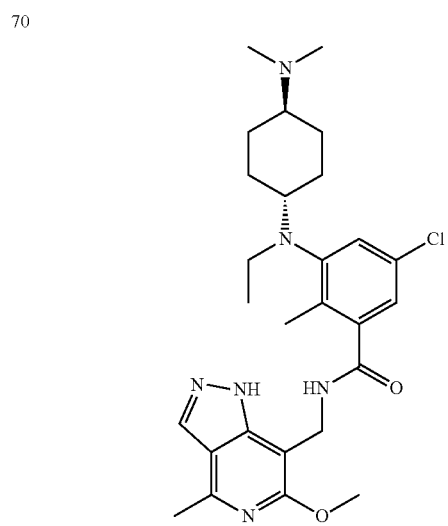 |
TABLE 2-continued
| Cpd No. | Structure |
|---|---|
| 71 | 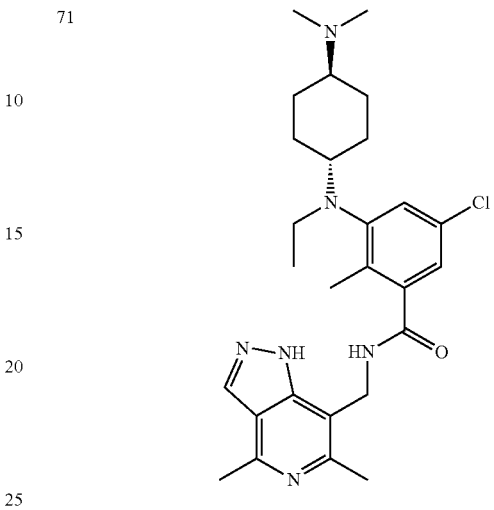 |
| 72 | 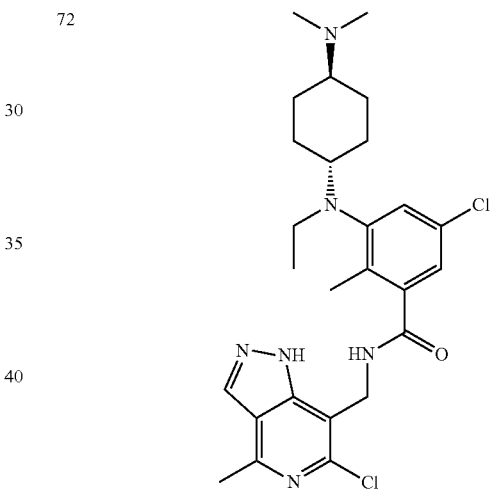 |
| 73 | 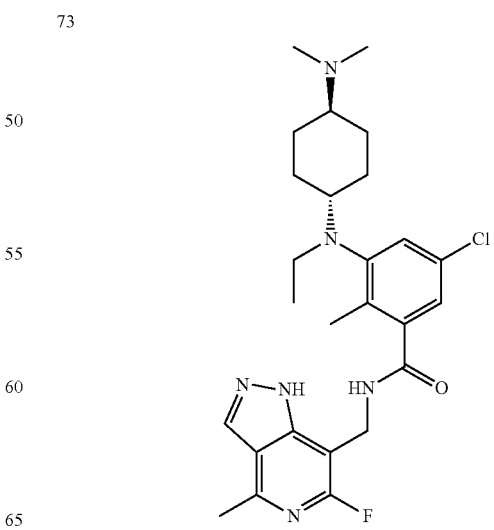 |

TABLE 2-continued
| Cpd No. | Structure |
|---|---|
| 74 | 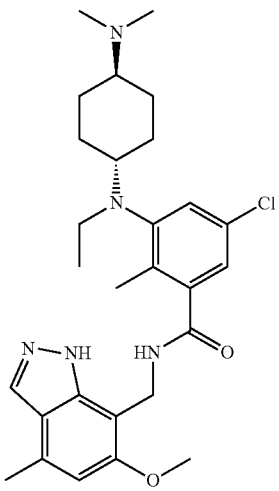 [SMILES: CCN(c1cc(Cl)cc(C(=O)NCc2c(OC)cc(C)c3cn[nH]c23)c1C)[C@H]1CC[C@H](N(C)C)CC1] |
| 75 | 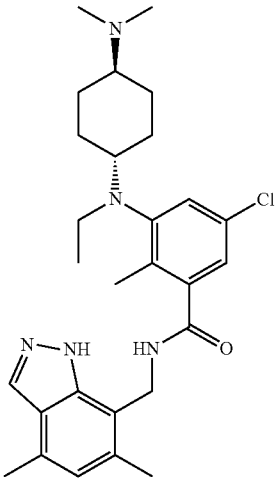 [SMILES: CCN(c1cc(Cl)cc(C(=O)NCc2c(C)cc(C)c3cn[nH]c23)c1C)[C@H]1CC[C@H](N(C)C)CC1] |
| 76 | 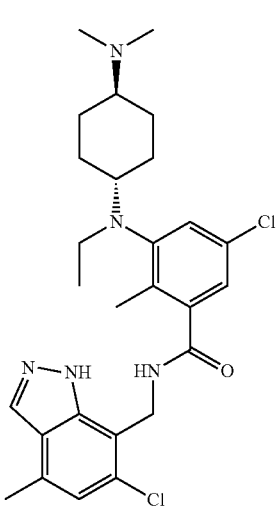 [SMILES: CCN(c1cc(Cl)cc(C(=O)NCc2c(Cl)cc(C)c3cn[nH]c23)c1C)[C@H]1CC[C@H](N(C)C)CC1] |
| 77 | 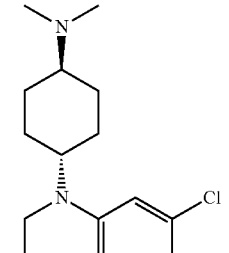 |
| 78 | 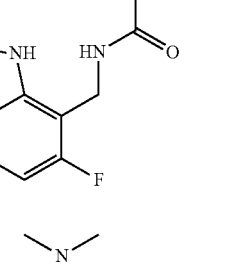 |
| 79 | 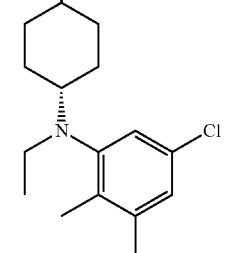 |

TABLE 2-continued
| Cpd No. | Structure |
|---|---|
| 80 | 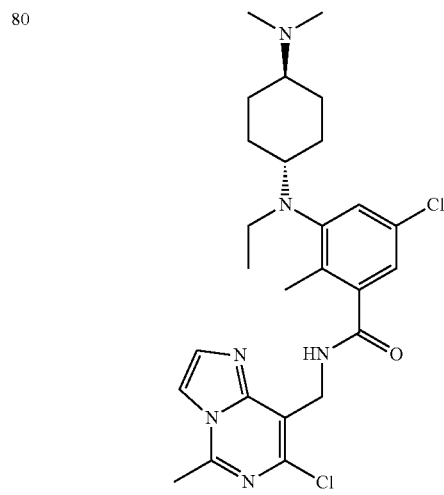 |
| 81 | 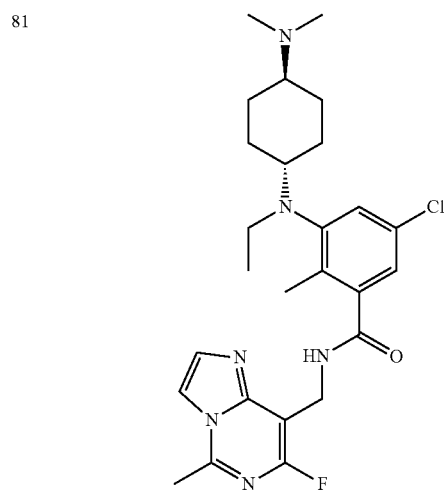 |
| 82 | 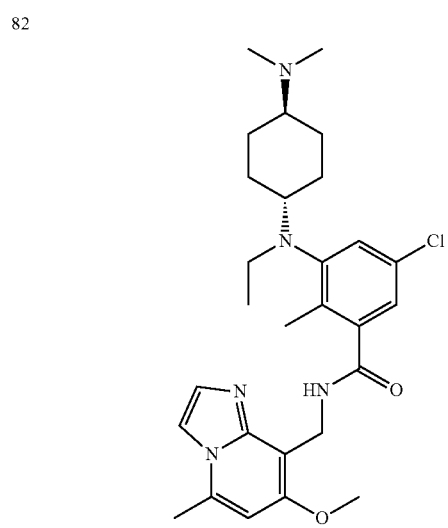 |在
| 83 | 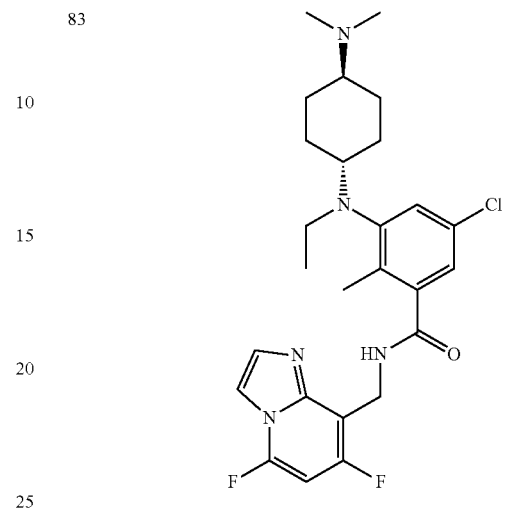 |
| 84 | 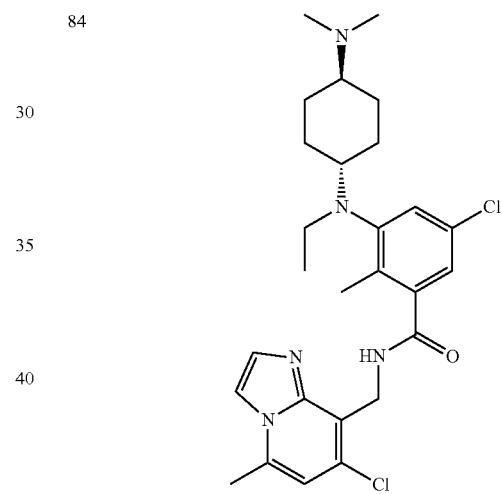 |
| 85 | 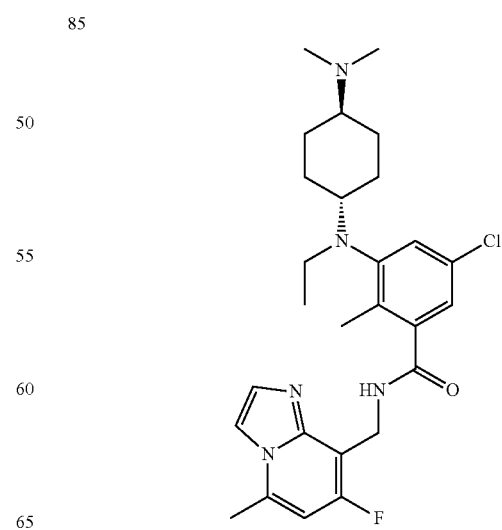 |

TABLE 2-continued

| Cpd No. | Structure |
|---|---|
| 86 | 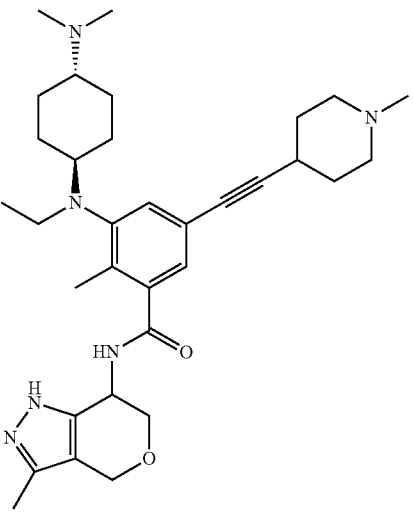 [SMILES: CCN(c1cc(C#CC2CCN(C)CC2)cc(C(=O)NC2COCc3c(C)n[nH]c32)c1C)[C@H]1CC[C@H](N(C)C)CC1] |
| 87 | 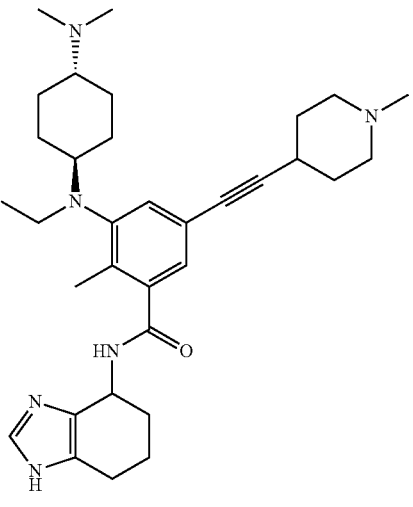 [SMILES: CCN(c1cc(C#CC2CCN(C)CC2)cc(C(=O)NC2CCCc3[nH]cnc32)c1C)[C@H]1CC[C@H](N(C)C)CC1] |
| 88 | 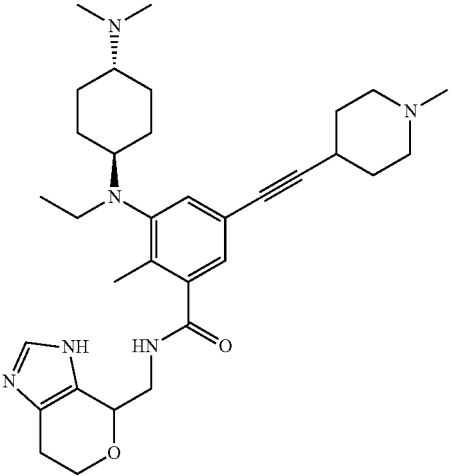 [SMILES: CCN(c1cc(C#CC2CCN(C)CC2)cc(C(=O)NCC2OCCc3nc[nH]c32)c1C)[C@H]1CC[C@H](N(C)C)CC1] |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—CH₂CH₂CH₂CH₂—), s-butyl (—CHCH₃CH₂CH₂—), i-butyl (—C(CH₃)₂CH₂—), n-pentyl (—CH₂CH₂CH₂CH₂CH₂—), s-pentyl (—CHCH₃CH₂CH₂CH₂—) or n-hexyl (—CH₂CH₂CH₂CH₂CH₂CH₂—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, and [4.4.0] bicyclodecane and [2.2.2] bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, 0 or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "azole," as used herein, refers to a class of five-membered nitrogen heterocyclic ring compounds containing at least another non-carbon atom of nitrogen, sulfur, or oxygen.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups.

Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to —NH$_2$. "Alkylamino" includes groups of compounds wherein the nitrogen of —NH$_2$ is bound to at least one alkyl group. Examples of alkylamino groups include benzylamino, methylamino, ethylamino, phenethylamino, etc. "Dialkylamino" includes groups wherein the nitrogen of —NH$_2$ is bound to two alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms, it being understood that not all isomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine.

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any Formula described herein include the compounds themselves, as well as their salts, and their solvates, if applicable. A salt, for example, can be formed between an anion and a positively charged group (e.g., amino) on an azole compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an azole compound. Suitable cations include sodium ion, potassium ion, magnesium ion, calcium ion, and an ammonium cation such as tetramethylammonium ion. The azole compounds also include those salts containing quaternary nitrogen atoms.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are azole compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention provides methods for the synthesis of the compounds of any of the Formulae described herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art or those described in WO 2012/142504, WO 2012/142513 and WO 2012/1188 which are incorporated herein by reference. The compounds of this invention having any of the Formulae described herein may be prepared according to the procedures illustrated in Schemes 1-4 below, from commercially available starting materials or starting materials which can be prepared using literature procedures. The R groups (such as $R_1$, $R_2$, $R_3$, $R_4$, $R_6$, $R_7$, $R_8$, and $R_{12}$) in Schemes 1-4 are as defined in any Formula described herein, unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

Preferred protecting groups include, but are not limited to:
For a hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:
AA ammonium acetate
ACN acetonitrile
Ac acetyl
AcOH acetic acid
atm atmosphere
aq. Aqueous
BID or b.i.d. bis in die (twice a day)
tBuOK potassium t-butoxide
Bn benzyl
BOC tert-butoxy carbonyl
BOP (benzotriazol-1-yloxy)tris(dimethylamino)-phosphoniumhexafluorophosphate
Cbz benzyloxy carbonyl
$CDCl_3$ deuterated chloroform
$CH_2Cl_2$ dichloromethane
COMU (1-Cyano-2-ethoxy-2-oxoethylidenaminooxy) dimethyl-amino-morpholino-carbenium hexafluorophosphate d days
DBU 1,8-diazabicyclo[5.4.0]undec-7-ene
DCE 1,2 dichloroethane
DCM dichloromethane
DEAD Diethyl azodicarboxylate
DIAD Diisopropyl azodicarboxylate
DiBAL-H diisobutyl aluminium hydride
DIPEA N,N-diisopropylethylamine (Hunig's base)
DMA Dimethylacetamide
DMAP N,N dimethyl-4-aminopyridine
DMB 2,4 dimethoxy benzyl
DMF N,N-Dimethylformamide
DMSO Dimethyl sulfoxide
DPPA Diphenylphosphonic azide
EA or EtOAc Ethyl acetate
EDC or EDCI N-(3-Dimethylaminopropyl)-N'-ethylcarbodiimide
$Et_2O$ diethyl ether
ELS Evaporative Light Scattering
ESI– Electrospray negative mode
ESI+ Electrospray positive mode
$Et_3N$ or TEA triethylamine
EtOH ethanol
FA formic acid
FC or FCC Flash chromatography
h hours
$H_2O$ water
HATU O-(7-Azabenzotriazol-1-yl)-N,N,N',N'-tetramethyluronium hexafluorophosphate
HOAT 1-Hydroxy-7-azabenzotriazole
HOBt 1-Hydroxybenzotriazole
HO-Su N-Hydroxysuccinimide
HCl hydrogen chloride or hydrochloric acid
HPLC High performance liquid chromatography
$K_2CO_3$ potassium carbonate
KHMDs Potassium hexamethyldisilazide
LC/MS or LC-MS Liquid chromatography mass spectrum
LDA Lithium diisopropylamide
LiHMDs Lithium hexamethyldisilazide
LG leaving group
M Molar
m/z mass/charge ratio
m-CPBA meta-chloroperbenzoic acid
MeCN Acetonitrile
MeOD d4-methanol
MeI Methyl iodide
MS3 Å 3 Å molecular sieves
$MgSO_4$ Magnesium Sulfate
min minutes
Ms Mesyl
MsCl Mesyl chloride
MsO Mesylate
MS Mass Spectrum
MWI microwave irradiation
$Na_2CO_3$ sodium carbonate
$Na_2SO_4$ sodium sulfate
$NaHCO_3$ sodium bicarbonate
NaHMDs Sodium hexamethyldisilazide
NaOH sodium hydroxide
$NaHCO_3$ sodium bicarbonate
$Na_2SO_4$ sodium sulfate
NIS N-iodosuccinimide
NMR Nuclear Magnetic Resonance
o/n or O/N overnight
Pd/C Palladium on carbon
$Pd(dppf)Cl_2$.DCM [1,1'-Bis(diphenylphosphino)ferrocene]dichloropalladium(II), complex with dichloromethane
PPAA 1-Propanephosphonic acid cyclic anhydride
$Pd(OH)_2$ Palladium dihydroxide
PE Petroleum Ether
PG protecting group
PMB para methoxybenzyl
ppm parts per million
p.o. per os (oral administration)
prep HPLC preparative High Performance Liquid Chromatography
prep TLC preparative thin layer chromatography
p-TsOH para-toluenesulfonic acid
PYBOP (Benzotriazol-1-yloxy)tripyrrolidinophosphonium Hexafluorophosphate
QD or q.d. quaque die (once a day)
RBF round bottom flask
RP-HPLC Reverse phase High Performance liquid chromatography
Rt or RT Room temperature
SEM (Trimethylsilyl)ethoxymethyl
SEMCl (Trimethylsilyl)ethoxymethyl chloride
SFC Super critical chromatography
SGC silica gel chromatography
STAB Sodium triacetoxy borohydride
TBAF tetra-n-butylammonium fluoride
TBME tert-Butyl methyl ether
TEA Triethylamine
TFA trifluoroacetic acid
TfO triflate
THF tetrahydrofuran
THP tetrahydropyran
TID or t.i.d ter in die (three times a day)
TLC thin layer chromatography
TMSCl Trimethylsilyl chloride
Ts tosyl
TsOH tosic acid
UV ultraviolet

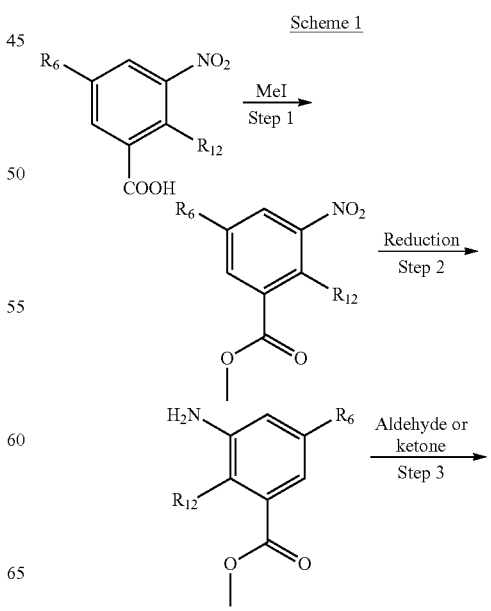

Scheme 1

-continued

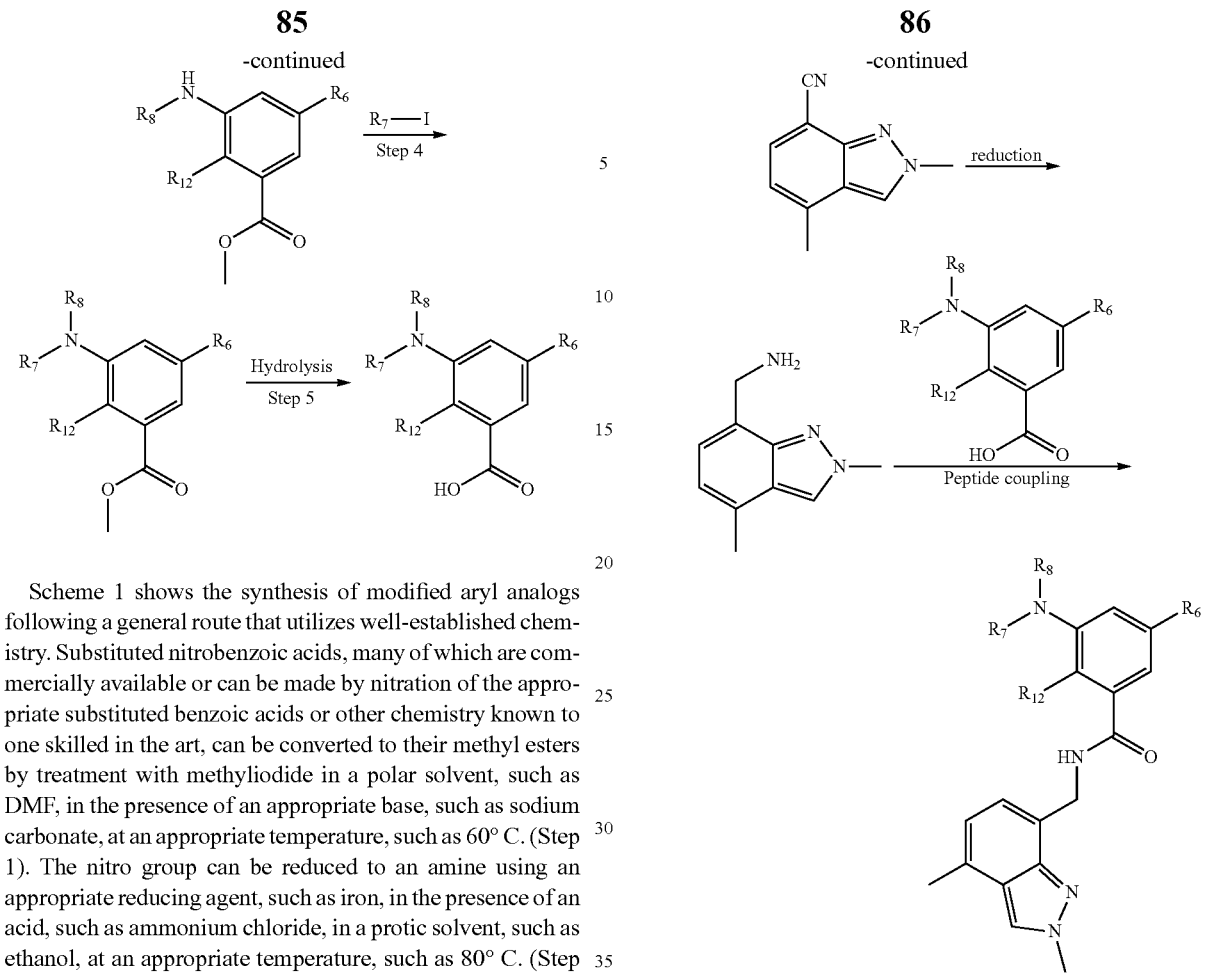

Scheme 1 shows the synthesis of modified aryl analogs following a general route that utilizes well-established chemistry. Substituted nitrobenzoic acids, many of which are commercially available or can be made by nitration of the appropriate substituted benzoic acids or other chemistry known to one skilled in the art, can be converted to their methyl esters by treatment with methyliodide in a polar solvent, such as DMF, in the presence of an appropriate base, such as sodium carbonate, at an appropriate temperature, such as 60° C. (Step 1). The nitro group can be reduced to an amine using an appropriate reducing agent, such as iron, in the presence of an acid, such as ammonium chloride, in a protic solvent, such as ethanol, at an appropriate temperature, such as 80° C. (Step 2). Introduction of the $R_8$ can be done using a reductive amination with an appropriate ketone or aldehyde in the presence of an appropriate reducing agent, such as sodium cyanoborohydride, and catalytic acid, such as acetic acid, in an appropriate solvent, such as methanol. A variety of $R_7$ groups can be introduced by alkylation using $R_7$-LG, where LG is a leaving group, such as iodine, in the presence of a mild base, such as cesium carbonate, in an appropriate polar solvent, such as acetonitrile, at an appropriate temperature, such as 80° C. (Step 4). Alternatively, $R_7$ groups can be introduced by reductive amination with $R_7$-ketone or $R_7$-aldehyde in the presence of an appropriate reducing agent, such as sodium cyanoborohydride, and catalytic acid, such as acetic acid, in an appropriate solvent, such as methanol. The ester moiety can be converted to an amide using a standard two step protocol. The ester can be hydrolyzed to the corresponding acid using a suitable base, such as sodium hydroxide, in a polar solvent, such as ethanol (Step 5).

Scheme 2

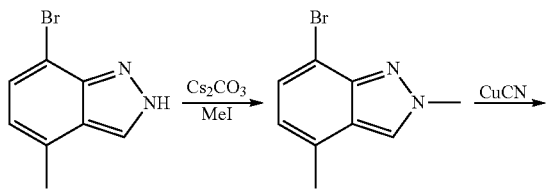

Scheme 2 shows the synthesis of modified azole analogs following a general route that utilizes well-established chemistry. Azole-nitrile (e.g., 2,6-dimethyl-2H-indazole-7-carbonitrile shown in Scheme 2), many of which are commercially available or can be made by known methods, can be reduced to an amine using an appropriate reducing agent, such as Raney-Nickel in the presence of hydrogen, in a protic solvent, such as methanol containing ammonia, at an appropriate temperature, such as 22° C. The resulting amine would then be subjected to a standard amide coupling reaction whereupon the appropriate acid (see, e.g., Scheme 1, WO 2012/142504 and WO 2012/142513, which are incorporated herein by reference) would be added along with a suitable amide coupling reagent, such as PYBOP, in a suitable solvent, such as DMSO, to give the desired amide. Similarly, other amine compounds (e.g., X—$NH_2$ or X—$(CH_2)_2$—$NH_2$), either commercially available or readily synthesized by a skilled chemist, can be coupled with the acid to afford the desired amide having different linkers.

A person of ordinary skill in the art will recognize that in the above schemes the order of many of the steps are interchangeable.

Compounds of the present invention inhibit the histone methyltransferase activity of EZH2 or a mutant thereof and, accordingly, in one aspect of the invention, certain compounds disclosed herein are candidates for treating, or preventing certain conditions and diseases in which EZH2 plays a role. The present invention provides methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, polymorph, solvate, or stereoisomer thereof.

The disorder in which EZH2-mediated protein methylation plays a part can be cancer or a precancerous condition. The present invention further provides the use of a compound of the present invention, or a pharmaceutically acceptable salt, polymorph or solvate thereof in the treatment of cancer or pre-cancer the course of which can be influenced by modulating EZH2-mediated protein methylation, or, for the preparation of a medicament useful for the treatment of such cancer or pre-cancer. Exemplary cancers that may be treated include lymphomas, including non-Hodgkin's lymphoma, follicular lymphoma (FL) and diffuse large B-cell lymphoma (DLBCL); melanoma; and leukemia, including CML. Exemplary precancerous condition includes myelodysplastic syndrome (MDS; formerly known as preleukemia).

The present invention also provides methods of protecting against a disorder in which EZH2-mediated protein methylation plays a part in a subject in need thereof by administering a therapeutically effective amount of compound of the present invention, or a pharmaceutically acceptable salt, polymorph or solvate thereof, to a subject in need of such treatment. The disorder can be cancer, e.g., cancer in which EZH2-mediated protein methylation plays a role. The present invention also provides the use of compound of the present invention, or a pharmaceutically acceptable salt, polymorph, solvate, or stereoisomer thereof, for the preparation of a medicament useful for the prevention of a cell proliferative disorder associated, at least in part, with EZH2-mediated protein methylation.

The compounds of this invention can or may be used to modulate protein (e.g., histone) methylation, e.g., to modulate histone methyltransferase or histone demethylase enzyme activity. At least some of the compounds of the invention can be used in vivo or in vitro for modulating protein methylation. Histone methylation has been reported to be involved in aberrant expression of certain genes in cancers, and in silencing of neuronal genes in non-neuronal cells. At least some compounds described herein are suitable candidates for treating these diseases, i.e., to decrease methylation or restore methylation to roughly its level in counterpart normal cells.

Compounds that are methylation modulators can or may be used for modulating cell proliferation. For example, in some cases excessive proliferation may be reduced with agents that decrease methylation, whereas insufficient proliferation may be stimulated with agents that increase methylation. Accordingly, diseases that may be treated by the compounds of the invention could include hyperproliferative diseases, such as benign cell growth and malignant cell growth.

As used herein, a "subject" is interchangeable with a "subject in need thereof", both of which refer to a subject having a disorder in which EZH2-mediated protein methylation plays a part, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. A subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition. For example, the cancer is lymphoma, leukemia, melanoma, or rhabdomyosarcoma. Preferably, the lymphoma is non-Hodgkin's lymphoma, follicular lymphoma or diffuse large B-cell lymphoma. Alternatively, the leukemia is chronic myelogenous leukemia (CML). The precancerous condition is myelodysplastic syndromes (MDS, formerly known as preleukemia).

As used herein, the term "cell proliferative disorder" refers to conditions in which unregulated or abnormal growth, or both, of cells can lead to the development of an unwanted condition or disease, which may or may not be cancerous. Exemplary cell proliferative disorders that may be treated with the compounds of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. The methods and uses provided herein can be or may be used to treat or alleviate a symptom of cancer or to identify suitable candidates for such purposes. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders that may be treated using one or more compounds of the present invention include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers that may be treated using one or more compounds of the present invention include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin's lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. In one aspect, compositions of the present invention may be used to treat a cancer selected from the group consisting of a hematologic cancer of the present invention or a hematologic cell proliferative disorder of the present invention, or used to identify suitable candidates for such purposes. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. In one aspect, compositions of the present invention may be used to treat lung cancer or cell proliferative disorders of the lung, or used to identify suitable candidates for such purposes. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. In one aspect, compositions of the present invention may be used to treat colon cancer or cell proliferative disorders of the colon, or used to identify suitable candidates for such purposes. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. In one aspect, compositions of the present invention may be used to treat breast cancer, or used to identify suitable candidates for such purposes. Breast cancer may include all forms of cancer of the breast. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

A compound of the present invention, or a pharmaceutically acceptable salt, polymorph, or solvate thereof, may be used to treat breast cancer, or used to identify suitable candidates for such purposes. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, polymorph or solvate thereof, may be used to treat or prevent a cell proliferative disorder of the breast, or to treat or prevent breast cancer, in a subject having an increased risk of developing breast cancer relative to the population at large, or used to identify suitable candidates for such purposes. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, polymorph or solvate thereof. The biological or medical response can be the treatment of cancer. The biological or medical response can be treatment or prevention of a cell proliferative disorder. The biological response or effect can also include a change in cell proliferation or growth that occurs in vitro or in an animal model, as well as other biological changes that are observable in vitro. In vitro or in vivo biological assays can include, but are not limited to, enzymatic activity assays, electrophoretic mobility shift assays, reporter gene assays, in vitro cell viability assays, and the assays described herein.

For example, an in vitro biological assay that can be used includes the steps of (1) mixing a histone substrate (e.g., an isolated histone sample, an isolated histone peptide representative of human histone H3 residues 21-44 containing either an unmodified lysine 27 (H3K27me0) or dimethylated lysine 27 (H3K27me2), or an isolated oligonucleosome substrate) with recombinant PRC2 enzymes that include a wild type or mutant EZH2 subunit; (2) adding a compound of the invention to this mixture; (3) adding non-radioactive and $^3$H-labeled S-Adenosyl methionine (SAM) to start the reaction; (4) adding excessive amount of non-radioactive SAM to stop the reaction; (4) washing off the free non-incorporated $^3$H-SAM; and (5) detecting the quantity of $^3$H-labeled histone substrate by any methods known in the art (e.g., by a PerkinElmer TopCount platereader).

For example, an in vivo study that can be used includes the steps of (1) administering a compound of the invention into a mouse model (such as WSU-DLCL2 xenograft tumor bearing mouse model or KARPAS-422 human diffused large B-Cell lymphoma mouse xenograft model) at certain level of dosage for certain periods of time, e.g., 7-28 days; (2) sacrificing the mouse and isolating the tumor tissue; (3) measuring the tumor volume and body weight and (4) extracting histone from the tumor tissue for measuring the histone methylation by ELISA.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, analog or derivative thereof, to a subject in need of treatment of cancer. Monotherapy may be contrasted with combination therapy, in which a combination of multiple active compounds is administered, preferably with each component of the combination present in a therapeutically effective amount. Monotherapy with a compound of the present invention, or a pharmaceutically acceptable salt, polymorph or solvate thereof, may be more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

As used herein, the term "alleviate" is meant to describe a process by which the severity of a sign or symptom of a disorder is decreased. Importantly, a sign or symptom can be alleviated without being eliminated. The administration of pharmaceutical compositions of the invention can or may lead to the elimination of a sign or symptom, however, elimination is not required. Effective dosages should be expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

Severity can also describe the degree to which a tumor has secreted growth factors, degraded the extracellular matrix, become vascularized, lost adhesion to juxtaposed tissues, or metastasized. Moreover, severity can describe the number of locations to which a primary tumor has metastasized. Finally, severity can include the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness.

Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here.

Treating cancer may result in or can result in a reduction in size of a tumor. A reduction in size of a tumor may also be referred to as "tumor regression". Preferably, after treatment, tumor size would be reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer may result in or can result in a reduction in tumor volume. Preferably, after treatment, tumor volume would be reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer may result in or can result in a decrease in number of tumors. Preferably, after treatment, tumor number would be reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer may result in or can result in a decrease in number of metastatic lesions in other tissues or organs distant from the primary tumor site. Preferably, after treatment, the number of metastatic lesions would be reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer may result in or can result in an increase in average survival time of a population of treated subjects in comparison to a population receiving carrier alone. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in or can result in an increase in average survival time of a population of treated subjects in comparison to a population of untreated subjects. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in or can result in increase in average survival time of a population of treated subjects in comparison to a population receiving monotherapy with a drug that is not a compound of the present invention, or a pharmaceutically acceptable salt, analog or derivative thereof. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in or can result in a decrease in the mortality rate of a population of treated subjects in comparison to a population receiving carrier alone. Treating cancer may result in or can result in a decrease in the mortality rate of a population of treated subjects in comparison to an untreated population. Treating cancer may result in or can result in a decrease in the mortality rate of a population of treated subjects in comparison to a population receiving monotherapy with a drug that is not a compound of the present invention, or a pharmaceutically acceptable salt, analog or derivative thereof. Preferably, the mortality rate would be decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer may result in or can result in a decrease in tumor growth rate. Preferably, after treatment, tumor growth rate would be reduced by at least 5% relative to number prior to treatment; more preferably, tumor growth rate would be reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer may result in or can result in a decrease in tumor regrowth. Preferably, after treatment, tumor regrowth would be less than 5%; more preferably, tumor regrowth would be less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder may result in or can result in a reduction in the rate of cellular proliferation. Preferably, after treatment, the rate of cellular proliferation would be reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder may result in or can result in a reduction in the proportion of proliferating cells. Preferably, after treatment, the proportion of proliferating cells would be reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder may result in or can result in a decrease in size of an area or zone of cellular proliferation. Preferably, after treatment, size of an area or zone of cellular proliferation would be reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder may result in or can result in a decrease in the number or proportion of cells having an abnormal appearance or morphology. Preferably, after treatment, the number of cells having an abnormal morphology would be reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, polymorph or solvate thereof, acts selectively on a cancer or precancerous cell but not on a normal cell. Preferably, a compound of the present invention, or a pharmaceutically acceptable salt, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, polymorph or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, polymorph or solvate thereof, to a cell or a subject in need thereof can result in modulation (i.e., stimulation or inhibition) of an activity of a protein methyltransferase of interest.

The present invention provides methods to assess biological activity of a compound of the present invention, or a pharmaceutically acceptable salt, polymorph or solvate thereof or methods of identifying a test compound as an inhibitor of a mutant EZH2.

Point mutations of the EZH2 gene at a single amino acid residue (e.g., Y641, A677, and A687) of EZH2 have been reported to be linked to lymphoma. More examples of EZH2 mutants and methods of treatment are described in U.S. Patent Application Publication 2013-0040906, the entire content of which is incorporated herein by reference in its entirety.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, polymorph or solvate thereof, to a cell or a subject in need thereof may or can result in modulation (i.e., stimulation or inhibition) of an activity of an intracellular target (e.g., substrate). Several intracellular targets may or can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder may result in or can result in cell death, and preferably, cell death would result in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, polymorph or solvate thereof, would not be significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, polymorph or solvate thereof, may or can induce or activate cell death selectively in cancer cells. Administering to a subject in need thereof a compound of the present invention, or a pharmaceutically acceptable salt, polymorph or solvate thereof, may or can induce or activate cell death selectively in cancer cells. Contacting a cell with a compound of the present invention, or a pharmaceutically acceptable salt, polymorph or solvate thereof, may or can induce cell death selectively in one or more cells affected by a cell proliferative disorder. Preferably, administering to a subject in need thereof a compound of the present invention, or a pharmaceutically acceptable salt, polymorph or solvate thereof, would induce cell death selectively in one or more cells affected by a cell proliferative disorder.

One aspect of the present invention relates to a method of treating or preventing cancer (e.g., the course of which can be influenced by modulating EZH2-mediated protein methylation) by administering a compound of the present invention, or a pharmaceutically acceptable salt, polymorph or solvate thereof, to a subject in need thereof, where administration of the compound of the present invention, or a pharmaceutically acceptable salt, polymorph or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose. The present invention also relates to a method used to identify suitable candidates for treating or preventing cancer.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention.

As used herein, "combination therapy" or "co-therapy" includes the administration of a compound of the present invention, or a pharmaceutically acceptable salt, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents.

Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Any-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In preferred embodiments, a compound of the present invention, or a pharmaceutically acceptable salt, polymorph or solvate thereof, may be administered with an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

The disorder in which EZH2-mediated protein methylation plays a part can be a neurological disease. The compounds of this invention may thus also be used for treating or studying neurologic diseases such as epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCAT), and Spinocerebellar Ataxia 12 (SCA12).

Any other disease in which epigenetic methylation, which is mediated by EZH2, plays a role may be treatable or preventable using compounds and methods described herein, or such diseases and potential treatments thereof may be studied with the compounds described herein.

The present invention also provides pharmaceutical compositions comprising a compound of any of the Formulae described herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy,* 19th edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening,* Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

PREPARATORY EXAMPLE 1

General PyBOP Coupling Protocol

The carboxylic acid (1 equiv.) was then dissolved in DMSO and an appropriate methanamine (2 eq.) was added to it. The reaction mixture was stirred at room temperature for 15 min before PYBOP (1.5 equiv.) and triethyl amine (1 equiv.) was added to it and stirring was continued for overnight. After completion of the reaction, reaction mass was poured into ice, extracted with 10% MeOH/DCM. Combined organic layers were dried, concentrated to obtain crude; which then purified by column chromatography/prep. HPLC to afford the target compound.

EXAMPLE 1

5-chloro-3-(((trans)-4-(dimethylamino)cyclohexyl) (ethyl)amino)-N-((5,7-dimethylimidazo[1,2-a]pyridin-8-yl)methyl)-2-methylbenzamide

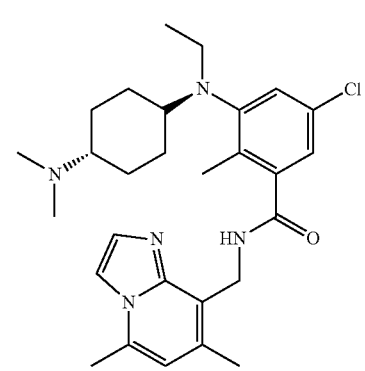

Compound 1

Step 1: Synthesis of 5,7-dimethylimidazo[1,2-a]pyridine-8-carbonitrile

To a stirred solution of compound 2-amino-4,6-dimethylnicotinonitrile (1 equiv.) in water was added chloroacetaldehyde (55% aq. solution) (1.2 equiv.) and reaction was heated at 80° C. for 16 h. On completion, it was quenched by 1N NaOH till pH 8. Solid precipitated was filtered and vacuum dried to afford the title compound (75% yield).

Step 2: Synthesis of (5,7-dimethylimidazo[1,2-a]pyridin-8-yl)methanamine

To a solution of 5,7-dimethylimidazo[1,2-a]pyridine-8-carbonitrile (1 equiv.) in methanol and aq. ammonia solution (9:1), a catalytic amount of Raney Nickel was added. The reaction mass was stirred at room temperature under hydrogen pressure (balloon pressure) for 2-5 h. On completion of reaction, it was filtered through a celite bed and the filtrate was concentrated under reduce pressure to afford respective amines (quantitative yield).

Step 3: Synthesis of 5-chloro-3-(((trans)-4-(dimethylamino)cyclohexyl)(ethyl)amino)-N-((5,7-dimethylimidazo[1,2-a]pyridin-8-yl)methyl)-2-methylbenzamide The synthesis has been described in WO 2012142513, Step 4: General PYBOP coupling conditions with (5,7-dimethylimidazo[1,2-a]pyridin-8-yl)methanamine LCMS: 496.50 (M+1)$^+$; $^1$H NMR (DMSO-d$_6$, 400 MHz) δ 9.57 (bs, 1H), 8.90 (t, 1H), 8.31 (s, 2H), 7.32 (s, 1H), 7.24 (s, 1H), 7.01 (s, 1H), 4.74 (d, 2H), 3.10 (m, 1H), 3.02 (m, 2H), 2.73 (s, 3H), 2.68 (s, 3H), 2.67 (s, 3H), 2.55 (s, 3H), 2.12 (s, 3H), 1.94 (m, 2H), 1.81 (m, 2H), 1.41 (m, 4H), 0.76 (t, 3H, J=6 Hz).

EXAMPLE 2

5-chloro-3-(((trans)-4-(dimethylamino)cyclohexyl)(ethyl)amino)-2-methyl-N-((7-methylimidazo[1,2-a]pyridin-8-yl)methyl)benzamide Compound 2

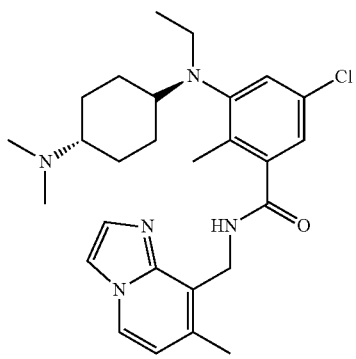

Step 1: Synthesis of 7-methylimidazo[1,2-a]pyridine-8-carbonitrile

To a stirred solution of compound 2-amino-4-methylnicotinonitrile (1 equiv.) in water was added chloroacetaldehyde (55% aq. solution) (1.2 equiv.) and the reaction was heated at 80° C. for 16 h. On completion, it was quenched by 1N NaOH till pH 8. Solid precipitated was filtered and vacuum dried to afford the title compound (75% yield).

Step 2: Synthesis of (7-methylimidazo[1,2-a]pyridin-8-yl)methanamine

To a solution of 7-methylimidazo[1,2-a]pyridine-8-carbonitrile (1 eq) in methanol and aq. ammonia solution (9:1), catalytic amount of Raney Nickel was added. Reaction mass was stirred at room temperature under hydrogen pressure (balloon pressure) for 2-5 h. On completion of reaction, it was filtered through celite bed and filtrate was concentrated under reduce pressure to afford respective amines (quantitative yield).

Step 3: Synthesis of 5-chloro-3-(((trans)-4-(dimethylamino)cyclohexyl)(ethyl)amino)-2-methyl-N-((7-methylimidazo[1,2-a]pyridin-8-yl)methyl)benzamide The synthesis has been described in WO 2012142513.

Step 4: General PYBOP coupling conditions with (7-methylimidazo[1,2-a]pyridin-8-yl)methanamine LCMS: 482.45 (M+1)$^+$; $^1$H NMR (DMSO-d$_6$, 400 MHz) δ 9.51 (bs, 1H), 8.89 (t, 1H), 8.76 (d, 1H, J=6.8 Hz), 8.31 (s, 1H), 8.21 (s, 1H), 7.41 (d, 1H, J=6.4 Hz), 7.25 (s, 1H), 7.03 (s, 1H), 4.32 (d, 2H, 4.8 Hz), 3.10-3.01 (m, 3H), 2.69 (bs, 6H), 2.58 (s, 3H), 2.13 (s, 3H), 1.94-1.81 (m, 4H), 1.42 (m, 4H), 0.77 (t, 3H, J=6.4 Hz), 1 proton merged in solvent peak.

EXAMPLE 3

Synthesis of 5-chloro-3-(((trans)-4-(dimethylamino)cyclohexyl)(ethyl)amino)-N-(imidazo[1,2-a]pyridin-8-ylmethyl)-2-methylbenzamide Compound 3

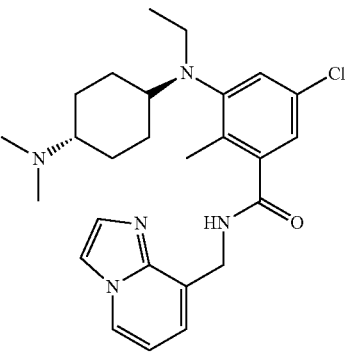

Step 1: Synthesis of imidazo[1,2-a]pyridin-8-ylmethanamine

To a solution of imidazo[1,2-a]pyridine-8-carbonitrile (1 equiv.) in methanol and aq. ammonia solution (9:1), catalytic amount of Raney Nickel was added. Reaction mass was stirred at room temperature under hydrogen pressure (balloon pressure) for 2-5 h. On completion of reaction, it was filtered through celite bed and filtrate was concentrated under reduce pressure to afford respective amines (quantitative yield).

Step 2: Synthesis of 5-chloro-3-(((trans)-4-(dimethylamino)cyclohexyl)(ethyl)amino)-2-methyl-N-((7-methylimidazo[1,2-a]pyridin-8-yl)methyl)benzamide The synthesis has been described in WO 2012142513.

Step 3: General PYBOP coupling conditions with imidazo[1,2-a]pyridin-8-ylmethanamine LCMS: 468.45 (M+1)$^+$; $^1$H NMR (DMSO-d$_6$, 400 MHz) δ 9.62 (bs, 1H), 9.12 (m, 1H), 8.84 (d, 1H, J=6.4 Hz), 8.42 (s, 1H), 8.28 (s, 1H), 7.85 (d, 1H, J=6.4 Hz), 7.51 (t, 1H, J=7.2 Hz), 7.27 (d, 2H, J=12.0 Hz), 4.77 (d, 2H, J=4.8 Hz), 3.12-3.04 (m, 3H) 2.69-2.68 (m, 7H), 2.20 (m, 3H), 1.96-1.84 (m, 4H), 1.44 (m, 4H), 0.81 (t, 3H, J=5.6 Hz).

EXAMPLE 4

Synthesis of 5-chloro-N-((2,4-dimethyl-2H-indazol-7-yl)methyl)-3-(((1s,4s)-4-(dimethylamino)cyclohexyl)(ethyl)amino)-2-methylbenzamide Compound 4

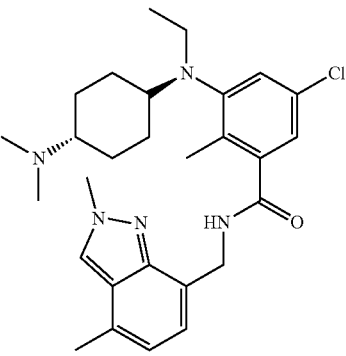

Step 1: Synthesis of 7-bromo-2,4-dimethyl-2H-indazole

To a solution of 7-bromo-4-methyl-1H-indazole (1 equiv.) in acetonitrile, $Cs_2CO_3$ (1.3 equiv.) and MeI (3 equiv.) was added and reaction was heated at 80° C. for 1.5 h. On completion, it was cooled and quenched by addition of water. Extraction was carried out using ethyl acetate. Organic layer was dried over $Na_2SO_4$ and crude compound was column purified to afford the title compound. (Polar isomer confirmed as N-2-Methyl and non-polar isomer confirmed as N-1-Methyl by NOE experimentation).

Step 2: Synthesis of 2,4-dimethyl-2H-indazole-7-carbonitrile

To a solution of 7-bromo-2,4-dimethyl-2H-indazole (1 eq.) in NMP, was added CuCN (2 equiv.) and heated at 130° C. for 16 h. On completion, water was added to quench the reaction, solid precipitated was filtered and purified by column chromatography to afford the title compound (40-60% yield)

Step 3: Synthesis of (2,4-dimethyl-2H-indazol-7-yl)methanamine

To a solution of 2,4-dimethyl-2H-indazole-7-carbonitrile (1 equiv.) in methanol and aq. ammonia solution (9:1), catalytic amount of Raney Nickel was added. Reaction mass was stirred at room temperature under hydrogen pressure (balloon pressure) for 2-5 h. On completion of reaction, it was filtered through celite bed and filtrate was concentrated under reduce pressure to afford the title compound (quant. yield).

Step 4: Synthesis of 5-chloro-N-((2,4-dimethyl-2H-indazol-7-yl)methyl)-3-(((1s,4s)-4-(dimethylamino)cyclohexyl)(ethyl)amino)-2-methylbenzamide Step 5: General PYBOP coupling conditions with (2,4-dimethyl-2H-indazol-7-yl)methanamine (0.085 g, 29% yield)

LCMS: 496.40 (M+1)$^+$; $^1$H NMR (DMSO-$d_6$, 400 MHz) δ 9.35 (bs, 1H), 8.75 (t, 1H, J=4.8&5.6 Hz), 8.10 (s, 1H), 7.43-7.36 (m, 2H), 7.21 (s, 1H), 7.02 (s, 1H), 4.51 (d, 2H, J=5.6 Hz), 4.00 (s, 3H), 3.10 (m, 1H), 3.02 (q, 2H), 2.70 (m, 1H), 2.68 (s, 3H), 2.67 (s, 3H), 2.58 (s, 3H), 2.15 (s, 3H), 1.94 (m, 2H), 1.83 (m, 2H), 1.42 (m, 4H), 0.79 (t, 3H, J=6.8 Hz).

EXAMPLE 5

Synthesis of 5-chloro-N-((2,6-dimethyl-2H-indazol-7-yl)methyl)-3-(((trans)-4-(dimethylamino)cyclohexyl)(ethyl)amino)-2-methylbenzamide Compound 5

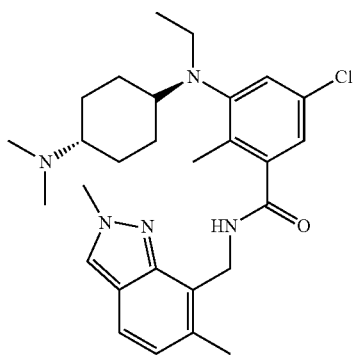

Step 1: Synthesis of 7-bromo-2,6-dimethyl-2H-indazole

To a solution of 7-bromo-6-methyl-1H-indazole (1 equiv.) in acetonitrile, $Cs_2CO_3$ (1.3 equiv.) and MeI (3 eq.) was added and reaction was heated at 80° C. for 1.5 h. On completion, it was cooled and quenched by addition of water. Extraction was carried out using ethyl acetate. Organic layer was dried over $Na_2SO_4$ and crude compound was column purified to afford the title compound. (Polar isomer confirmed as N-2-Methyl and non-polar isomer confirmed as N-1-Methyl by NOE experimentation).

Step 2: Synthesis of 2,6-dimethyl-2H-indazole-7-carbonitrile

To a solution of 7-bromo-2,6-dimethyl-2H-indazole (1 equiv.) in NMP, was added CuCN (2 equiv.) and heated at 130° C. for 16 h. On completion, water was added to quench the reaction, solid precipitated was filtered and purified by column chromatography to afford the title compound (40-60% yield)

Step 3: Synthesis of (2,6-dimethyl-2H-indazol-7-yl)methanamine

To a solution of 2,6-dimethyl-2H-indazole-7-carbonitrile (1 equiv.) in methanol and aq. ammonia solution (9:1), catalytic amount of Raney Nickel was added. Reaction mass was stirred at room temperature under hydrogen pressure (balloon pressure) for 2-5 h. On completion of reaction, it was filtered through celite bed and filtrate was concentrated under reduce pressure to afford the title compound (quant. yield).

Step 4: Synthesis of 5-chloro-N-((2,6-dimethyl-2H-indazol-7-yl)methyl)-3-(((trans)-4-(dimethylamino)cyclohexyl)(ethyl)amino)-2-methylbenzamide Step 5: General PYBOP coupling conditions with (2,6-dimethyl-2H-indazol-7-yl)methanamine (0.054 g, 18.4% yield)

LCMS: 496.35 (M+1)$^+$; $^1$H NMR (D$_2$O, 400 MHz) δ 8.23 (s, 1H), 7.76 (s, 1H), 7.70 (d, 1H, J=8.4 Hz), 7.58 (s, 1H), 7.11 (d, 1H, J=8.4 Hz), 4.93 (s, 2H), 4.21 (s, 3H), 3.74-3.69 (m, 3H), 3.27-3.22 (m, 1H), 2.84 (s, 6H), 2.52 (s, 3H), 2.36 (s, 3H), 2.33-2.20 (m, 4H), 1.73-1.57 (m, 4H), 1.00 (t, 3H, J=6.8 Hz).

EXAMPLE 6

Synthesis of 5-chloro-3-(((trans)-4-(dimethylamino)cyclohexyl)(ethyl)amino)-2-methyl-N-((2-methyl-2H-indazol-7-yl)methyl)benzamide Compound 6

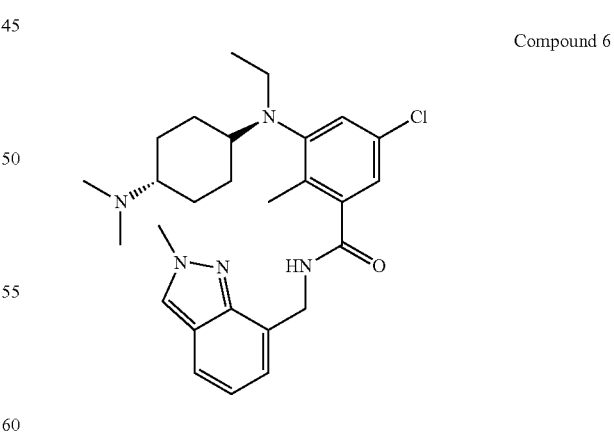

Step 1: Synthesis of 2-methyl-2H-indazole-7-carbonitrile

To a solution of 1H-indazole-7-carbonitrile (1 equiv.) in acetonitrile, $Cs_2CO_3$ (1.3 equiv.) and MeI (3 equiv.) was added and reaction was heated at 80° C. for 1.5 h. On completion, it was cooled and quenched by addition of water. Extraction was carried out using ethyl acetate. Organic layer was dried over $Na_2SO_4$ and crude compound was column purified to afford the title compound. (Polar isomer confirmed as N-2-Methyl and non-polar isomer confirmed as N-1-Methyl by NOE experimentation).

Step 2: Synthesis of (2-methyl-2H-indazol-7-yl)methanamine

To a solution of 2-methyl-2H-indazole-7-carbonitrile (1 equiv.) in methanol and aq. ammonia solution (9:1), catalytic amount of Raney Nickel was added. Reaction mass was stirred at room temperature under hydrogen pressure (balloon pressure) for 2-5 h. On completion of reaction, it was filtered through celite bed and filtrate was concentrated under reduce pressure to afford the title compound (quant. yield).

Step 3: Synthesis of 5-chloro-3-(((trans)-4-(dimethylamino)cyclohexyl)(ethyl)amino)-2-methyl-N-((2-methyl-2H-indazol-7-yl)methyl)benzamide Step 4: General PYBOP coupling conditions with (2-methyl-2H-indazol-7-yl)methanamine (0.045 g, 12% yield)

LCMS: 482.50 (M+1)$^+$; $^1$H NMR (DMSO-d$_6$, 400 MHz) δ 9.32 (bs, 1H), 8.87 (t, 1H), 8.36 (s, 1H), 7.59 (d, 1H, J=8 Hz), 7.25 (s, 1H), 7.20 (s, 1H), 7.13 (d, 1H, J=6.4 Hz), 7.02 (t, 1H, J=6.8 Hz), 4.77 (d, 2H, J=4.8 Hz), 4.20 (s, 3H), 3.13-3.04 (m, 3H), 2.69 (m, 7H), 2.24 (s, 3H), 1.95-1.86 (m, 4H), 1.46 (m, 4H), 0.82 (t, 3H).

EXAMPLE 7

Synthesis of 5-chloro-3-(((trans)-4-(dimethylamino)cyclohexyl)(ethyl)amino)-2-methyl-N-(pyrazolo[1,5-a]pyridin-7-ylmethyl)benzamide

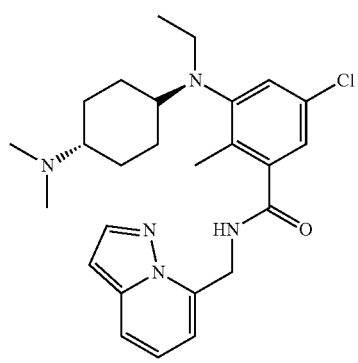

Compound 7

Step 1: Synthesis of pyrazolo[1,5-a]pyridin-7-ylmethanamine

To a solution of pyrazolo[1,5-a]pyridine-7-carbonitrile (1 equiv.) in methanol and aq. ammonia solution (9:1), catalytic amount of Raney Nickel was added. Reaction mass was stirred at room temperature under hydrogen pressure (balloon pressure) for 2-5 h. On completion of reaction, it was filtered through celite bed and filtrate was concentrated under reduce pressure to afford the title compound (quant. yield).

Step 2: Synthesis of 5-chloro-3-(((trans)-4-(dimethylamino)cyclohexyl)(ethyl)amino)-2-methyl-N-(pyrazolo[1,5-a]pyridin-7-ylmethyl)benzamide Step 3: General PYBOP coupling conditions with pyrazolo[1,5-a]pyridin-7-ylmethanamine (0.04 g, 25% yield)

LCMS: 468.40 (M+1)$^+$; $^1$H NMR (DMSO-d$_6$, 400 MHz) δ 9.40 (bs, 1H), 9.10 (t, 1H), 8.10 (s, 1H), 7.70 (d, 1H), 7.25 (m, 3H), 6.90 (d, 1H), 6.70 (s, 1H), 4.85 (d, 2H), 3.20-3.00 (m, 3H), 2.75 (m, 1H), 2.70 (s, 6H), 2.25 (s, 3H), 1.95 (m, 2H), 1.85 (m, 2H), 1.45 (m, 4H), 0.80 (t. 3H).

EXAMPLE 8

Synthesis of 5-chloro-3-(((trans)-4-(dimethylamino)cyclohexyl)(ethyl)amino)-2-methyl-N-(2-(1-methyl-1H-imidazol-2-yl)ethyl)benzamide

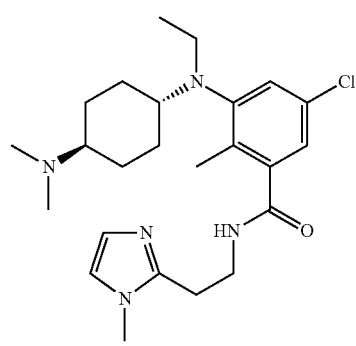

Compound 8

General PYBOP coupling conditions with 2-(1-methyl-1H-imidazol-2-yl)ethanamine (0.04 g, 15.2% yield).

LCMS: 446.30 (M+1)$^+$; $^1$H NMR (D$_2$O, 400 MHz) δ 7.62 (bs, 1H), 7.43-7.42 (m, 2H), 7.30 (bs, 1H), 3.93 (s, 3H), 3.85 (t, 2H, J=5.8 Hz), 3.39-3.37 (m, 4H), 3.23 (m, 2H), 2.85 (s, 6H), 2.22-2.16 (m, 7H), 1.59 (m, 4H), 0.94 (t, 3H, J=6.2 Hz).

EXAMPLE 9

Synthesis of N-(2-(1-benzyl-1H-imidazol-2-yl)ethyl)-5-chloro-3-(((trans)-4-(dimethylamino)cyclohexyl)(ethyl)amino)-2-methylbenzamide

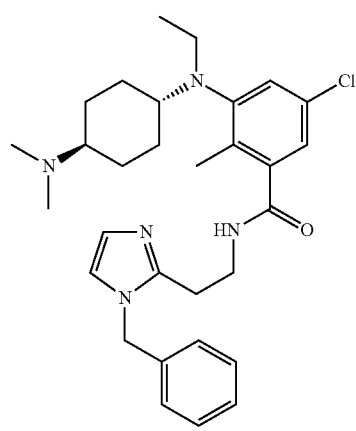

Compound 9

General PYBOP coupling conditions with 2-(1-benzyl-1H-imidazol-2-yl)ethanamine (0.04 g, 15.2% yield).

LCMS: 522.45 (M+1)$^+$; $^1$H NMR (DMSO-d$_6$, 400 MHz) δ 8.38 (m, 1H), 7.35-7.29 (m, 3H), 7.17-7.15 (m, 4H), 6.99 (s, 1H), 6.83 (s, 1H), 5.20 (s, 2H), 3.49 (m, 2H), 3.02 (m, 4H), 2.83 (m, 2H), 2.13 (s, 9H), 1.73 (m, 4H), 1.38-1.35 (m, 2H), 1.14-1.11 (m, 2H), 0.79 (t, 3H).

EXAMPLE 10

Synthesis of N-(2-(1H-imidazol-2-yl)ethyl)-5-chloro-3-(((trans)-4-(dimethylamino)cyclohexyl)(ethyl)amino)-2-methylbenzamide

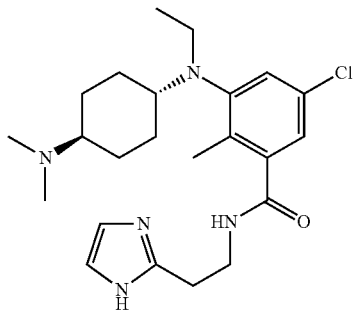

Compound 10

General PYBOP coupling conditions with 2-(1H-imidazol-2-yl)ethanamine (0.08 g, 31.3% yield).

LCMS: 432.40 (M+1)$^+$; $^1$H NMR (DMSO-d$_6$, 400 MHz) δ 11.76 (bs, 1H), 8.41 (bs, 1H), 7.17 (d, 1H, J=0.8 Hz), 6.99 (m, 2H), 6.77 (bs, 1H), 3.50 (m, 2H), 3.02 (m, 3H), 2.85 (m, 2H), 2.13 (s, 9H), 1.75 (m, 5H), 1.38-1.12 (m, 4H), 0.79 (t, 3H).

EXAMPLE 11

Synthesis of 5-chloro-3-(((trans)-4-(dimethylamino)cyclohexyl)(ethyl)amino)-2-methyl-N-(2-(1-methyl-1H-benzo[d]imidazol-2-yl)ethyl)benzamide

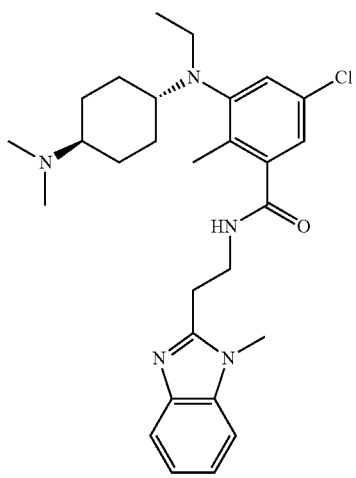

Compound 11

General PYBOP coupling conditions with 2-(1-methyl-1H-benzo[d]imidazol-2-yl)ethanamine (0.09 g, 30.7% yield).

LCMS: 496.40 (M+1)$^+$; $^1$H NMR (DMSO-d$_6$, 400 MHz) δ 9.55 (bs, 1H), 8.54 (bs, 1H), 7.66 (m, 2H), 7.33 (m, 2H), 7.21 (bs, 1H), 7.07 (bs, 1H), 3.88 (s, 3H), 3.69 (m, 3H), 3.25-3.09 (m, 5H), 2.67 (bs, 6H), 2.09 (s, 3H), 1.95 (m, 2H), 1.81 (m, 2H), 1.41 (m, 4H), 0.78 (t, 3H).

EXAMPLE 12

Synthesis of 5-chloro-3-(((trans)-4-(dimethylamino)cyclohexyl)(ethyl)amino)-2-methyl-N-(2-(thiazol-2-yl)ethyl)benzamide

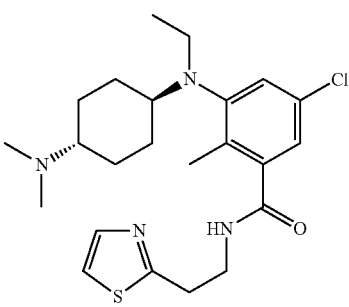

Compound 12

General PYBOP coupling conditions with 2-(thiazol-2-yl)ethanamine (0.107 g, 40.0% yield).

LCMS: 449.25 (M+1)$^+$; $^1$H NMR (DMSO-d$_6$, 400 MHz) δ 9.28 (bs, 1H), 8.49 (m, 1H), 7.73 (m, 1H), 7.62 (m, 1H), 7.22 (bs, 1H), 7.02 (bs, 1H), 3.60-3.58 (m, 2H), 3.26-3.03 (m, 6H), 2.69 (d, 6H, J=4.4 Hz), 2.14 (s, 3H), 1.95 (m, 2H), 1.84 (m, 2H), 1.43 (m, 4H), 0.80 (t, 3H).

EXAMPLE 13

Synthesis of N-(2-(benzo[d]thiazol-2-yl)ethyl)-5-chloro-3-(((trans)-4-(dimethylamino)cyclohexyl)(ethyl)amino)-2-methylbenzamide

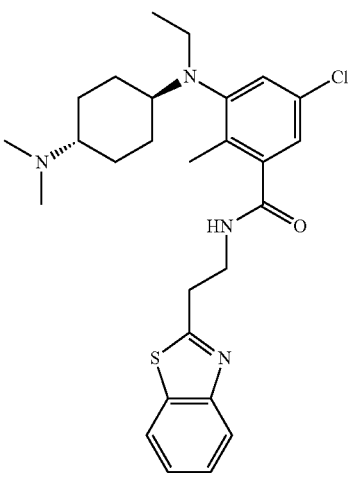

Compound 13

Step 1: Synthesis of N-(2-(benzo[d]thiazol-2-yl)ethyl)-5-chloro-3-(((trans)-4-(dimethylamino)cyclohexyl)(ethyl)amino)-2-methylbenzamide General PYBOP coupling conditions with 2-(benzo[d]thiazol-2-yl)ethanamine (0.120 g, 40.8% yield).

LCMS: 499.35 (M+1)$^+$; $^1$H NMR (DMSO-d$_6$, 400 MHz) δ 8.53 (m, 1H), 8.07 (d, 1H, J=8 Hz), 7.95 (d, 1H, J=8 Hz), 7.50

(t, 1H J=7.4 Hz), 7.41 (t, 1H, J=7.2 Hz), 7.16 (m, 1H), 7.02 (m, 1H), 3.70-3.66 (m, 2H), 3.38-3.30 (m, 2H), 3.03-3.01 (m, 3H), 2.67 (m, 1H), 2.12 (s, 9H), 1.75-1.73 (m, 4H), 1.37-1.34 (m, 2H), 1.22-1.09 (m, 2H), 0.78 (t, 3H, J=6.8 Hz).

EXAMPLE 14

Synthesis of N-(2-(benzo[d]oxazol-2-yl)ethyl)-5-chloro-3-(((trans)-4-(dimethylamino)cyclohexyl)(ethyl)amino)-2-methylbenzamide

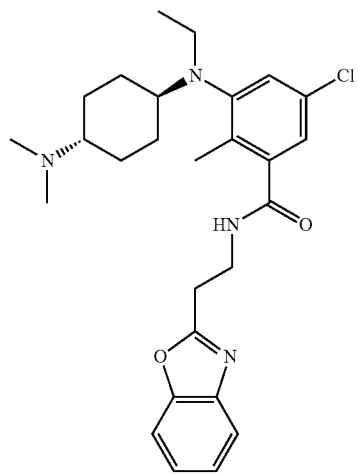

Compound 14

General PYBOP coupling conditions with 2-(benzo[d]oxazol-2-yl)ethanamine (0.050 g, 17.5%).
LCMS: 483.35 (M+1)$^+$; $^1$H NMR (DMSO-d$_6$, 400 MHz) δ 9.26 (bs, 1H), 8.56 (bs, 1H), 7.68-7.66 (m, 2H), 7.36-7.35 (m, 2H), 7.22 (bs, 1H), 7.04 (bs, 1H), 3.70-3.69 (m, 2H), 3.21-3.19 (m, 2H), 3.11-3.03 (m, 3H), 2.69-2.68 (m, 7H), 2.11 (s, 3H), 1.94-1.83 (m, 4H), 1.42 (m, 4H), 0.79 (t, 3H).

EXAMPLE 15

Synthesis of N-((1H-imidazol-2-yl)methyl)-5-chloro-3-(((trans)-4-(dimethylamino)cyclohexyl)(ethyl)amino)-2-methylbenzamide

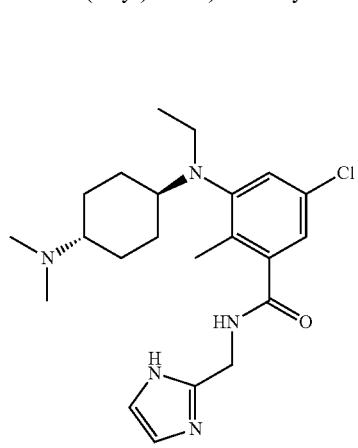

Compound 15

General PYBOP coupling conditions with (1H-imidazol-2-yl)methanamine (0.15 g, 40.7% yield).
LCMS: 418.30 (M+1)$^+$; $^1$H NMR (DMSO-d$_6$, 400 MHz) δ 14.42 (bs, 1H), 9.68 (bs, 1H), 9.19 (s, 1H), 7.62 (s, 2H), 7.36 (s, 1H), 7.29 (s, 1H), 4.68 (d, 2H, J=4.8 Hz), 3.60 (m, 1H), 3.12-3.04 (m, 3H), 2.69-2.68 (m, 6H), 2.19 (s, 3H), 1.96-1.76 (m, 4H), 1.43 (m, 4H), 0.80 (t, 3H, J=6.8 Hz).

EXAMPLE 16

Synthesis of 5-chloro-3-(((tans)-4-(dimethylamino)cyclohexyl)(ethyl)amino)-2-methyl-N-((1-methyl-1H-imidazol-2-yl)methyl)benzamide

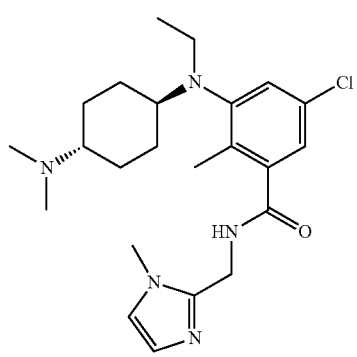

Compound 16

General PYBOP coupling conditions with (1-methyl-1H-imidazol-2-yl)methanamine (0.27 g, 70.7 yield).
LCMS: 432.35 (M+1)$^+$; $^1$H NMR (DMSO-d$_6$, 400 MHz) δ 9.69 (bs, 1H), 9.20 (t, 1H, J=4.4 Hz), 7.68 (s, 1H), 7.63 (s, 1H), 7.29 (s, 2H), 4.72 (d, 2H, J=5.2 Hz), 3.86 (s, 3H), 3.12-3.03 (m, 3H), 2.69-2.68 (m, 7H), 2.17 (s, 3H), 1.96-1.83 (m, 4H), 1.43 (m, 4H), 0.79 (t, 3H, J=6.8 Hz).

EXAMPLE 17

Synthesis of N-((1-benzyl-1H-imidazol-2-yl)methyl)-5-chloro-3-(((1r,4r)-4-(dimethylamino)cyclohexyl)(ethyl)amino)-2-methylbenzamide

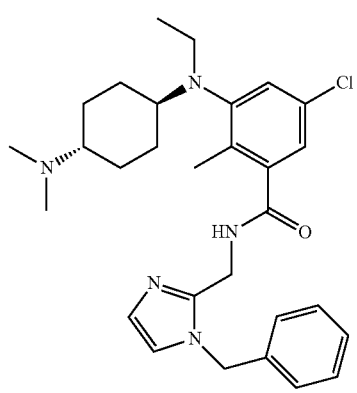

Compound 17

General PYBOP coupling conditions with (1-benzyl-1H-imidazol-2-yl)methanamine (0.12 g, 26.8% yield).
LCMS: 508.45 (M+1)$^+$; $^1$H NMR (DMSO-d$_6$, 400 MHz) δ 9.71 (bs, 1H), 9.19 (t, 1H, J=4.8 Hz), 7.73-7.71 (m, 2H), 7.43-7.27 (m, 6H), 7.06 (s, 1H), 5.49 (s, 2H), 4.79 (d, 2H, J=5.2 Hz), 3.12-3.01 (m, 3H), 2.69-2.68 (m, 7H), 2.14 (s, 3H), 1.96-1.82 (m, 4H), 1.48-1.41 (m, 4H), 0.79 (t, 3H, J=6.8 Hz).

EXAMPLE 18

Synthesis of 5-chloro-3-(((trans)-4-(dimethylamino) cyclohexyl)(ethyl)amino)-N-((1-isopropyl-1H-imidazol-2-yl)methyl)-2-methylbenzamide

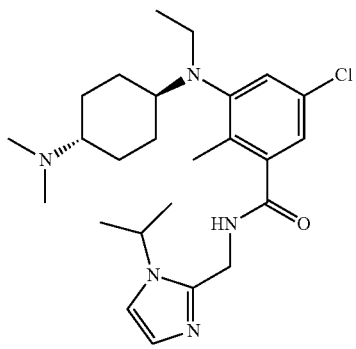

Compound 18

General PYBOP coupling conditions with (1-isopropyl-1H-imidazol-2-yl)methanamine (0.11 g, 27% yield).

LCMS: 460.35 (M+1)$^+$; $^1$H NMR (DMSO-d$_6$, 400 MHz) δ 9.74 (bs, 1H), 9.24 (t, 1H, J=5.2 Hz), 7.94 (s, 1H), 7.72 (s, 1H), 7.29 (s, 1H), 7.25 (s, 1H), 4.84-4.77 (m, 3H), 3.12-3.03 (m, 3H), 2.69-2.68 (m, 7H), 2.17 (s, 3H), 1.96-1.83 (m, 4H), 1.48 (s, 3H), 1.46 (s, 3H), 1.43 (s, 3H), 0.79 (t, 3H, J=6.8 Hz).

EXAMPLE 19

Synthesis of N-((1H-benzo[d]imidazol-2-yl)methyl)-5-chloro-3-(((1r,4r)-4-(dimethylamino)cyclohexyl)(ethyl)amino)-2-methylbenzamide

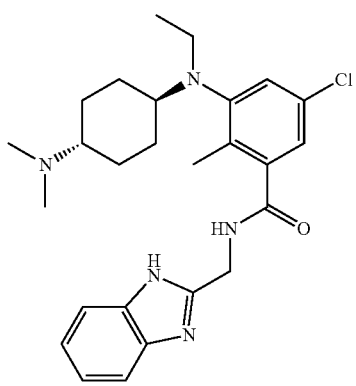

Compound 19

General PYBOP coupling conditions with (1H-benzo[d]imidazol-2-yl)methanamine (0.12 g, 29% yield).

LCMS: 468.35 (M+1)$^+$; $^1$H NMR (DMSO-d$_6$, 400 MHz) δ 9.53 (bs, 1H), 9.33 (t, 1H, J=4.8 Hz), 7.81-7.79 (m, 2H), 7.53-7.51 (m, 2H), 7.43 (s, 1H), 7.31 (s, 1H), 4.87 (d, 2H, J=5.2 Hz), 3.17-3.04 (m, 3H), 2.69-2.68 (m, 7H), 2.21 (s, 3H), 1.96-1.84 (m, 4H), 1.43 (m, 4H), 0.81 (t, 3H, J=6.8 Hz).

EXAMPLE 20

Synthesis of 5-chloro-3-(((trans)-4-(dimethylamino) cyclohexyl)(ethyl)amino)-2-methyl-N-((5-methyl-1H-imidazol-2-yl)methyl)benzamide

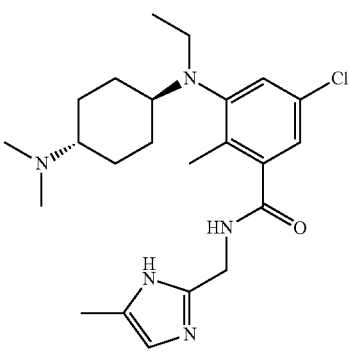

Compound 20

General PYBOP coupling conditions with (5-methyl-1H-imidazol-2-yl)methanamine (0.115 g, 30.2 yield).

LCMS: 432.35 (M+1)$^+$; $^1$H NMR (DMSO-d$_6$, 400 MHz) δ 14.09 (bs, 1H), 9.37 (bs, 1H), 9.14 (t, 1H, J=4.8 Hz), 7.36-7.30 (m, 3H), 4.62 (d, 2H, J=4.8 Hz), 3.12-3.04 (m, 3H), 2.69-2.68 (m, 7H), 2.27 (s, 3H), 2.19 (s, 3H), 1.95-1.83 (m, 4H), 1.43 (m, 4H), 0.80 (t, 3H, J=6.4 Hz).

EXAMPLE 21

Synthesis of N-(2-(1H-benzo[d]imidazol-2-yl)ethyl)-5-chloro-3-(((1r,4r)-4-(dimethylamino)cyclohexyl)(ethyl)amino)-2-methylbenzamide

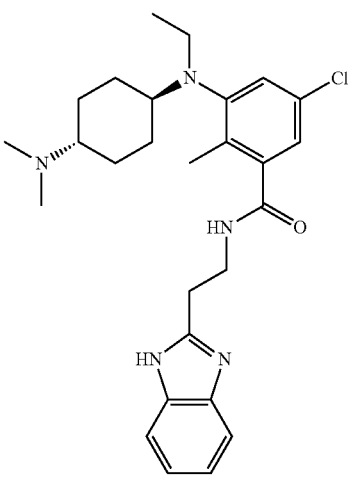

Compound 21

General PYBOP coupling conditions with 2-(1H-benzo[d]imidazol-2-yl)ethanamine (0.11 g, 38.7% yield).

LCMS: 482.40 (M+1)$^+$; $^1$H NMR (DMSO-d$_6$, 400 MHz) δ 14.80 (bs, 1H), 9.55 (bs, 1H), 8.66 (t, 1H), 7.81-7.79 (m, 2H), 7.53-7.51 (m, 2H), 7.22-7.07 (m, 2H), 3.77-3.75 (m, 2H), 3.35-3.32 (m, 2H), 3.17-3.00 (m, 3H), 2.68-2.67 (m, 7H), 2.05 (s, 3H), 1.94-1.79 (m, 4H), 1.41 (m, 4H), 0.76 (t, 3H, J=6.8 Hz).

EXAMPLE 22

Synthesis of 5-chloro-3-(ethyl(tetrahydro-2H-pyran-4-yl)amino)-2-methyl-N-((1-methyl-1H-imidazol-5-yl)methyl)benzamide

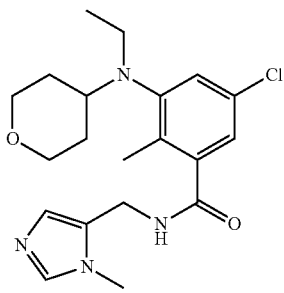

Compound 22

General PYBOP coupling conditions with (1-methyl-1H-imidazol-5-yl)methanamine.

LCMS: 391.3 (M+1)$^+$; $^1$H NMR (MeOD, 400 MHz) β 7.62 (bs, 1H), 7.26 (d, J=1.6 Hz, 1H), 7.08 (d, J=1.6 Hz, 1H), 6.97 (brs, 1H), 4.57 (s, 2H), 3.94-3.90 (m, 2H), 3.75 (s, 3H), 3.35 (dt, J=2.0, 9.2 Hz, 1H), 3.10 (q, J=5.6 Hz, 2H), 3.07-2.95 (m, 1H), 2.26 (s, 3H), 1.73-1.68 (m, 2H), 1.67-1.59 (m, 2H), 0.87 (t, J=5.6 Hz, 3H).

EXAMPLE 23

Synthesis of 5-chloro-3-(ethyl(tetrahydro-2H-pyran-4-yl)amino)-2-methyl-N-((1-methyl-1H-imidazol-2-yl)methyl)benzamide

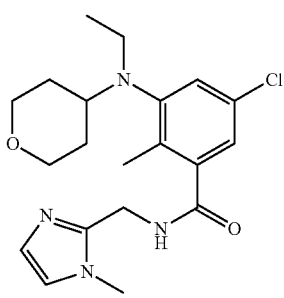

Compound 23

General PYBOP coupling conditions with (1-methyl-1H-imidazol-2-yl)methanamine.

LCMS: 391.3 (M+1)$^+$; $^1$H NMR (MeOD, 400 MHz) δ 7.15 (d, J=1.6 Hz, 1H), 7.04 (d, J=1.6 Hz, 1H), 6.95 (brs, 1H), 6.79 (brs, 1H), 4.51 (s, 2H), 3.83-3.79 (m, 2H), 3.68 (s, 3H), 3.24 (dt, J=2.0, 9.2 Hz, 2H), 2.98 (q, J=5.6 Hz, 2H), 2.95-2.87 (m, 1H), 2.16 (s, 3H), 1.64-1.58 (m, 2H), 1.52 (dq, J=3.2, 9.2 Hz, 2H), 0.76 (t, J=5.6 Hz, 3H).

EXAMPLE 24

Synthesis of 5-chloro-3-(ethyl(tetrahydro-2H-pyran-4-yl)amino)-2-methyl-N-(thiazol-2-ylmethyl)benzamide

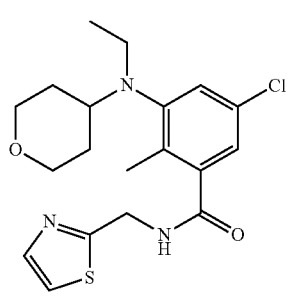

Compound 24

General PYBOP coupling conditions with thiazol-2-yl-methanamine.

LCMS: 394.2 (M+1)$^+$; $^1$H NMR (MeOD, 400 MHz) δ 7.64 (d, J=2.4 Hz, 1H), 7.46 (d, J=2.4 Hz, 1H), 7.18 (d, J=2.0 Hz, 1H), 7.07 (d, J=2.0 Hz, 1H), 4.74 (s, 2H), 3.85-3.80 (m, 2H), 3.26 (dt, J=1.6, 7.6 Hz, 2H), 3.0 (q, J=6.0 Hz, 2H), 2.97-2.90 (m, 1H), 2.22 (s, 3H), 1.64-1.59 (m, 2H), 1.54 (dq, J=3.2, 9.2 Hz, 2H), 0.78 (t, J=5.6 Hz, 3H).

EXAMPLE 25

Synthesis of 5-chloro-3-(ethyl(tetrahydro-2H-pyran-4-yl)amino)-2-methyl-N-((1-methyl-1H-imidazol-4-yl)methyl)benzamide

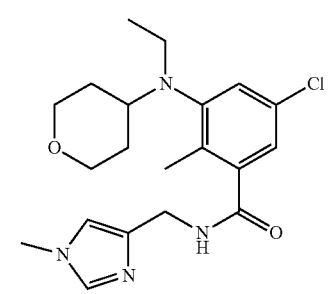

Compound 25

General PYBOP coupling conditions with (1-methyl-1H-imidazol-4-yl)methanamine.

LCMS: 391.3 (M+1)$^+$; $^1$H NMR (MeOD, 400 MHz) δ 7.45 (brs, 1H), 7.14 (d, J=1.6 Hz, 1H), 7.02 (d, J=1.6 Hz, 1H), 6.94 (brs, 1H), 4.32 (s, 2H), 3.84-3.79 (m, 2H), 3.60 (s, 3H), 3.21

(quin, J=1.6 Hz, 2H), 2.99 (q, J=5.6 Hz, 2H), 2.96-2.88 (m, 1H), 2.27 (s, 3H), 1.64-1.58 (m, 2H), 1.52 (dq, J=3.2, 10.0 Hz, 2H), 0.76 (t, J=5.6 Hz, 3H).

EXAMPLE 26

Synthesis of 5-chloro-3-(ethyl(tetrahydro-2H-pyran-4-yl)amino)-N-(imidazo[2,1-b]thiazol-6-ylmethyl)-2-methylbenzamide

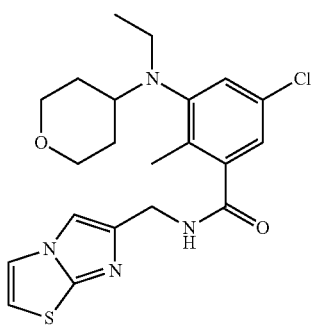

Compound 26

General PYBOP coupling conditions with imidazo[2,1-b]thiazol-6-ylmethanamine.

LCMS: 433.1 (M+1)$^+$; $^1$H NMR (MeOD, 400 MHz) δ 7.60 (d, J=3.6 Hz, 1H), 7.55 (s, 1H), 7.13 (d, J=1.6 Hz, 1H), 7.05 (d, J=1.6 Hz, 1H), 6.99 (d, J=3.6 Hz, 1H), 4.44 (s, 3H), 3.79 (brd, J=9.2 Hz, 2H), 3.23-3.18 (m, 2H), 2.97 (q, J=5.6 Hz, 2H), 2.94-2.87 (m, 1H), 2.18 (s, 3H), 1.58 (brd, J=5.6 Hz, 2H), 1.50 (dq, J=3.2, 9.2 Hz, 2H), 0.75 (t, J=5.6 Hz, 3H).

EXAMPLE 27

Synthesis of 5-chloro-N-((1,5-dimethyl-1H-pyrazol-4-yl)methyl)-3-(ethyl(tetrahydro-2H-pyran-4-yl)amino)-2-methylbenzamide Compound 27

General PYBOP coupling conditions with (1,5-dimethyl-1H-pyrazol-4-yl)methanamine.

LCMS: 405.3 (M+1)$^+$; $^1$H NMR (MeOD, 400 MHz) δ 7.7.42 (s, 1H), 7.25 (d, J=1.6 Hz, 1H), 7.04 (d, J=1.6 Hz, 1H), 4.36 (s, 2H), 3.93 (brdd, J=1.6, 6.8 Hz, 2H), 3.78 (s, 3H), 3.36

(dt, J=2.0, 9.2 Hz, 2H), 3.10 (q, J=5.6 Hz, 2H), 2.35 (s, 3H), 2.25 (s, 3H), 1.75-1.69 (m, 2H), 1.64 (dq, J=3.2, 9.2 Hz, 2H), 0.88 (t, J=5.6 Hz, 3H).

EXAMPLE 28

Synthesis of 5-chloro-3-(ethyl(tetrahydro-2H-pyran-4-yl)amino)-2-methyl-N-((1-methyl-1H-pyrazol-3-yl)methyl)benzamide

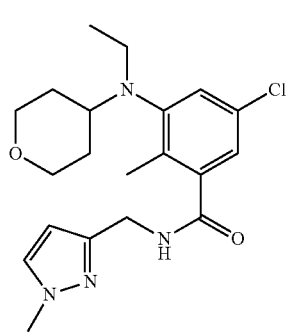

Compound 28

General PYBOP coupling conditions with (1-methyl-1H-pyrazol-3-yl)methanamine.

LCMS: 391.2 (M+1)$^+$; $^1$H NMR (MeOD, 400 MHz) δ 7.41 (d, J=1.6 Hz, 1H), 7.14 (d, J=1.6 Hz, 1H), 7.00 (d, J=1.6 Hz, 1H), 6.16 (d, J=1.6 Hz, 1H), 4.39 (s, 2H), 3.80 (brd, J=5.6 Hz, 2H), 3.74 (s, 3H), 3.24 (brt, J=8.0 Hz, 2H), 2.98 (q, J=5.6 Hz, 2H), 2.96-2.89 (m, 1H), 2.17 (s, 3H), 1.60 (brd, J=9.2 Hz, 2H), 1.51 (dq, J=3.2, 9.2 Hz, 2H), 0.76 (t, J=5.6 Hz, 3H).

EXAMPLE 29

Synthesis of 5-chloro-3-(ethyl(tetrahydro-2H-pyran-4-yl)amino)-2-methyl-N-((5-methylisoxazol-3-yl)methyl)benzamide

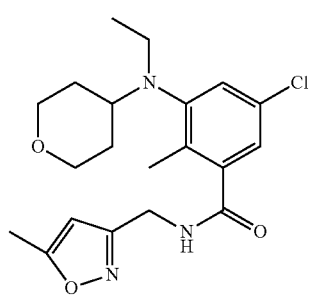

Compound 29

General PYBOP coupling conditions with (5-methylisoxazol-3-yl)methanamine.

LCMS: 392.3 (M+1)$^+$; $^1$H NMR (MeOD, 400 MHz) δ 7.15 (d, J=1.6 Hz, 1H), 7.03 (d, J=2.0 Hz, 1H), 6.06 (s, 1H), 4.75 (brs, 3H), 3.80 (brd, J=5.6 Hz, 2H), 3.24 (t, J=9.6 Hz, 2H), 2.98 (q, J=5.6 Hz, 2H), 2.96-2.89 (m, 1H), 2.31 (s, 3H), 2.18 (s, 3H), 1.60 (brd, J=9.2 Hz, 2H), 1.51 (dq, J=3.2, 9.2 Hz, 2H), 0.76 (t, J=5.6 Hz, 3H).

EXAMPLE 30

Synthesis of N-((1H-imidazol-4-yl)methyl)-5-chloro-3-(ethyl(tetrahydro-2H-pyran-4-yl)amino)-2-methylbenzamide Compound 30

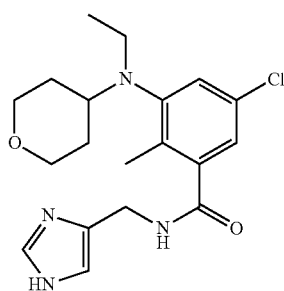

General PYBOP coupling conditions with (1H-imidazol-4-yl)methanamine.

LCMS: 377.3 (M+1)$^+$; $^1$H NMR (MeOD, 400 MHz) δ 7.54 (brs, 1H), 7.14 (d, J=1.6 Hz, 1H), 7.02 (d, J=1.6 Hz, 1H), 6.95 (brs, 1H), 4.38 (s, 2H), 3.81 (brd, J=9.6 Hz, 2H), 3.24 (dt, J=1.6, 9.2 Hz, 2H), 2.98 (q, J=5.6 Hz, 2H), 2.96-2.88 (m, 1H), 2.16 (s, 3H), 1.60 (brdd, J=1.2, 9.6 Hz, 2H), 1.52 (dq, J=3.6, 9.2 Hz, 2H), 0.76 (t, J=5.6 Hz, 3H).

EXAMPLE 31

Synthesis of 5-chloro-N-((1,3-dimethyl-1H-pyrazol-5-yl)methyl)-3-(ethyl(tetrahydro-2H-pyran-4-yl)amino)-2-methylbenzamide Compound 31

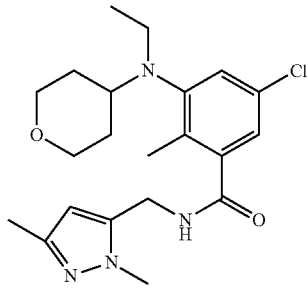

General PYBOP coupling conditions with (1,3-dimethyl-1H-pyrazol-5-yl)methanamine.

LCMS: 405.3 (M+1)$^+$; $^1$H NMR (MeOD, 400 MHz) δ 7.28 (d, J=2.0 Hz, 1H), 7.10 (d, j=2.0 Hzm 1H), 6.09 (s, 1H), 4.56 (s, 2H), 3.94 (brd, J=8.4 Hz, 2H), 3.84 (s, 3H), 3.37 (dt, J=2.0, 9.6 Hz, 2H), 3.11 (q, J=5.6 Hz, 2H), 3.09-3.01 (m, 1H), 2.28 (s, 3H), 2.21 (s, 3H), 1.73 (brd, J=9.2 Hz, 2H), 1.64 (dq, J=3.6, 9.2 Hz, 2H), 0.89 (t, J=5.6 Hz, 3H).

EXAMPLE 32

Bioassay Protocol and General Methods

Protocol for Wild-Type and Mutant PRC2 Enzyme Assays

General Materials. S-adenosylmethionine (SAM), S-adenosylhomocyteine (SAH), bicine, KCl, Tween20, dimethylsulfoxide (DMSO) and bovine skin gelatin (BSG) were purchased from Sigma-Aldrich at the highest level of purity possible. Dithiothreitol (DTT) was purchased from EMD Millipore. $^3$H-SAM was purchased from American Radiolabeled Chemicals with a specific activity of 80 Ci/mmol. 384-well streptavidin Flashplates were purchased from PerkinElmer.

Substrates. Peptides representative of human histone H3 residues 21- 44 containing either an unmodified lysine 27 (H3K27me0) or dimethylated lysine 27 (H3K27me2) are synthesized with a C-terminal G(K-biotin) linker-affinity tag motif and a C-terminal amide cap by 21$^{st}$ Century Biochemicals. The peptides are high-performance liquid chromatography (HPLC) purified to greater than 95% purity and confirmed by liquid chromatography mass spectrometry (LC-MS). The sequences are listed below.

```
H3K27me0:
                                        (SEQ ID NO: 1)
ATKAARKSAPATGGVKKPHRYRPGGK(biotin)-amide H3K27me2:
                                        (SEQ ID NO: 2)
ATKAARK(me2)SAPATGGVKKPHRYRPGGK(biotin)-amide
```

Chicken erythrocyte oligonucleosomes were purified from chicken blood according to established procedures.

Recombinant PRC2 Enzymes. Human PRC2 enzymes were purified as 4-component enzyme complexes co-expressed in *Spodoptera frugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates. The assays were all performed in a buffer consisting of 20 mM bicine (pH=7.6), 0.5 mM DTT, 0.005% BSG and 0.002% Tween20, prepared on the day of use. Compounds in 100% DMSO (1 µL) were spotted into polypropylene 384-well V-bottom plates (Greiner) using a Platemate 2×3 outfitted with a 384-channel pipet head (Thermo). DMSO (1 µL) was added to columns 11, 12, 23, 24, rows A -H for the maximum signal control, and SAH, a known product and inhibitor of PRC2 (1 µL) was added to columns 11,12, 23, 24, rows I -P for the minimum signal control. A cocktail (40 µL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 min at 25° C., then a cocktail (10 µL) containing a mixture of non-radioactive and $^3$H-SAM was added to initiate the reaction (final volume=51 µL). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 3, below. The assays were stopped by the addition of non-radioactive SAM (10 µL) to a final concentration of 600 µM, which dilutes the $^3$H-SAM to a level where its incorporation into the peptide substrate is no longer detectable. 50 µL of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^3$H-labeled peptide bound to the Flashplate surface, measured as disintegrations per minute (dpm) or alternatively, referred to as counts per minute (cpm).

TABLE 3

Final concentrations of components for each assay variation based upon EZH2 identity (wild-type or Y641 mutant EZH2)

| PRC2 Enzyme (denoted by EZH2 identity) | Peptide (nM) | Non-radioactive SAM (nM) | $^3$H-SAM (nM) |
|---|---|---|---|
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate. The assays was performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 µL) were spotted into polypropylene 384-well V-bottom plates (Greiner) using a Platemate 2×3 outfitted with a 384-channel pipet head (Thermo). DMSO (1 µL) was added to columns 11, 12, 23, 24, rows A -H for the maximum signal control, and SAH, a known product and inhibitor of PRC2 (1 µL) was added to columns 11,12, 23, 24, rows I -P for the minimum signal control. A cocktail (40 µL) containing the wild-type PRC2 enzyme and chicken erythrocyte oligonucleosome was added by Multidrop Combi (Thermo). The compounds were allowed to incubate with PRC2 for 30 min at 25° C., then a cocktail (10 µL) containing a mixture of non-radioactive and $^3$H-SAM was added to initiate the reaction (final volume=51 µL). The final concentrations were as follows: wild-type PRC2 enzyme was 4 nM, non-radioactive SAM was 430 nM, $^3$H-SAM was 120 nM, chicken erythrocyte olignonucleosome was 120 nM, SAH in the minimum signal control wells was 1 mM and the DMSO concentration was 1%. The assay was stopped by the addition of non-radioactive SAM (10 µL) to a final concentration of 600 µM, which dilutes the $^3$H-SAM to a level where its incorporation into the chicken erythrocyte olignonucleosome substrate is no longer detectable. 50 µL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek ELx405 plate washer. The plates were then read in a PerkinElmer TopCount platereader to measure the quantity of $^3$H-labeled chicken erythrocyte oligonucleosome bound to the Flashplate surface, measured as disintegrations per minute (dpm) or alternatively, referred to as counts per minute (cpm).

% Inhibition Calculation $$\% \ inh = 100 - \left( \frac{dpm_{cpmd} - dpm_{min}}{dpm_{max} - dpm_{min}} \right) \times 100$$

Where dpm=disintegrations per minute, cmpd=signal in assay well, and min and max are the respective minimum and maximum signal controls.

Four-parameter $IC_{50}$ fit $$Y = \text{Bottom} + \frac{(\text{Top} - \text{Bottom})}{1 + \left( \frac{X}{IC_{50}} \right)^{\text{Hill Coefficient}}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

$IC_{50}$ values for the PRC2 enzyme assays on peptide substrates (e.g., EZH2 wild type) are presented in Table 4 below.

WSU-DLCL2 Methylation Assay

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum, and D-PBS were purchased from Life Technologies, Grand Island, N.Y., USA. Extraction Buffer and Neutralization Buffer(5×) were purchased from Active Motif, Carlsbad, Calif., USA. Rabbit anti-Histone H3 antibody was purchased from Abcam, Cambridge, Mass., USA. Rabbit anti-H3K27me3 and HRP-conjugated anti-rabbit-IgG were purchased from Cell Signaling Technology, Danvers, Mass., USA. TMB "Super Sensitive" substrate was sourced from BioFX Laboratories, Owings Mills, Md., USA. IgG-free Bovine Serum Albumin was purchased from Jackson ImmunoResearch, West Grove, Pa., USA. PBS with Tween (10× PBST) was purchased from KPL, Gaithersburg, Md., USA. Sulfuric Acid was purchased from Ricca Chemical, Arlington, Tex., USA. Immulon ELISA plates were purchased from Thermo, Rochester, N.Y., USA. V-bottom cell culture plates were purchased from Corning Inc., Corning, N.Y., USA. V-bottom polypropylene plates were purchased from Greiner Bio-One, Monroe, N.C., USA.

WSU-DLCL2 suspension cells were maintained in growth medium (RPMI 1640 supplemented with 10% v/v heat inactivated fetal bovine serum and 100 units/mL penicillin-streptomycin) and cultured at 37° C. under 5% $CO_2$ Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$ on a plate shaker.

WSU-DLCL2 cells were seeded in assay medium at a concentration of 50,000 cells per mL to a 96-well V-bottom cell culture plate with 200 µL per well. Compound (1 µL) from 96 well source plates was added directly to V-bottom cell plate. Plates were incubated on a titer-plate shaker at 37° C., 5% $CO_2$ for 96 hours. After four days of incubation, plates were spun at 241×g for five minutes and medium was aspirated gently from each well of cell plate without disturbing cell pellet. Pellet was resuspended in 200 µL DPBS and plates were spun again at 241×g for five minutes. The supernatant was aspirated and cold (4° C.) Extraction buffer (100 µL) was added per well. Plates were incubated at 4° C. on orbital shaker for two hours. Plates were spun at 3427×g×10 minutes. Supernatant (80 µL per well) was transferred to its respective well in 96 well V-bottom polypropylene plate. Neutralization Buffer 5× (20 µL per well) was added to V-bottom polypropylene plate containing supernatant. V-bottom polypropylene plates containing crude histone preparation (CHP) were incubated on orbital shaker×five minutes. Crude Histone Preparations were added (2 µL per well) to each respective well into duplicate 96 well ELISA plates containing 100 µL Coating Buffer (1×PBS+BSA 0.05% w/v). Plates were sealed and incubated overnight at 4° C. The following day, plates were washed three times with 300 µL per well 1×PBST. Wells were blocked for two hours with 300 µL per well ELISA Diluent ((PBS (1×) BSA (2% w/v) and Tween20 (0.05% v/v)). Plates were washed three times with 1×PBST. For the Histone H3 detection plate, 100 µL per well were added of anti-Histone-H3 antibody (Abcam, ab1791) diluted 1:10,000 in ELISA Diluent. For H3K27 trimethylation detection plate, 100 µL per well were added of anti-H3K27me3 diluted 1:2000 in ELISA diluent. Plates were incubated for 90 minutes at room temperature. Plates were washed three times with 300 µL 1×PBST per well. For Histone H3 detection, 100 µL of HRP-conjugated anti-rabbit IgG antibody diluted to 1:6000 in ELISA diluent was added per well. For H3K27me3 detection, 100 µL of HRP conjugated anti-rabbit IgG antibody diluted to 1:4000 in ELISA diluent was added per well. Plates were incubated at room temperature for 90 minutes. Plates were washed four times with 1×PBST 300 µL per well. TMB substrate 100 µL was added per well. Histone H3 plates were incubated for five minutes at room temperature. H3K27me3 plates were incubated for 10 minutes at room temperature. The reaction was stopped with sulfuric acid 1N (100 µL per well). Absorbance for each plate was read at 450 nm.

First, the ratio for each well was determined by:

$$\left(\frac{H3K27me3\,OD450\text{ value}}{Histone\,H3\,OD450\text{ value}}\right)$$

Each plate included eight control wells of DMSO only treatment (Minimum Inhibition) as well as eight control wells for maximum inhibition (Background wells).

The average of the ratio values for each control type was calculated and used to determine the percent inhibition for each test well in the plate. Test compound was serially diluted three-fold in DMSO for a total of ten test concentrations, beginning at 25 µM. Percent inhibition was determined and $IC_{50}$ curves were generated using duplicate wells per concentration of compound.

$$\text{Percent Inhibition} = 100 - \left(\left(\frac{\text{(Individual Test Sample Ratio)} - \text{(Background Avg Ratio)}}{\text{(Minimum Inhibition Ratio)} - \text{(Background Average Ratio)}}\right) * 100\right)$$

Cell Proliferation Analysis

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum were purchased from Life Technologies, Grand Island, N.Y., USA. V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

WSU-DLCL2 suspension cells were maintained in growth medium (RPMI 1640 supplemented with 10% v/v heat inactivated fetal bovine serum and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$.

For the assessment of the effect of compounds on the proliferation of the WSU-DLCL2 cell line, exponentially growing cells were plated in 384-well white opaque plates at a density of 1250 cell/ml in a final volume of 50 µl of assay medium. A compound source plate was prepared by performing triplicate nine-point 3-fold serial dilutions in DMSO, beginning at 10 mM (final top concentration of compound in the assay was 20 µM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 6 days at 37° C., 5% $CO_2$, relative humidity>90% for 6 days. Cell viability was measured by quantization of ATP present in the cell cultures, adding 35 µl of Cell Titer Glo® reagent to the cell plates. Luminescence was read in the SpectraMax M5. The concentration inhibiting cell viability by 50% was determined using a 4-parametric fit of the normalized dose response curves. $IC_{50}$ values for this assay are also presented in Table 4 below.

TABLE 4

| Cpd # | WT EZH2 $IC_{50}$ (µM) | WSU proliferation $IC_{50}$ (µM) |
|---|---|---|
| 1 | 0.433 | >25 |
| 2 | 1.38 | >25 |
| 3 | 2.18 | >25 |
| 4 | 5.13 | — |
| 5 | >10 | — |
| 6 | >10 | — |
| 7 | >10 | — |
| 8 | 12.16 | — |
| 9 | 1.65 | — |
| 10 | 2.03 | >50 |
| 11 | >50 | — |
| 12 | >50 | — |
| 13 | 37.65 | — |
| 14 | 6.55 | — |
| 15 | >10 | — |
| 16 | 3.11 | — |
| 17 | 2.99 | — |
| 18 | >10 | — |
| 19 | >10 | — |
| 20 | >10 | — |
| 21 | 37.08 | — |
| 22 | >50.0 | >50.0 |
| 23 | 23.69 | >50.0 |
| 24 | >50.0 | >50.0 |
| 25 | 7.82 | >50.0 |
| 26 | >50.0 | >50.0 |
| 27 | >50.0 | >50.0 |
| 28 | 14.83 | >50.0 |

TABLE 4-continued

| Cpd # | WT EZH2 IC$_{50}$ (µM) | WSU proliferation IC$_{50}$ (µM) |
|---|---|---|
| 29 | >50.0 | >50.0 |
| 30 | 0.32 | 44.10 |
| 31 | >50.0 | >50.0 |

EXAMPLE 33

Derivation of the Lowest Cytotoxic Concentration (LCC)

It is well established that cellular proliferation proceeds through cell division that results in a doubling of the number of cells after division, relative to the number of cells prior to division. Under a fixed set of environmental conditions (e.g., pH, ionic strength, temperature, cell density, medium content of proteins and growth factors, and the like) cells will proliferate by consecutive doubling (i.e., division) according to the following equation, provided that sufficient nutrients and other required factors are available.

$$N_t = N_0 \times 2^{\frac{t}{t_D}} \quad (A.1)$$

where $N_t$ is the cell number at a time point (t) after initiation of the observation period, $N_0$ is the cell number at the initiation of the observation period, t is the time after initiation of the observation period and $t_D$ is the time interval required for cell doubling, also referred to as the doubling time. Equation A.1 can be converted into the more convenient form of an exponential equation in base e, taking advantage of the equality, 0.693=ln(2).

$$N_t = N_0 e^{\frac{0.693 t}{t_D}} \quad (A.2)$$

The rate constant for cell proliferation ($k_p$) is inversely related to the doubling time as follows.

$$k_p = \frac{0.693}{t_D} \quad (A.3)$$

Combining equation A.2 and A.3 yields, $$N_t = N_0 e^{k_p t} \quad (A.4)$$

Thus, according to equation A.4 cell number is expected to increase exponentially with time during the early period of cell growth referred to as log-phase growth. Exponential equations like equation A.4 can be linearized by taking the natural logarithm of each side.

$$\ln(N_t) = \ln(N_0) + k_p t \quad (A.5)$$

Thus a plot of $\ln(N_t)$ as a function of time is expected to yield an ascending straight line with slope equal to $k_p$ and y-intercept equal to $\ln(N_0)$.

Changes in environmental conditions can result in a change in the rate of cellular proliferation that is quantifiable as changes in the proliferation rate constant $k_p$. Among conditions that may result in a change in proliferation rate is the introduction to the system of an antiproliferative compound at the initiation of the observation period (i.e., at t=0). When an antiproliferative compound has an immediate impact on cell proliferation, one expects that plots of $\ln(N_t)$ as a function of time will continue to be linear at all compound concentrations, with diminishing values of $k_p$ at increasing concentrations of compound.

Depending on the mechanistic basis of antiproliferative action, some compounds may not immediately effect a change in proliferation rate. Instead, there may be a period of latency before the impact of the compound is realized. In such cases a plot of $\ln(N_t)$ as a function of time will appear biphasic, and a time point at which the impact of the compound begins can be identified as the breakpoint between phases. Regardless of whether a compound's impact on proliferation is immediate or begins after a latency period, the rate constant for proliferation at each compound concentration is best defined by the slope of the $\ln(N_t)$ vs. time curve from the time point at which compound impact begins to the end of the observation period of the experiment.

A compound applied to growing cells may affect the observed proliferation in one of two general ways: by inhibiting further cell division (cytostasis) or by cell killing (cytotoxicity). If a compound is cytostatic, increasing concentration of compound will reduce the value of $k_p$ until there is no further cell division. At this point, the rate of cell growth, and therefore the value of $k_p$, will be zero. If, on the other hand, the compound is cytotoxic, then the value of $k_p$ will be composed of two rate constants: a rate constant for continued cell growth in the presence of the compound ($k_g$) and a rate constant for cell killing by the compound ($k_d$). The overall rate constant for proliferation at a fixed concentration of compound will thus be the difference between the absolute values of these opposing rate constants.

$$k_p = |k_g| - |k_d| \quad (A.6)$$

At compound concentrations for which the rate of cell growth exceeds that of cell killing, the value of $k_p$ will have a positive value (i.e., $k_p > 0$). At compound concentrations for which the rate of cell growth is less than that for cell killing, the value of $k_p$ will have a negative value (i.e., $k_p < 0$) and the cell number will decrease with time, indicative of robust cytotoxicity. When $k_g$ exactly matches $k_d$ then the overall proliferation rate constant, $k_p$, will have a value of zero. We can thus define the lowest cytotoxic concentration (LCC) as that concentration of compound that results in a value of $k_p$ equal to zero, because any concentration greater than this will result in clearly observable cytotoxicity. Nota bene: at concentrations below the LCC there is likely to be cell killing occurring, but at a rate that is less than that of residual cell proliferation. The treatment here is not intended to define the biological details of compound action. Rather, the goal here is to merely define a practical parameter with which to objectively quantify the concentration of compound at which the rate of cell killing exceeds new cell growth. Indeed, the LCC represents a breakpoint or critical concentration above which frank cytotoxicity is observed, rather than a cytotoxic concentration per se. In this regard, the LCC can be viewed similar to other physical breakpoint metrics, such as the critical micelle concentration (CMC) used to define the concentration of lipid, detergent or other surfactant species above which all molecules incorporate into micellar structures.

Traditionally, the impact of antiproliferative compounds on cell growth has been most commonly quantified by the IC$_{50}$ value, which is defined as that concentration of compound that reduces the rate of cell proliferation to one half that observed in the absence of compound (i.e., for the vehicle or solvent control sample). The $IC_{50}$, however, does not allow the investigator to differentiate between cytostatic and cytotoxic compounds. The LCC, in contrast, readily allows one to make such a differentiation and to further quantify the concentration at which the transition to robust cytotoxic behavior occurs.

If one limits the observation time window to between the start of impact and the end of the experiment, then the data will generally fit well to a linear equation when plotted as $\ln(N_t)$ as a function of time (vide supra). From fits of this type, the value of $k_p$ can be determined at each concentration of compound tested. A replot of the value of $k_p$ as a function of compound concentration ([I]) will have the form of a descending isotherm, with a maximum value at [I]=0 of $k_{max}$ (defined by the vehicle or solvent control sample) and a minimum value at infinite compound concentration of $k_{min}$.

$$k_p = \frac{(k_{max} - k_{min})}{1 + \frac{[I]}{I_{mid}}} + k_{min} \quad (A.7)$$

where $I_{mid}$ is the concentration of compound yielding a value of $k_p$ that is midway between the values of $k_{max}$ and $k_{min}$ (note that the value of $I_{mid}$ is not the same as the $IC_{50}$, except in the case of a complete and purely cytostatic compound). Thus, fitting the replot data to equation A.7 provides estimates of $k_{max}$, $k_{min}$ and $I_{mid}$. If a compound is cytostatic (as defined here), the value of $k_{min}$ cannot be less than zero. For cytotoxic compounds, $k_{min}$ will be less than zero and the absolute value of $k_{min}$ will relate directly to the effectiveness of the compound in killing cells.

The fitted values derived from equation A.7 can also be used to determine the value of the LCC. By definition, when [I]=LCC, $k_p$=0. Thus, under these conditions equation A.7 becomes.

$$0 = \frac{(k_{max} - k_{min})}{1 + \frac{LCC}{I_{mid}}} + k_{min} \quad (A.8)$$

Algebraic rearrangement of equation A.8 yields an equation for the LCC.

$$LCC = I_{mid}\left[\left(\frac{k_{max} - k_{min}}{-k_{min}}\right) - 1\right] \quad (A.9)$$

This analysis is simple to implement with nonlinear curve fitting software and may be applied during cellular assays of compound activity throughout the drug discovery and development process. In this manner, the LCC may provide a valuable metric for the assessment of compound SAR (structure-activity relationship).

EXAMPLE 34

In vivo Assays

Mice

Female Fox Chase SCID® Mice (CB17/Icr-Prkdc$_{scid}$/IcrI-coCrl, Charles River Laboratories) or athymic nude mice (Crl:NU(Ncr)-Foxn1$_{nu}$, Charles River Laboratories) are 8 weeks old and had a body-weight (BW) range of 16.0-21.1 g on D1 of the study. The animals are fed ad libitum water (reverse osmosis 1 ppm Cl) and NIH 31 Modified and Irradiated Lab Diet® consisting of 18.0% crude protein, 5.0% crude fat, and 5.0% crude fiber. The mice are housed on irradiated Enrich-O'Cobs™ bedding in static microisolators on a 12-hour light cycle at 20-22° C. (68-72° F.) and 40-60% humidity. All procedures comply with the recommendations of the *Guide for Care and Use of Laboratory Animals* with respect to restraint, husbandry, surgical procedures, feed and fluid regulation, and veterinary care.

Tumor Cell Culture

Human lymphoma cell lines line are obtained from different sources (ATCC, DSMZ), e.g., WSU-DLCL2 obtained from DSMZ. The cell lines are maintained at Piedmont as suspension cultures in RPMI-1640 medium containing 100 units/mL penicillin G sodium salt, 100 g/mL streptomycin, and 25 g/mL gentamicin. The medium is supplemented with 10% fetal bovine serum and 2 mM glutamine. The cells are cultured in tissue culture flasks in a humidified incubator at 37° C., in an atmosphere of 5% $CO_2$ and 95% air.

In Vivo Tumor Implantation

Human lymphoma cell lines, e.g., WSU-DLCL2 cells, are harvested during mid-log phase growth, and re-suspended in PBS with 50% Matrigeff (BD Biosciences). Each mouse receives $1\times10^7$ cells (0.2 mL cell suspension) subcutaneously in the right flank. Tumors are calipered in two dimensions to monitor growth as the mean volume approached the desired 80-120 mm$^3$ range. Tumor size, in mm$^3$, is calculated from:

$$\text{Tumor volume} = \frac{w^2 \times l}{2}$$

where w=width and l=length, in mm, of the tumor. Tumor weight can be estimated with the assumption that 1 mg is equivalent to 1 mm$_3$ of tumor volume. After 10-30 days mice with 108-126 mm$^3$ tumors are sorted into treatment groups with mean tumor volumes of 117-119 mm$^3$.

Test Articles

Test compounds are stored at room temperature and protected from light. On each treatment day, fresh compound formulations are prepared by suspending the powders in 0.5% sodium carboxymethylcellulose (NaCMC) and 0.1% Tween® 80 in deionized water. Compound 141 (free base) is dissolved in sterile saline and the pH is adjusted to 4.5 with HCl fresh every day. The vehicles, 0.5% NaCMC and 0.1% Tween® 80 in deionized water or sterile saline pH 4.5, are used to treat the control groups at the same schedules. Formulations are stored away from light at 4° C. prior to administration. Unless otherwise specified, compounds referred to and tested in this experiment are in their specific salt forms mentioned in this paragraph.

Treatment Plan

Mice are treated at compound doses ranging from 12.5-600 mg/kg and at TID (three time a day every 8 h), BID (2 times a day every 12 h) or QD (once a day) schedules for various amounts of days by oral gavage or injections via the intraperitoneal route. Each dose is delivered in a volume of 0.2 mL/20 g mouse (10 mL/kg), and adjusted for the last recorded weight of individual animals. The maximal treatment length is 28 days.

Median Tumor Volume (MTV) and Tumor Growth Inhibition (TGI) Analysis

Treatment efficacy is determined on the last treatment day. MTV(n), the median tumor volume for the number of animals, n, evaluable on the last day, is determined for each group. Percent tumor growth inhibition (% TGI) can be defined several ways. First, the difference between the MTV(n) of the designated control group and the MTV(n) of the drug-treated group is expressed as a percentage of the MTV(n) of the control group:

$$\% \ TGI = \left( \frac{MTV(n)_{control} - MTV(n)_{treated}}{MTV(n)_{control}} \right) \times 100$$

Another way of calculating % TGI is taking the change of the tumor size from day 1 to day n into account with n being the last treatment day.

$$\% \ TGI = \left( \frac{\Delta MTV_{control} - \Delta MTV_{treated}}{\Delta MTV_{control}} \right) \times 100$$

$$\Delta MTV_{control} = MTV(n)_{control} - MTV(1)_{control}$$

$$\Delta MTV_{treated} = MTV(n)_{treated} - MTV(1)_{treated}$$

Toxicity

Animals are weighed daily on Days 1-5, and then twice weekly until the completion of the study. The mice are examined frequently for overt signs of any adverse, treatment related side effects, which are documented. Acceptable toxicity for the maximum tolerated dose (MTD) is defined as a group mean BW loss of less than 20% during the test, and not more than 10% mortality due to TR deaths. A death is to be classified as TR if it is attributable to treatment side effects as evidenced by clinical signs and/or necropsy, or due to unknown causes during the dosing period. A death is to be classified as NTR if there is evidence that the death is unrelated to treatment side effects. NTR deaths during the dosing interval would typically be categorized as NTRa (due to an accident or human error) or NTRm (due to necropsy-confirmed tumor dissemination by invasion and/or metastasis). Orally treated animals that die from unknown causes during the dosing period may be classified as NTRu when group performance does not support a TR classification and necropsy, to rule out a dosing error, is not feasible.

Sampling

On days 7 or 28 during the studies mice are sampled in a pre-specified fashion to assess target inhibition in tumors. Tumors are harvested from specified mice under RNAse free conditions and bisected. Frozen tumor tissue from each animal is snap frozen in liquid $N_2$ and pulverized with a mortar and pestle.

Statistical and Graphical Analyses

All statistical and graphical analyses are performed with Prism 3.03 (GraphPad) for Windows. To test statistical significance between the control and treated groups over the whole treatment time course a repeated measures ANOVA test followed by Dunnets multiple comparison post test or a 2 way ANOVA test are employed. Prism reports results as non-significant (ns) at $P>0.05$, significant (symbolized by "*") at $0.01<P<0.05$, very significant ("") at $0.001<P<0.01$ and extremely significant ("*") at $P<0.001$.

Histone Extraction

For isolation of histones, 60-90 mg tumor tissue is homogenized in 1.5 ml nuclear extraction buffer (10 mM Tris-HCl, 10 mM $MgCl_2$, 25 mM KCl, 1% Triton X-100, 8.6% Sucrose, plus a Roche protease inhibitor tablet 1836145) and incubated on ice for 5 minutes. Nuclei are collected by centrifugation at 600 g for 5 minutes at 4° C. and washed once in PBS. Supernatant is removed and histones extracted for one hour, with vortexing every 15 minutes, with 0.4 N cold sulfuric acid. Extracts are clarified by centrifugation at 10,000 g for 10 minutes at 4° C. and transferred to a fresh microcentrifuge tube containing 10× volume of ice cold acetone. Histones are precipitated at −20° C. for 2 hours-overnight, pelleted by centrifugation at 10,000 g for 10 minutes, and resuspended in water.

ELISA

Histones are prepared in equivalent concentrations in coating buffer (PBS+0.05% BSA) yielding 0.5 ng/ul of sample, and 100 ul of sample or standard is added in duplicate to 2 96-well ELISA plates (Thermo Labsystems, Immulon 4HBX #3885). The plates are sealed and incubated overnight at 4° C. The following day, plates are washed 3× with 300 ul/well PBST (PBS+0.05% Tween 20; 10×PBST, KPL #51-14-02) on a Bio Tek plate washer. Plates are blocked with 300 ul/well of diluent (PBS+2% BSA+0.05% Tween 20), incubated at RT for 2 hours, and washed 3× with PBST. All antibodies are diluted in diluent. 100 ul/well of anti-H3K27me3 (CST #9733, 50% glycerol stock 1:1,000) or anti-total H3 (Abcam ab1791, 50% glycerol 1:10,000) is added to each plate. Plates are incubated for 90 min at RT and washed 3× with PBST. 100 ul/well of anti-Rb-IgG-HRP (Cell Signaling Technology, 7074) is added 1:2,000 to the H3K27Me3 plate and 1:6,000 to the H3 plate and incubated for 90 min at RT. Plates are washed 4× with PBST. For detection, 100 ul/well of TMB substrate (BioFx Laboratories, #TMBS) is added and plates incubated in the dark at RT for 5 min. Reaction is stopped with 100 ul/well 1N $H_2SO_4$. Absorbance at 450 nm is read on SpectaMax M5 Microplate reader.

7 Day PD Study

In order to test whether a compound can modulate the H3K27me3 histone mark in tumors in vivo, WSU-DLCL2 xenograft tumor bearing mice are treated with the compound at either 200 mg/kg BID or 400 mg/kg QD or vehicle (BID schedule) for 7 days. There are 4 animals per group. Animals are euthanized 3 h after the last dose and tumor is preserved in a frozen state as described above. Following histone extraction the samples are applied to ELISA assays using antibodies directed against the trimethylated state of histone H3K27 (H3K27me3) or total histone H3. Based on these data the ratio of globally methylated to total H3K27 is calculated. The mean global methylation ratios for all groups as measured by ELISA indicates target inhibition range compared to vehicle.

28 Day Efficacy Study in WSU-DLCL2 Xenograft Model

In order to test whether a compound could induce a tumor growth inhibition in vivo WSU-DLCL2 xenograft tumor bearing mice are treated with the compound at 12.5, 25 or 50 mg/kg QD for 28 days via intraperitoneal injection. Tumor volume and body weights are determined twice a week. A parallel cohort of mice (n=4 per group) is treated at the same doses for 7 days, and mice are euthanized on day 7, 3 h after the last dose for tumor sampling and assessment of target inhibition. The result of the ELISA measuring global methylation of H3K27me3 normalized to total H3 is determined.

Efficacy Study with Increasing Doses in WSU-DLCL2 Xenograft Model

In order to test whether a compound could induce an anti-tumor effect in vivo, WSU-DLCL2 xenograft tumor bearing mice are treated with a compound at, e.g., 37.5, 75 or 150 mg/kg TID for 28 days. There are 12 mice per group for the efficacy arm of the experiment. A parallel cohort is dosed for 7 days at the same doses and schedules for assessment of target inhibition after 7 days (n=6 per group). The tumor growth over the treatment course of 28 days for vehicle and compound treated groups is measured.

Histones are extracted from tumors collected after 7 days of dosing (parallel PD cohort) and at the end of the study on day 28 for the efficacy cohort (3 h after the last dose for both cohorts). The H3K27me3 methyl mark is assessed for modulation with treatment in a dose dependent matter.

Efficacy Study at Different Dose Schedules

To assess whether a compound would lead to tumor growth inhibition at other dosing schedules but TID a WSU-DLCL2 xenograft efficacy study is performed where TID, BID and QD schedules are compared side by side. There are 12 animals per group, and mice are treated for 28 days. The tumor growth over the treatment course of 28 days for vehicle and compound treated groups is measured.

On day 28 mice are euthanized and tumors were collected 3 h after the last dose for assessment of target inhibition.

EXAMPLE 8

Anti-cancer Effect on the KARPAS-422 Human Diffused Large B-Cell Lymphoma Mouse Xenograft Model A test compound is analyzed for its anti-cancer activity in KARPAS-422 mouse xenograft model, which is a human diffused large B-Cell lymphoma xenograft model. 45 female of CAnN.Cg-Foxn1nu/CrlCrlj mice (Charles River Laboratories Japan) with KARPAS-422 tumors whose mean tumor volume (TV) reached approximately 150 mm$^3$ are selected based on their TVs, and are randomly divided into five groups. The oral administration of compound (e.g., 80.5, 161, 322, and 644 mg/kg) or vehicle is started on day 1. Compound is given once daily on day 1 and day 29 and twice daily everyday from day 2 to day 28. The administration volume (0.1 mL/10 g body weight) is calculated from the body weight before administration. The TV and body weight are measured twice a week. The design for this experiment is shown in Table 5.

TABLE 5

Dosing Scheme

| Group | No. of Animals | Treatment (twice a day) | Route and Schedule |
|---|---|---|---|
| 1 | 9 | Vehicle (0.5% Methyl Cellulose, 0.1% Tween-80) | PO; BID x 28 days |
| 2 | 9 | 80.5 mg/kg Compound | PO; BID x 28 days |
| 3 | 9 | 161 mg/kg Compound | PO; BID x 28 days |
| 4 | 9 | 322 mg/kg Compound | PO; BID x 28 days |
| 5 | 9 | 644 mg/kg Compound | PO; bid x 28 days |

TV is calculated from caliper measurements by the formula for the volume of a prolate ellipsoid $(L \times W^2)/2$ where L and W are the respective orthogonal length and width measurements (mm).

Data are expressed as the mean±standard deviation (SD). The differences in TV between the vehicle-treated and compound-treated groups are analyzed by a repeated measures analysis of variance (ANOVA) followed by the Dunnett-type multiple comparison test. A value of P<0.05 (two sided) is considered statistically significant. Statistical analyses are performed using the Prism 5 software package version 5.04 (GraphPad Software, Inc., CA, USA).

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of formula (VIa) or a pharmaceutically acceptable salt thereof

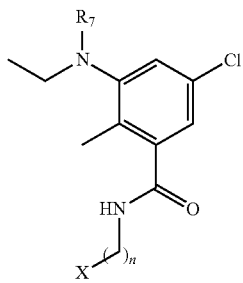

(VIa)

wherein $R_7$ is piperidinyl, tetrahydropyran, cyclopentyl, or cyclohexyl, each optionally substituted with one -$Q_5$-$T_5$; n is 1 or 2; and X is

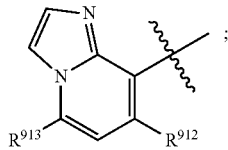

wherein
each of $R^{912}$ and $R^{913}$, independently, is -$Q_7$-$T_7$, in which $Q_7$ is a bond or $C_1$-$C_3$ alkyl linker each optionally substituted with halo, cyano, hydroxyl or $C_1$-$C_6$ alkoxy, and $T_7$ is H, —$OR_n$, —$NR_nR_r$, —$C(O)R_n$, —$C(O)OR_n$, —$C(O)NR_nR_r$, —$S(O)_2R_n$, —$S(O)_2NR_nR_r$, or $R_{S9}$, in which each of $R_n$ and $R_r$, independently is H or $R_{S10}$, each of $R_{S9}$ and $R_{S10}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_n$ and $R_r$, together with the N atom to which they are attached, form a 4 to 12-membered heterocycloalkyl ring having 0 or 1 additional heteroatom, and each of $R_{S9}$, $R_{S10}$, and the 4 to 12-membered heterocycloalkyl ring formed by $R_n$ and $R_r$, is optionally substituted with one or more -$Q_8$-$T_8$, wherein $Q_8$ is a bond or $C_1$-$C_3$ alkyl linker each optionally substituted with halo, cyano, hydroxyl or $C_1$-$C_6$ alkoxy, and $T_8$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, —$OR_s$, —$COOR_S$, —$S(O)_2R_s$, —$NR_sR_t$, and —$C(O)NR_sR_t$, each of $R_s$ and $R_t$ independently being H or $C_1$-$C_6$ alkyl, or -$Q_8$-$T_8$ is oxo; or -$Q_7$-$T_7$ is oxo; or any two neighboring -$Q_7$-$T_7$ together with the atoms to which they are attached form a 5- or 6-membered ring optionally containing 1-4 heteroatoms selected from N, O and S and optionally substituted with one or more substituents selected from the group consisting of halo, hydroxyl, —COOH, —C(O)O —$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

2. A compound selected from the following:

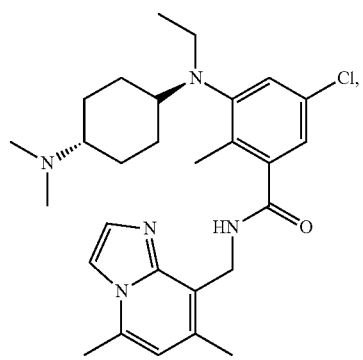

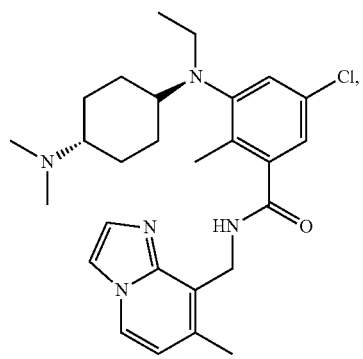

149
-continued
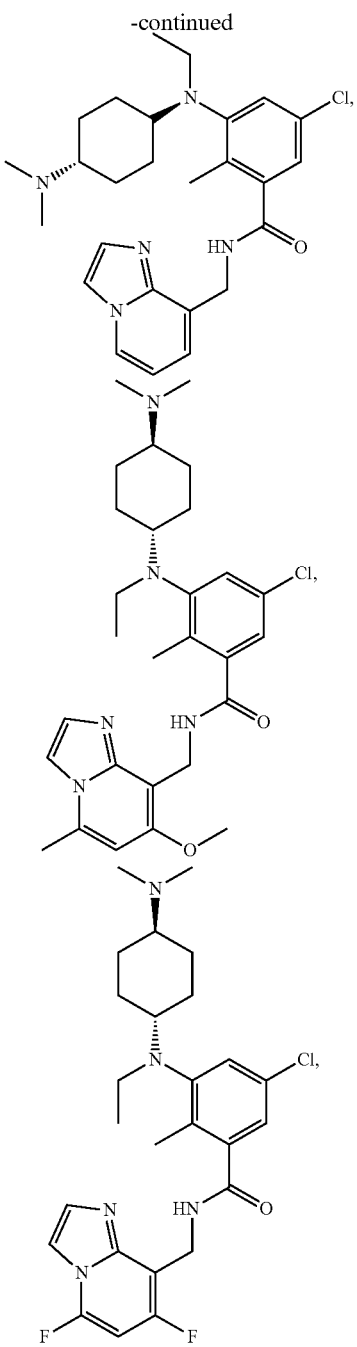
150
-continued
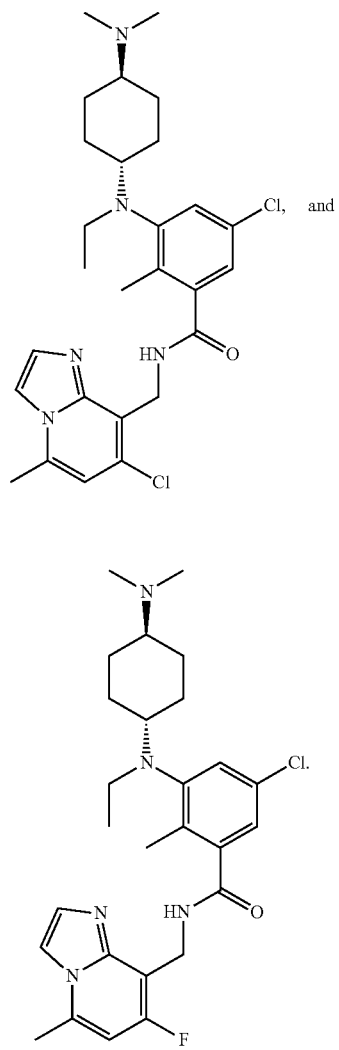
3. A pharmaceutical composition comprising a compound of claim 1 or a pharmaceutically acceptable salt thereof and a pharmaceutically acceptable carrier.
4. A pharmaceutical composition comprising a compound of claim 2 or a pharmaceutically acceptable salt thereof and a pharmaceutically acceptable carrier.
* * * * *